United States Patent
Kao et al.

(10) Patent No.: US 10,960,030 B2
(45) Date of Patent: Mar. 30, 2021

(54) ANTI-OBESITY MICROBIOTA COMPOSITIONS AND PREPARATION METHODS AND USES THEREOF

(71) Applicant: NATIONAL HEALTH RESEARCH INSTITUTES, Zhunan (TW)

(72) Inventors: Cheng-Yuan Kao, Zhunan (TW); Jhen-Wei Ruan, Zhunan (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 80 days.

(21) Appl. No.: 16/093,787

(22) PCT Filed: Apr. 14, 2017

(86) PCT No.: PCT/US2017/027599
§ 371 (c)(1),
(2) Date: Oct. 15, 2018

(87) PCT Pub. No.: WO2017/180987
PCT Pub. Date: Oct. 19, 2017

(65) Prior Publication Data
US 2019/0076485 A1 Mar. 14, 2019

Related U.S. Application Data

(60) Provisional application No. 62/323,053, filed on Apr. 15, 2016.

(51) Int. Cl.
| | |
|---|---|
| *A61K 35/74* | (2015.01) |
| *C12N 1/20* | (2006.01) |
| *A23L 33/00* | (2016.01) |
| *A23L 33/135* | (2016.01) |
| *A61P 3/04* | (2006.01) |
| *A61K 9/00* | (2006.01) |

(52) U.S. Cl.
CPC .............. *A61K 35/74* (2013.01); *A23L 33/00* (2016.08); *A23L 33/135* (2016.08); *A23L 33/30* (2016.08); *A61K 9/0053* (2013.01); *A61P 3/04* (2018.01); *C12N 1/20* (2013.01); *A01K 2207/20* (2013.01); *A01K 2267/0362* (2013.01); *A23V 2002/00* (2013.01)

(58) Field of Classification Search
CPC combination set(s) only.
See application file for complete search history.

(56) References Cited

U.S. PATENT DOCUMENTS

2011/0207190 A1  8/2011  Subramanian et al.
2013/0224155 A1  8/2013  Kaplan et al.

FOREIGN PATENT DOCUMENTS

WO   WO2016033439 A2   3/2016

OTHER PUBLICATIONS

Ruan et al., "Dual-specificity phosphatase 6 deficiency regulates gut microbiome and transcriptome response against diet-induced obesity in mice," Nature Microbiology, Nov. 28, 2016, vol. 2, pp. 1-12.

*Primary Examiner* — Heidi Reese
(74) *Attorney, Agent, or Firm* — Muncy, Geissler, Olds & Lowe, P.C.

(57) ABSTRACT

The present invention relates to microbiota compositions and their preparation methods and uses. Particularly, the present invention provides microbiota compositions collected from a dual-specificity phosphatase 6 (dusp6) deficient mammal, which is effective in altering a relative abundance of gut microbiota and also useful in reducing body weight, fat mass, and/or size of adipocytes and increasing oxygen consumption and/or energy expenditure and thus can be used to treat or prevent obesity or its associated disorders or conditions in a subject in need.

20 Claims, 32 Drawing Sheets

Specification includes a Sequence Listing.

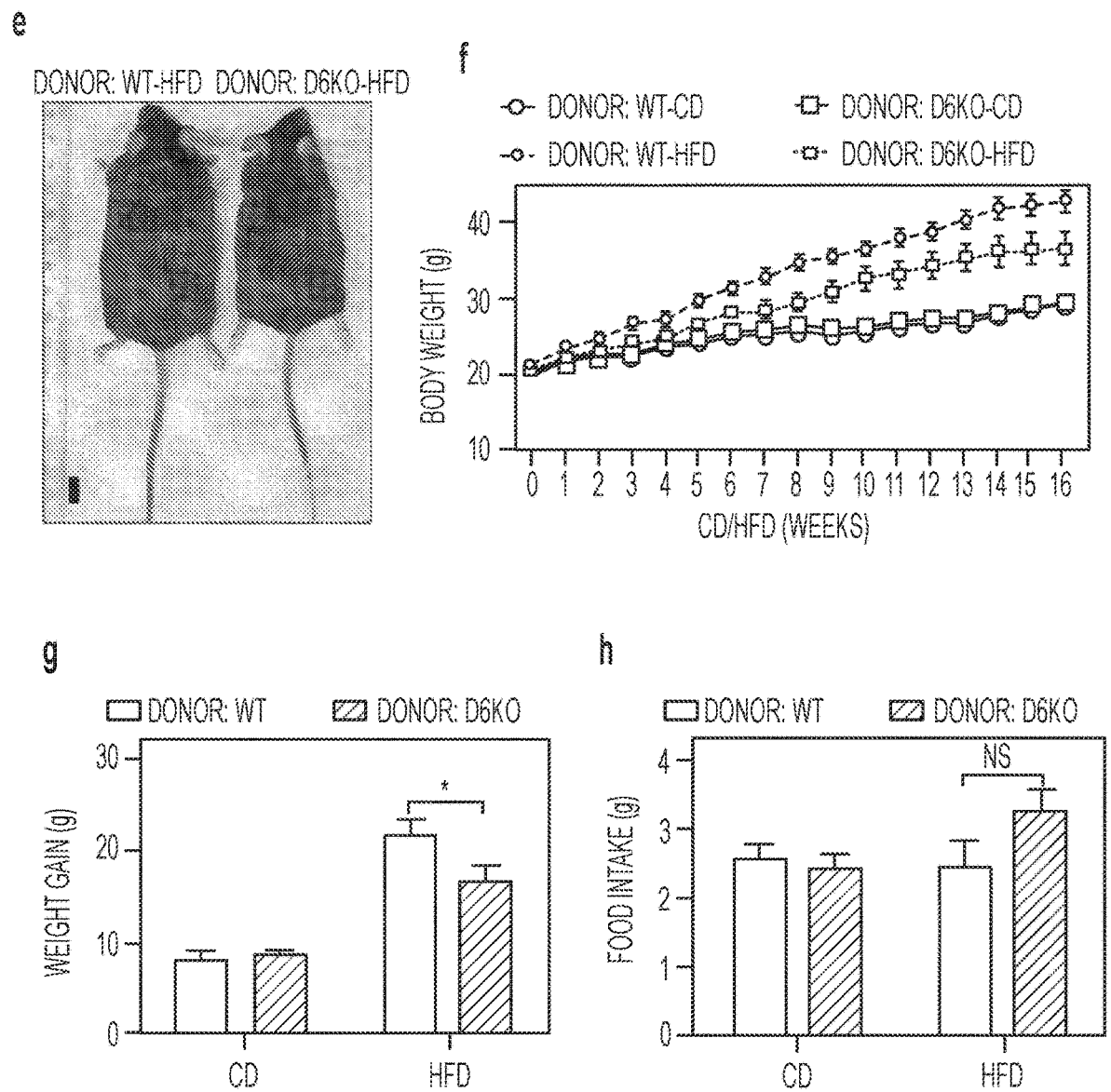
Fig. 1 (Cont')

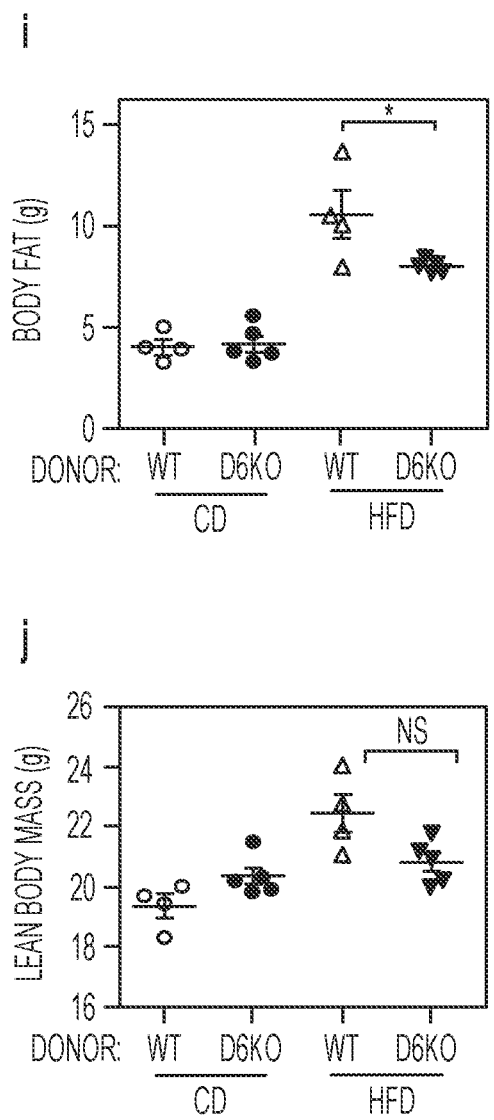
Fig. 1 (Cont')

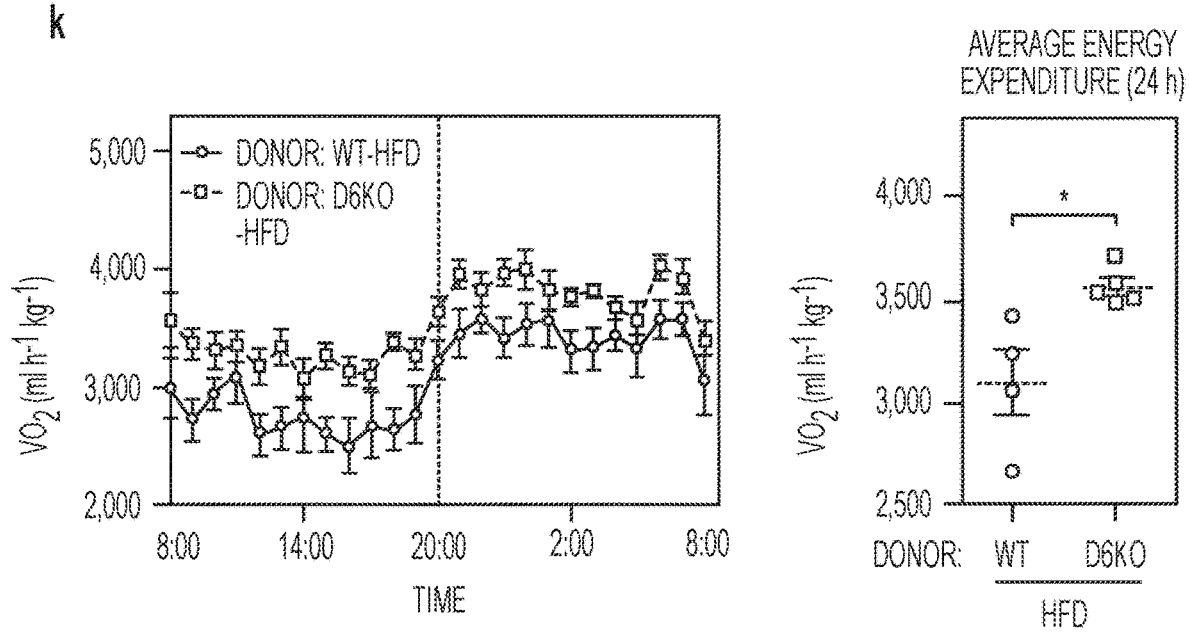
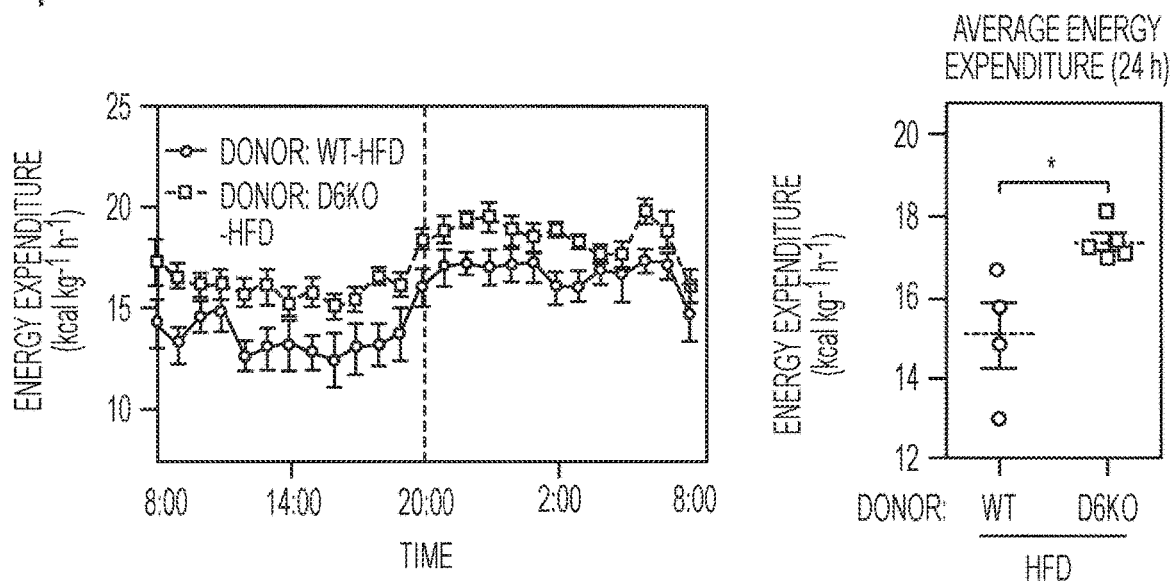
Fig. 1 (Cont')

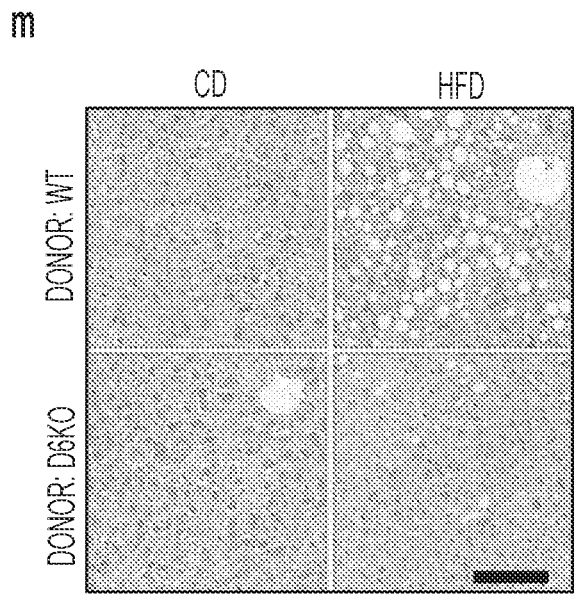
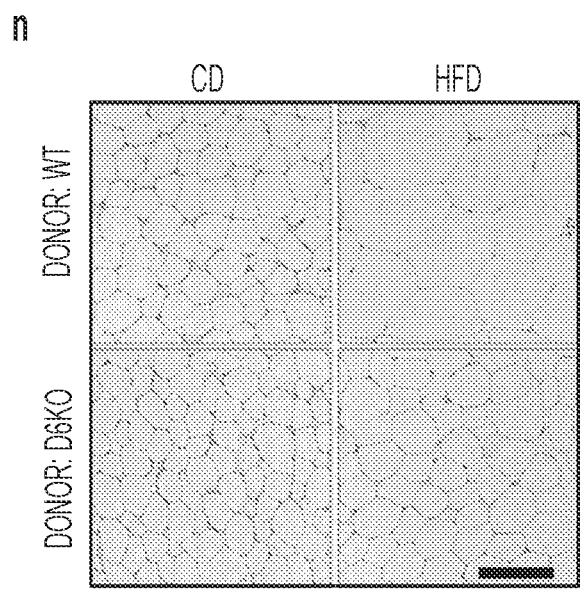
Fig. 1 (Cont')

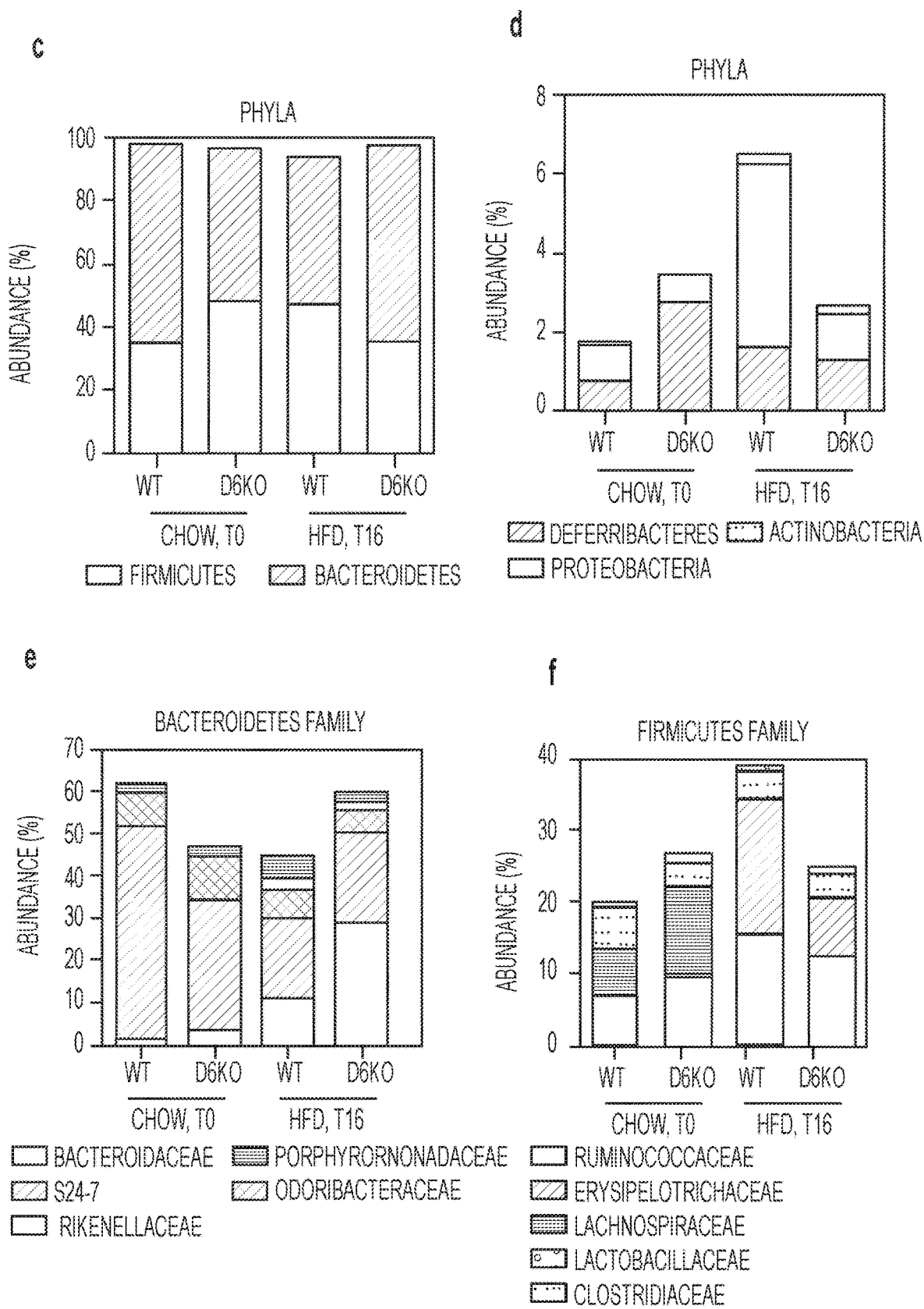
Fig. 2 (Cont')

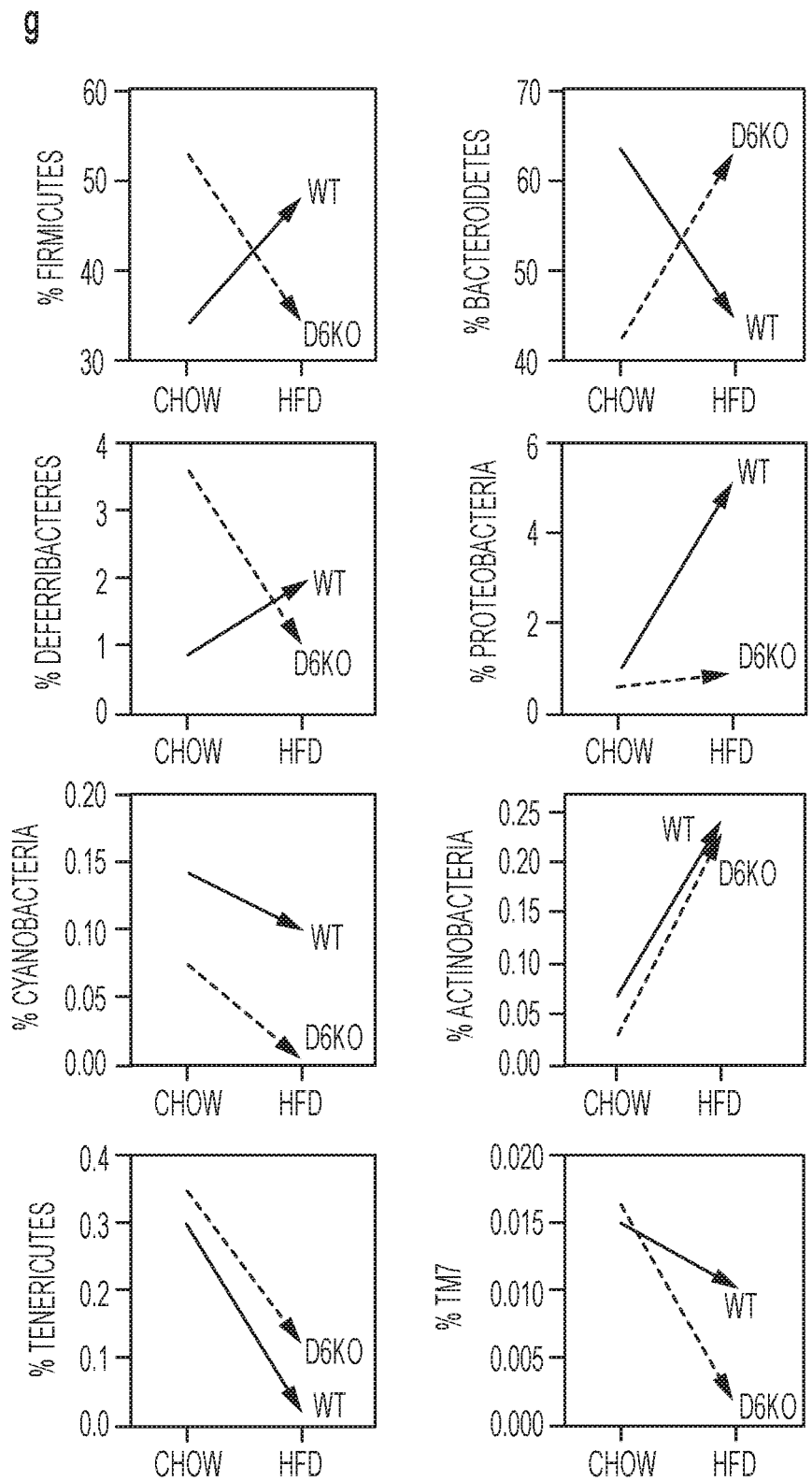
Fig. 2 (Cont')

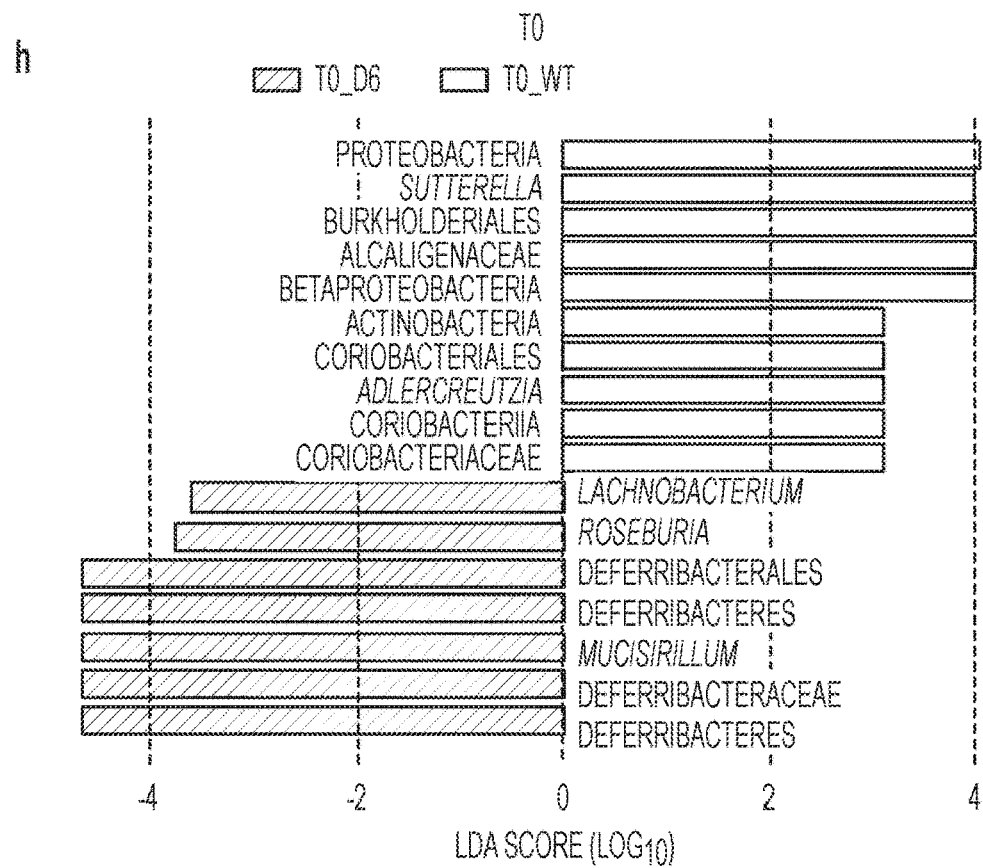
Fig. 2 (Cont')

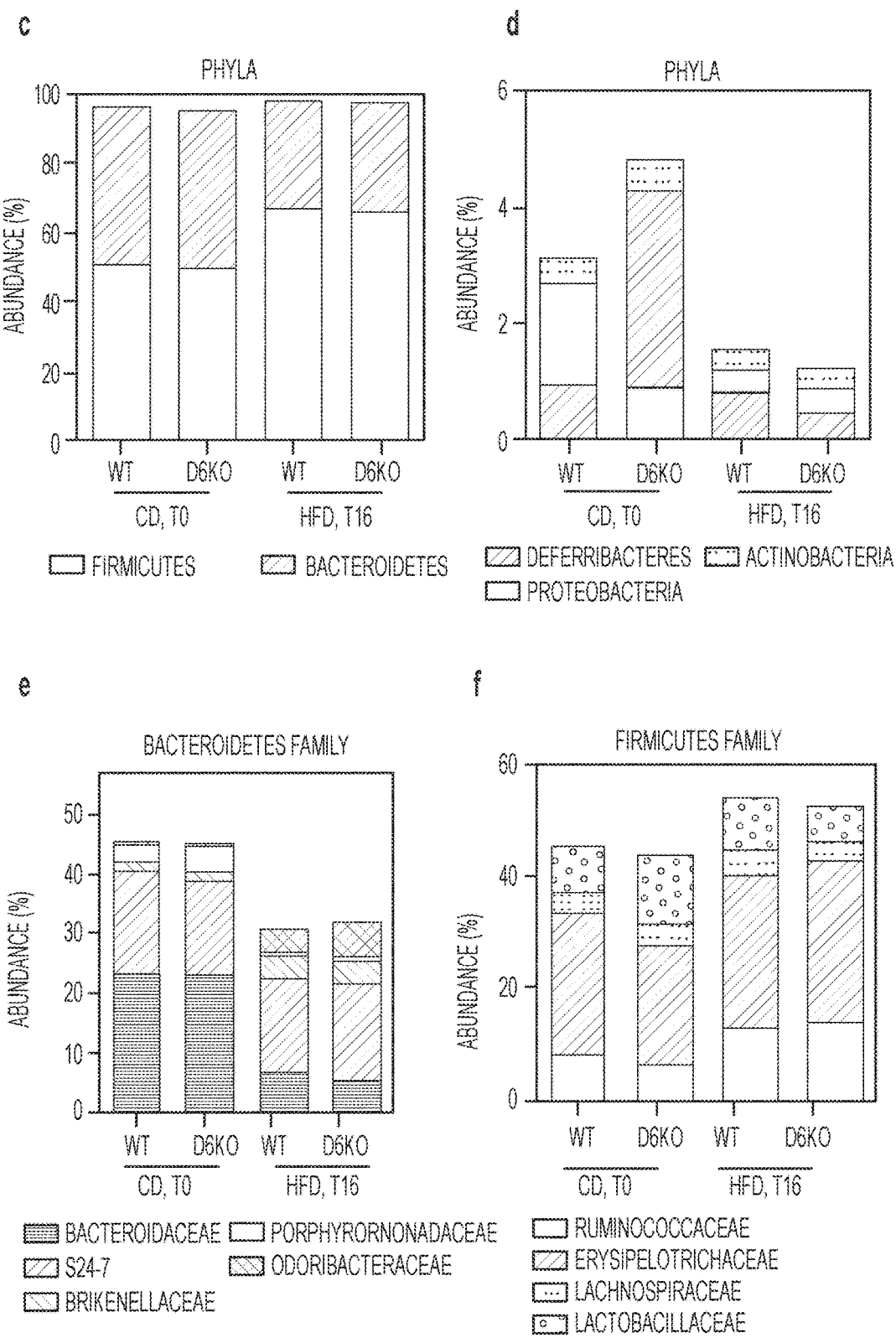
Fig. 3 (Cont')

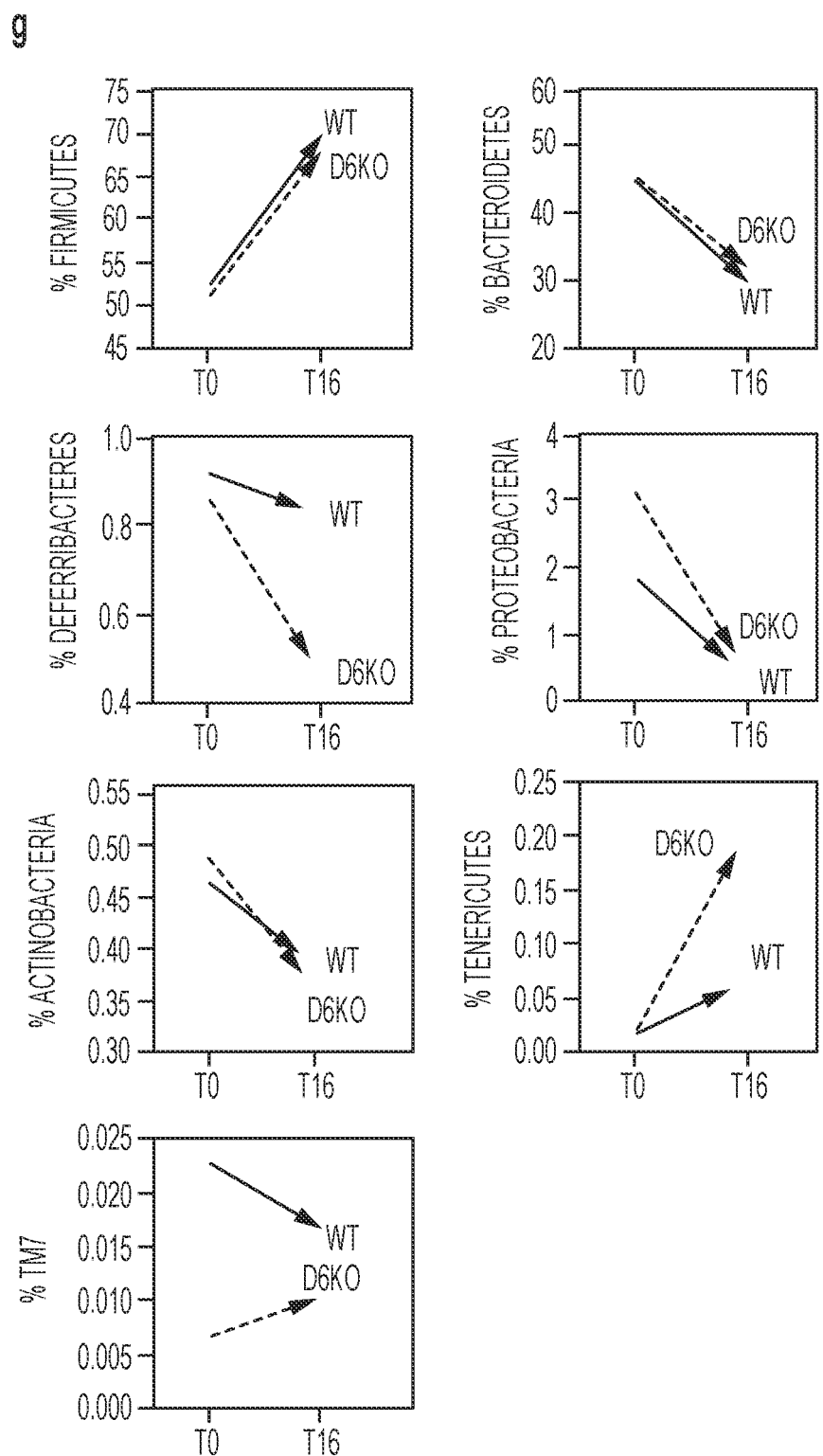
Fig. 3 (Cont')

h
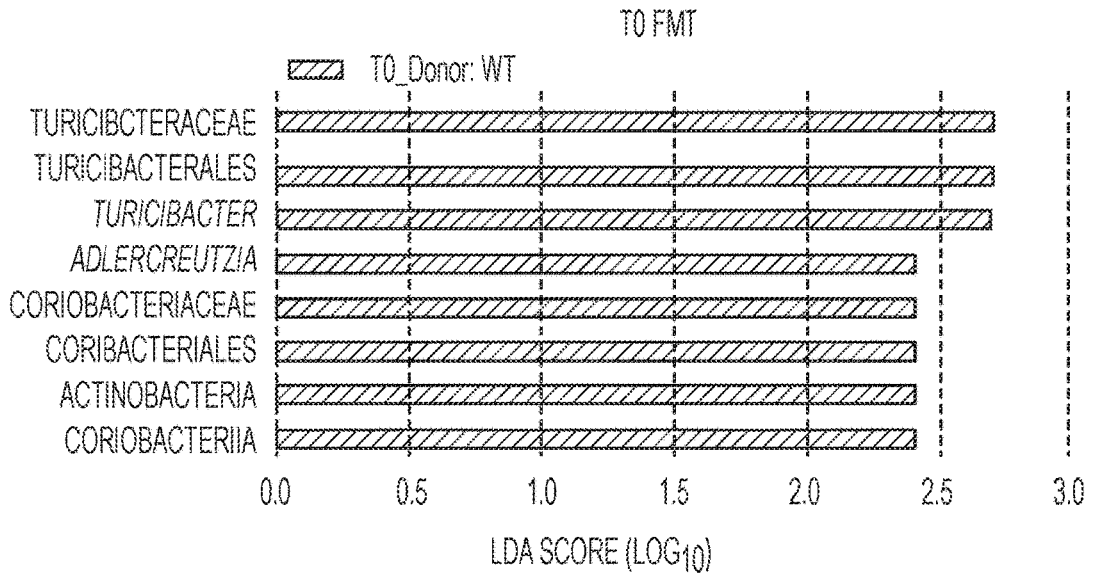
i
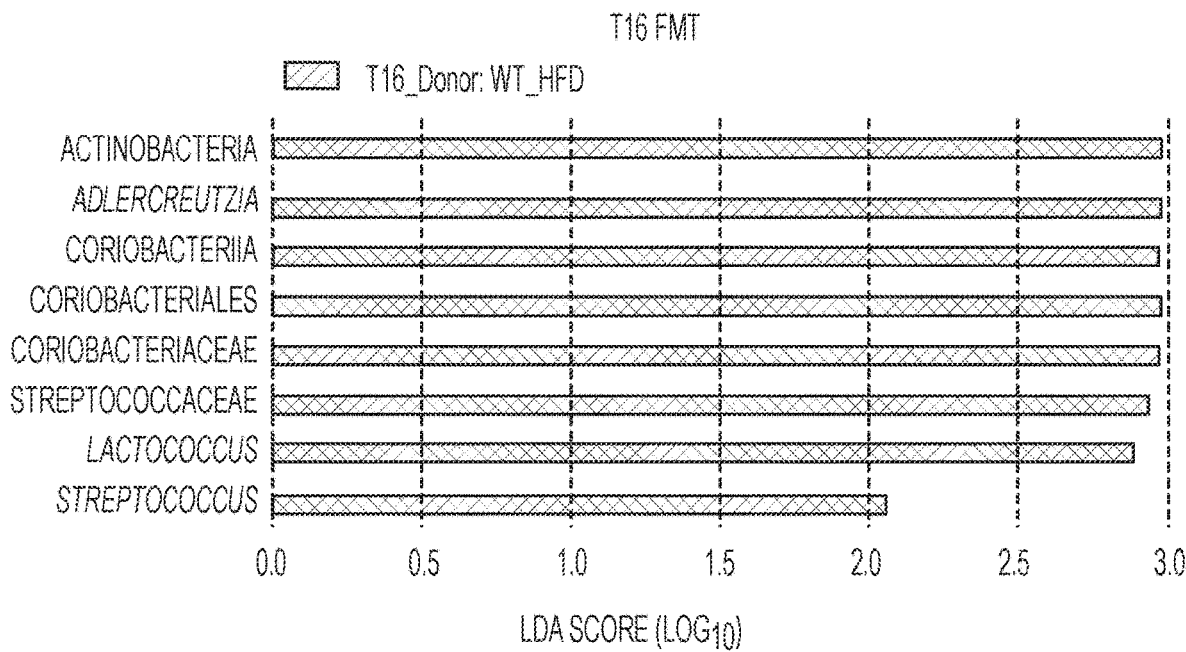
Fig. 3 (Cont')

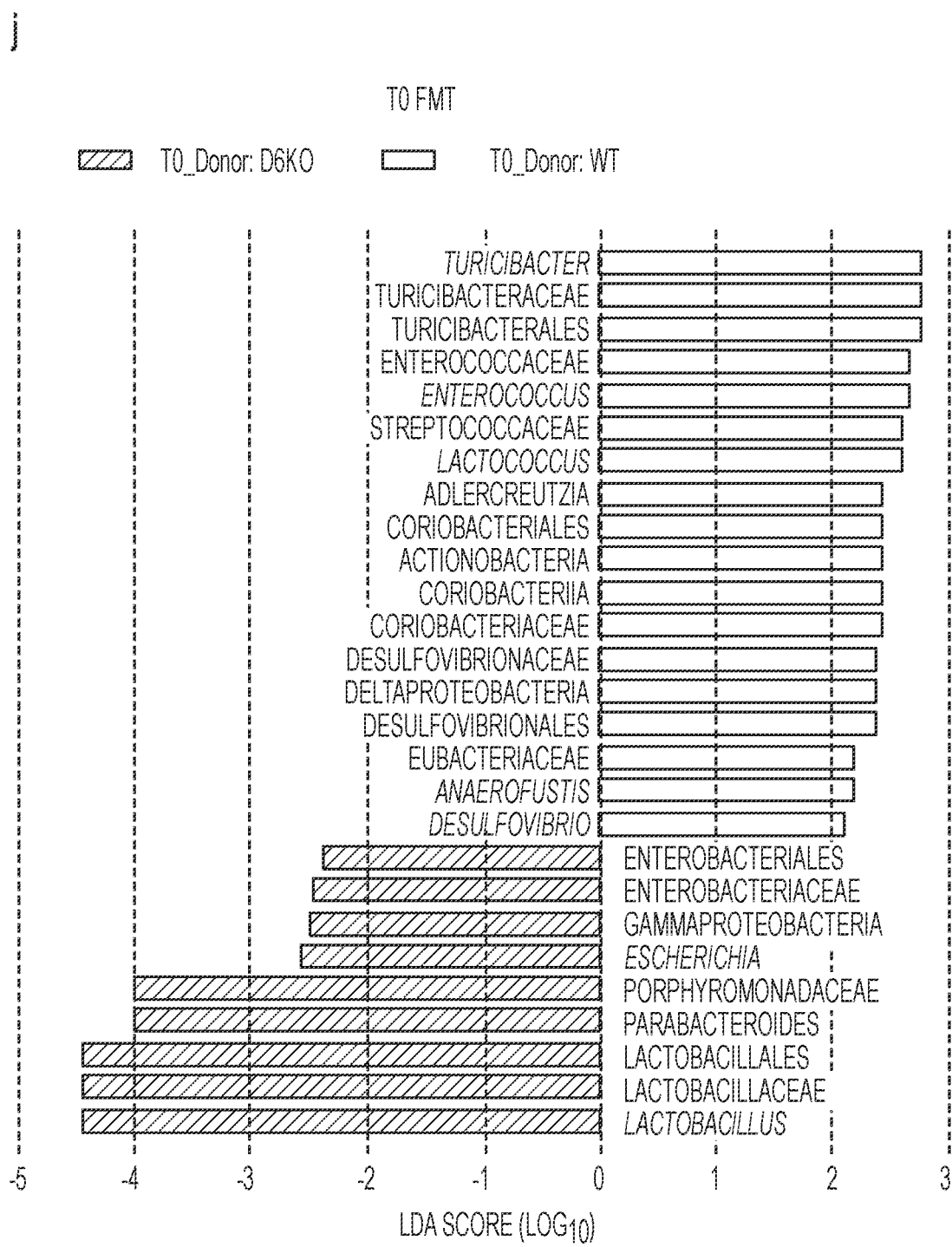
Fig. 3 (Cont')

b
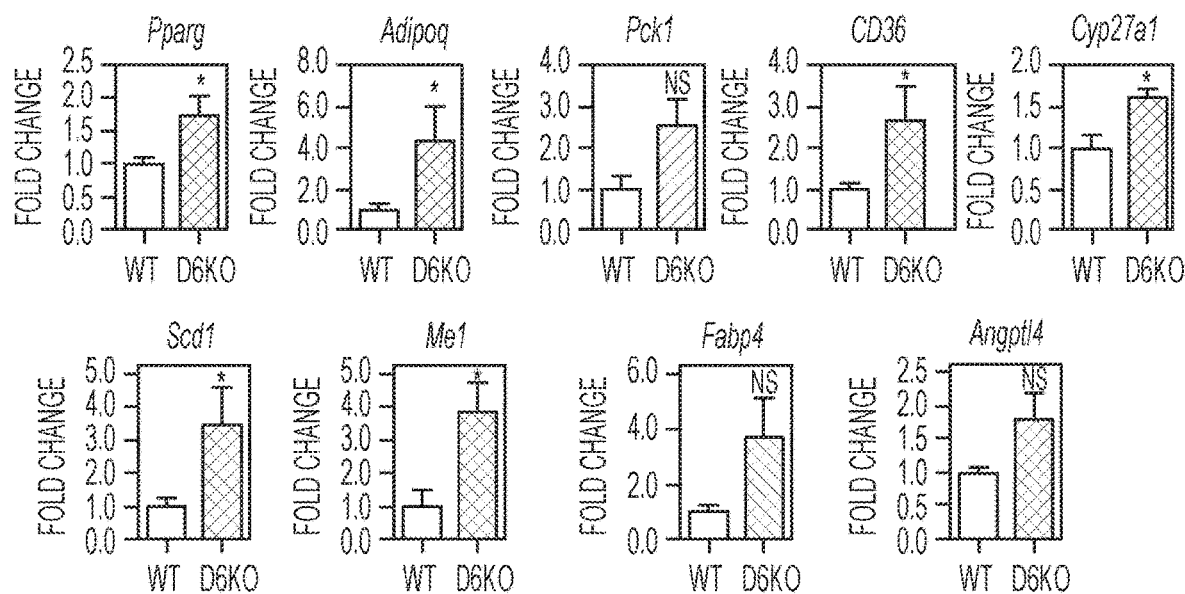
c
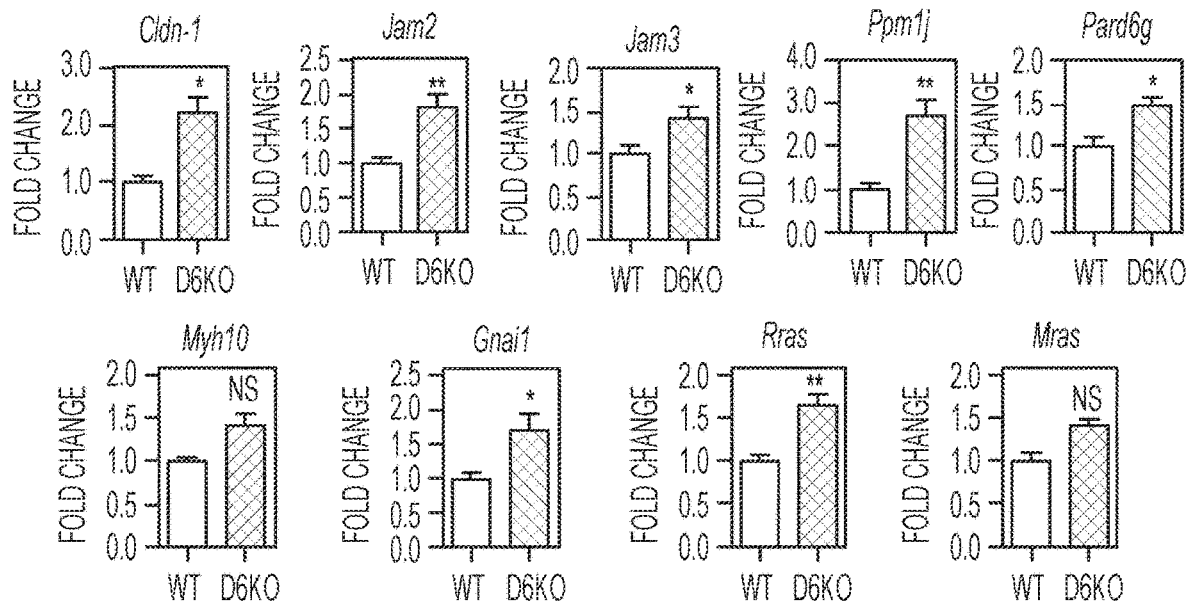
Fig. 4 (Cont')

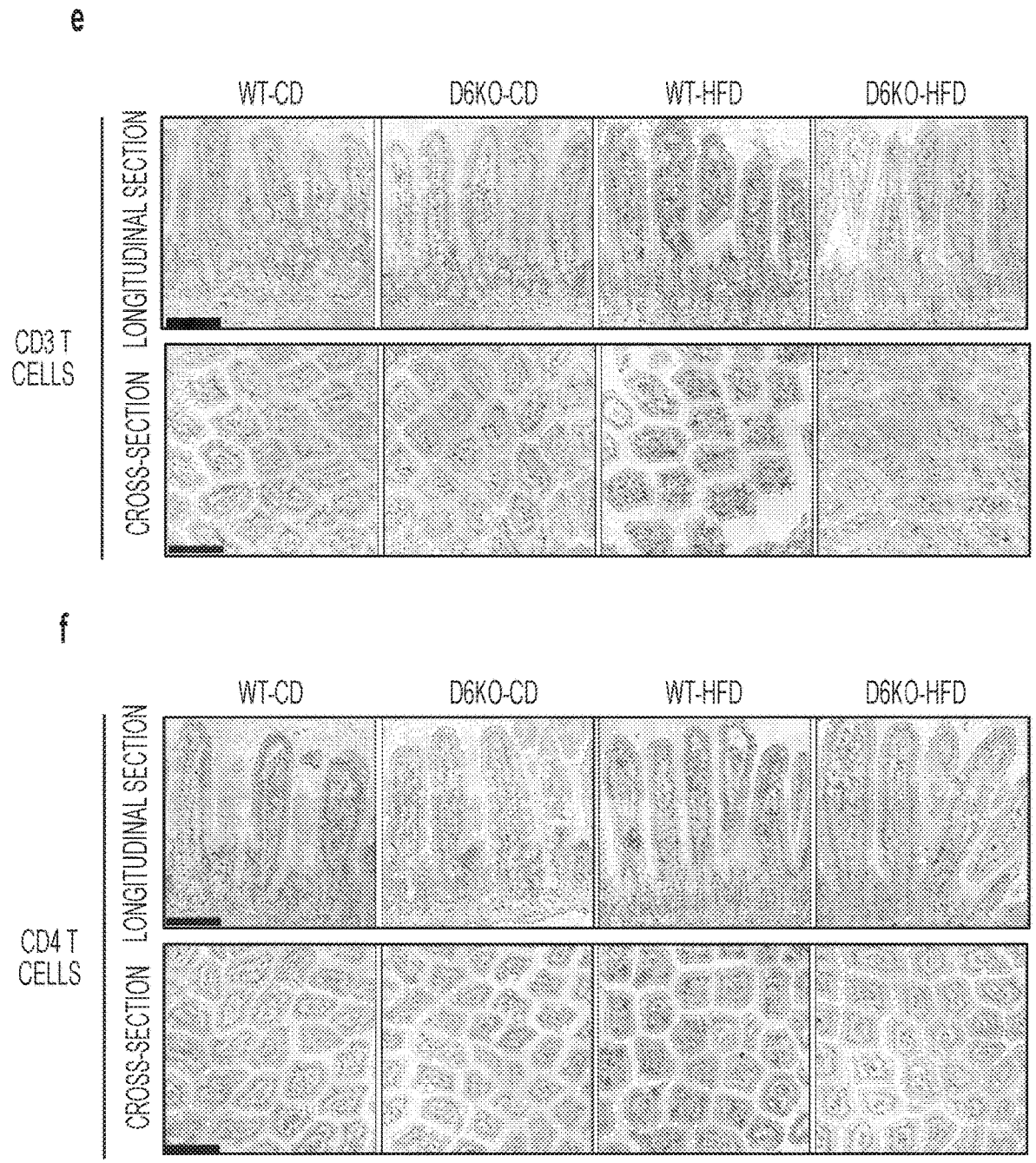
Fig. 5(Cont')

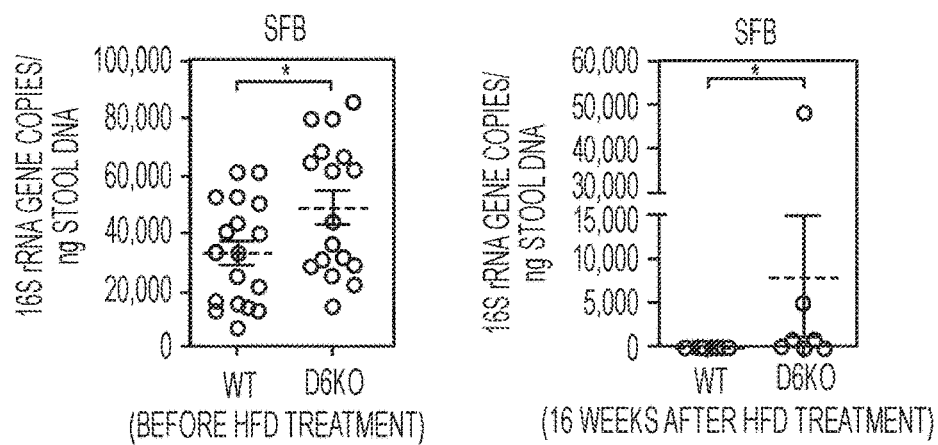
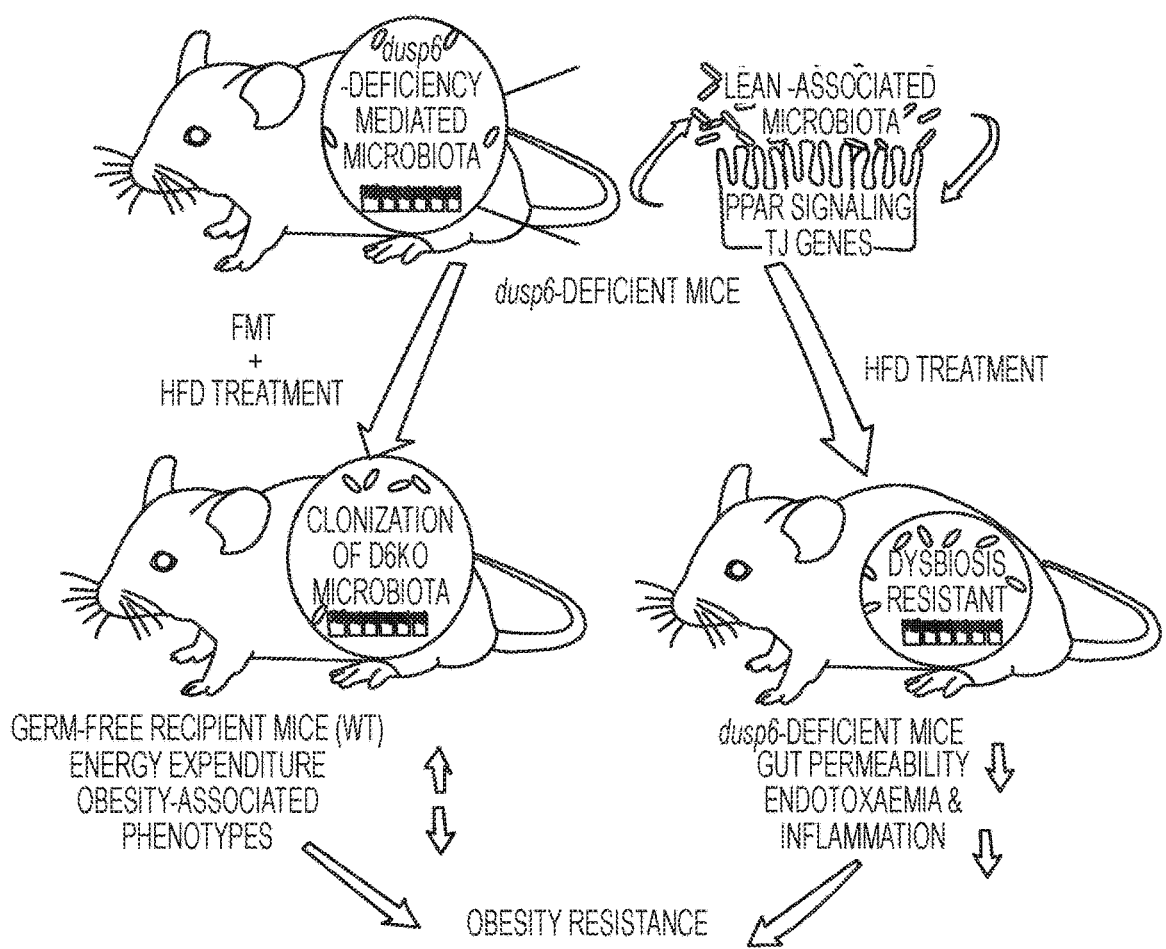
Fig.6 (Cont')

e
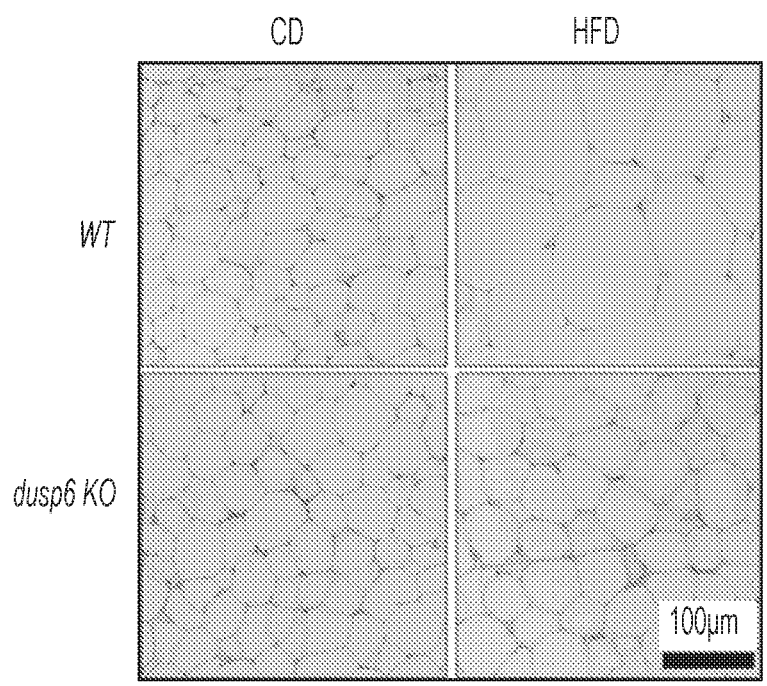
f
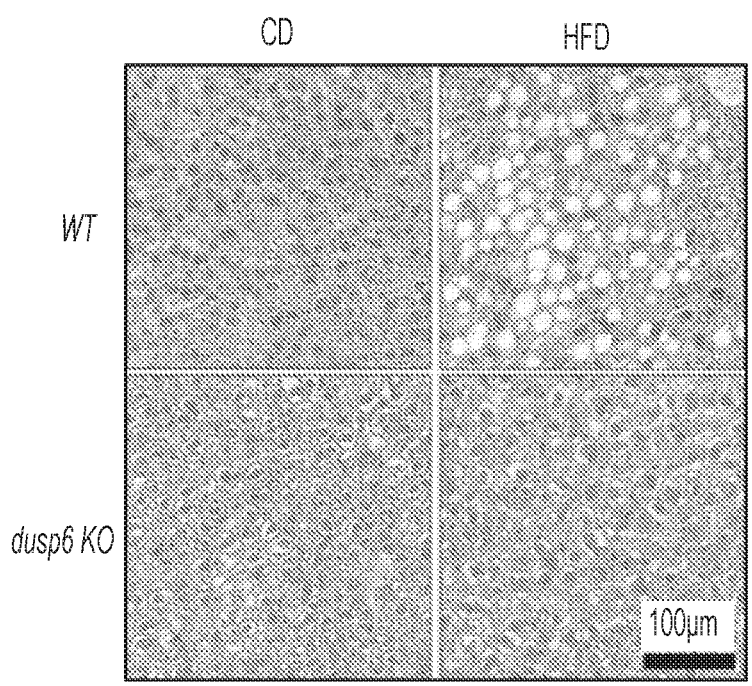
Fig.7 (Cont')

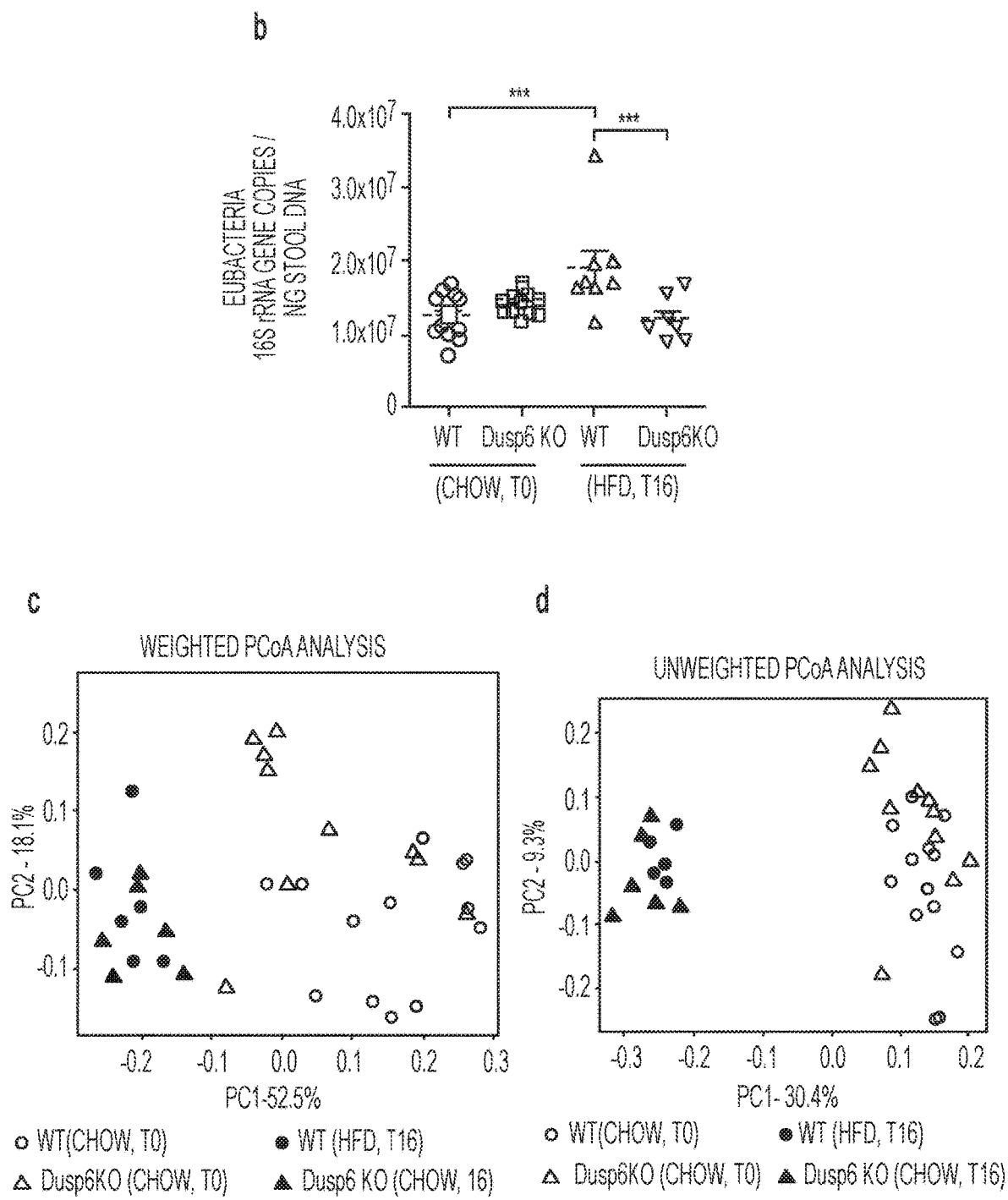
Fig.8 (Cont')

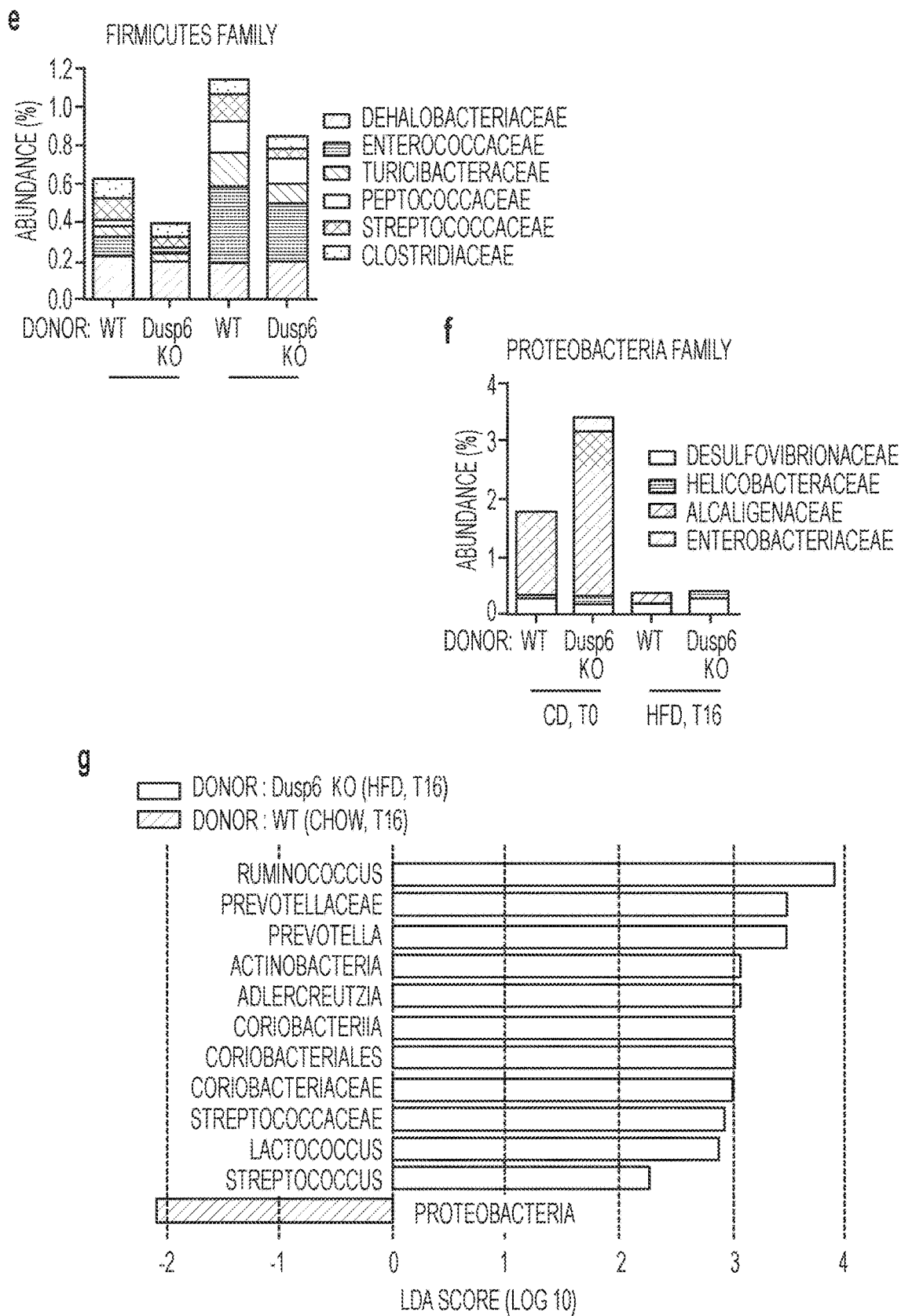
Fig.8 (Cont')

h
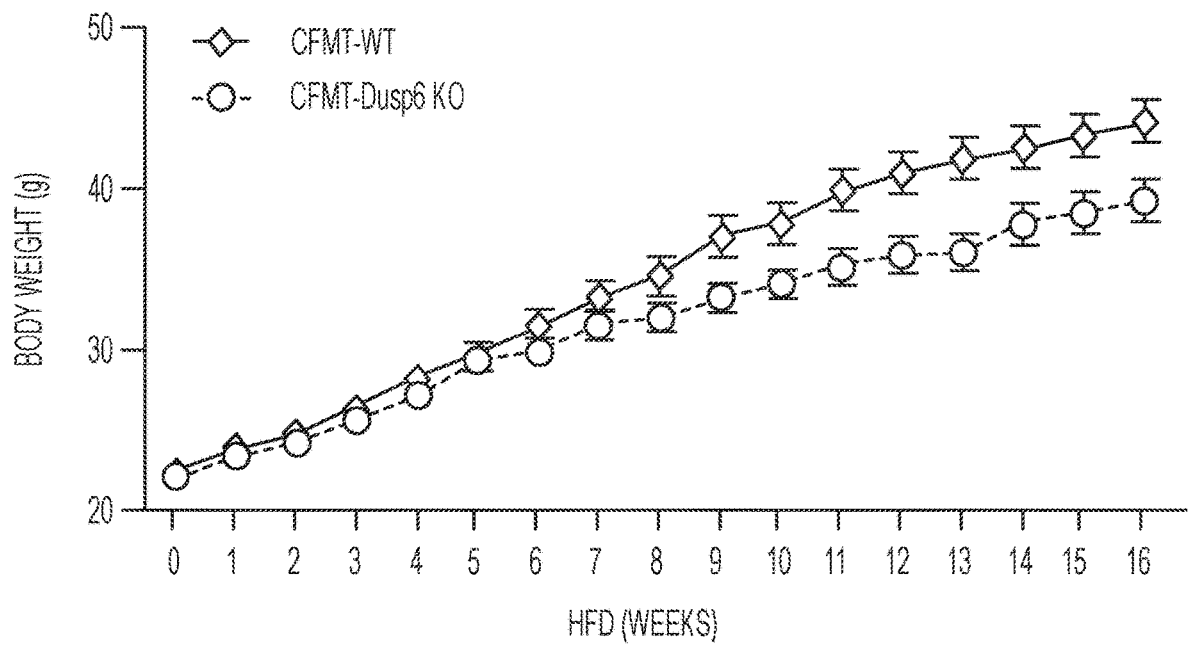
i
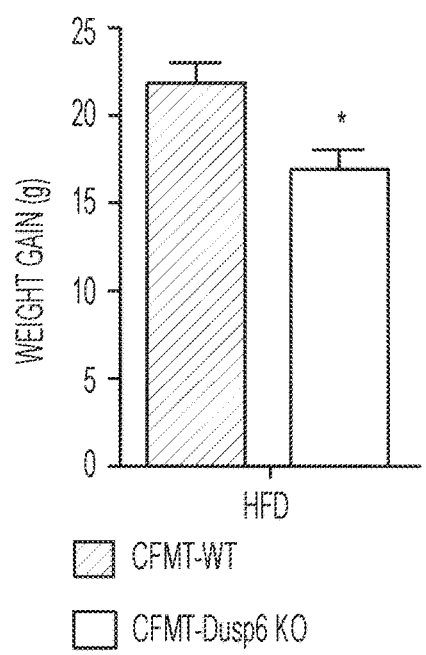
Fig.8 (Cont')

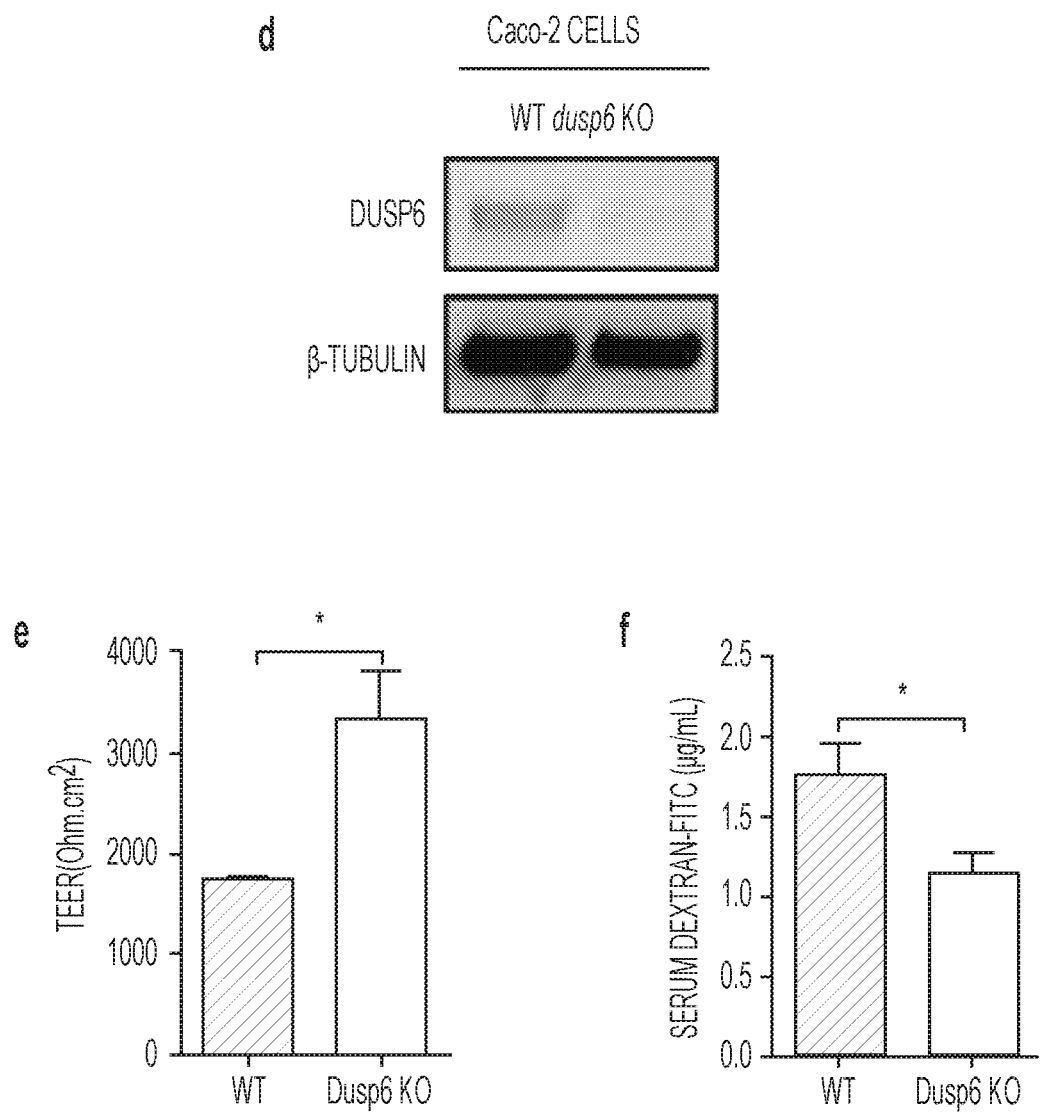
Fig. 9 (Cont')

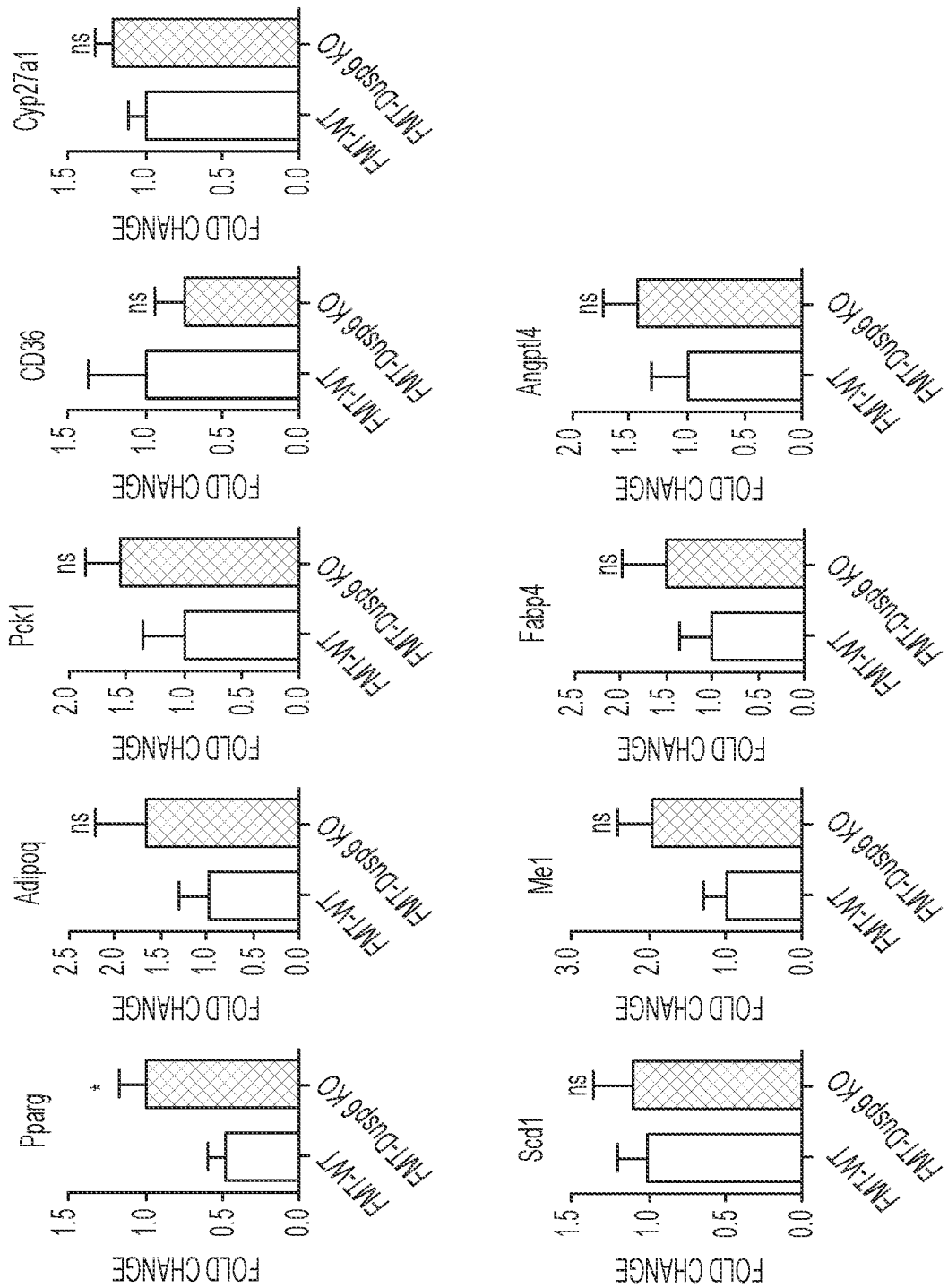
Fig. 9 (Cont')

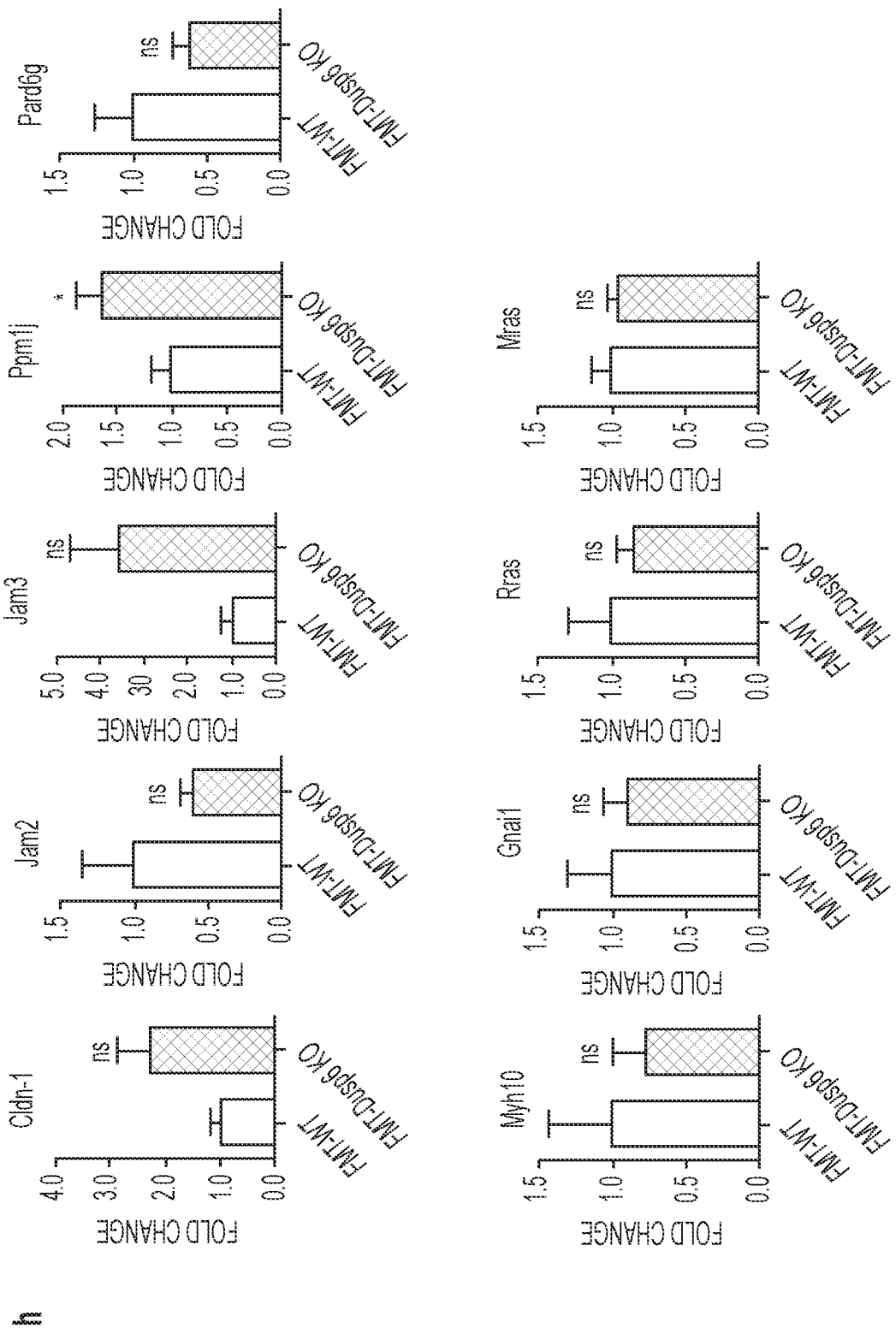
Fig. 9 (Cont')

SEQUENCE LISTING

```
<160> NUMBER OF SEQ ID NOS: 5

<210> SEQ ID NO 1
<211> LENGTH: 381
<212> TYPE: PRT
<213> ORGANISM: Mus musculus

<400> SEQUENCE: 1

Met Ile Asp Thr Leu Arg Pro Val Pro Phe Ala Ser Glu Met Ala Ile
```

```
               1               5                    10                   15
            Cys Lys Thr Val Ser Trp Leu Asn Glu Gln Leu Glu Leu Gly Asn Glu
                            20                  25                  30
            Arg Leu Leu Leu Met Asp Cys Arg Pro Gln Glu Leu Tyr Glu Ser Ser
                            35                  40                  45
            His Ile Glu Ser Ala Ile Asn Val Ala Ile Pro Gly Ile Met Leu Arg
                50                  55                  60
            Arg Leu Gln Lys Gly Asn Leu Pro Val Arg Ala Leu Phe Thr Arg Cys
            65                  70                  75                  80
            Glu Asp Arg Asp Arg Phe Thr Arg Arg Cys Gly Thr Asp Thr Val Val
                                85                  90                  95
            Leu Tyr Asp Glu Asn Ser Ser Asp Trp Asn Glu Asn Thr Gly Gly Glu
                            100                 105                 110
            Ser Val Leu Gly Leu Leu Lys Lys Leu Lys Asp Glu Gly Cys Arg
                            115                 120                 125
            Ala Phe Tyr Leu Glu Gly Gly Phe Ser Lys Phe Gln Ala Glu Phe Ala
                            130                 135                 140
            Leu His Cys Glu Thr Asn Leu Asp Gly Ser Cys Ser Ser Ser Pro
            145                 150                 155                 160
            Pro Leu Pro Val Leu Gly Leu Gly Gly Leu Arg Ile Ser Ser Asp Ser
                            165                 170                 175
            Ser Ser Asp Ile Glu Ser Asp Leu Asp Arg Asp Pro Asn Ser Ala Thr
                            180                 185                 190
            Asp Ser Asp Gly Ser Pro Leu Ser Asn Ser Gln Pro Ser Phe Pro Val
                            195                 200                 205
            Glu Ile Leu Pro Phe Leu Tyr Leu Gly Cys Ala Lys Asp Ser Thr Asn
                            210                 215                 220
            Leu Asp Val Leu Glu Glu Phe Gly Ile Lys Tyr Ile Leu Asn Val Thr
            225                 230                 235                 240
            Pro Asn Leu Pro Asn Leu Phe Glu Asn Ala Gly Glu Phe Lys Tyr Lys
                            245                 250                 255
            Gln Ile Pro Ile Ser Asp His Trp Ser Gln Asn Leu Ser Gln Phe Phe
                            260                 265                 270
            Pro Glu Ala Ile Ser Phe Ile Asp Glu Ala Arg Gly Lys Asn Cys Gly
                            275                 280                 285
            Val Leu Val His Cys Leu Ala Gly Ile Ser Arg Ser Val Thr Val Thr
                            290                 295                 300
            Val Ala Tyr Leu Met Gln Lys Leu Asn Leu Ser Met Asn Asp Ala Tyr
            305                 310                 315                 320
            Asp Ile Val Lys Met Lys Lys Ser Asn Ile Ser Pro Asn Phe Asn Phe
                            325                 330                 335
            Met Gly Gln Leu Leu Asp Phe Glu Arg Thr Leu Gly Leu Ser Ser Pro
                            340                 345                 350
            Cys Asp Asn Arg Val Pro Thr Pro Gln Leu Tyr Phe Thr Thr Pro Ser
                            355                 360                 365
            Asn Gln Asn Val Tyr Gln Val Asp Ser Leu Gln Ser Thr
                            370                 375                 380

<210> SEQ ID NO 2
<211> LENGTH: 2814
<212> TYPE: DNA
<213> ORGANISM: Mus musculus

<400> SEQUENCE: 2
```

-continued

```
atccattgag gagctgcctc gcacaggggg tgtgctctcg cggagtccta gggactgtga    60
gcaaacccag tcttgaataa tccggcgaga acaccgggt tggatccgag gtgcagcctc    120
agagggaagg attaagagcc gctagacttt ttttcttttc cctttttctc ctctcagtgg    180
cacggagtcc gaattaattg gatttcattc actgggtagg aacaaaactg gcaccttca    240
ttcagagaga gagattcatt gactcggaga gtgatctggt gcagagggac caccgacttg    300
acttctgtgt cgcttttccct aaccgctagc ctcggcttgg gaaaggcgag gcggaatcaa    360
accccgctcc gagagcggga gcttcgcgca gcgtgctcgg cctatgcctg cctcgagggg    420
cgtctgctag gcaccccgcc ttctcctgca gctcgacccc catgatagat acgctcagac    480
ccgtgccctt cgcgtcggaa atggcgatct gcaagacggt gtcgtggctc aacgagcagc    540
tggagctggg caacgaacgg cttctgctga tggactgccg accacaggag ctgtacgagt    600
cgtcacacat cgaatctgcc attaatgtgg ccatccccgg catcatgctg cggcgtctgc    660
agaagggcaa cctgcccgtg cgtgcgctct cacgcgctg cgaggaccgg accgctttta    720
ccaggcgctg cggcaccgac accgtggtgc tgtacgacga aatagcagc gactggaatg    780
agaacactgg tggagagtcg gtcctcgggc tgctgctcaa gaaactcaaa gacgagggct    840
gccgggcgtt ctacctggaa ggtggcttca gtaagttcca ggccgagttc gccctgcact    900
gcgagaccaa tctagacggc tcgtgcagca gcagttcccc gcctttgcca gtgctggggc    960
tcggggcct gcggatcagc tcggactctt cctcggacat tgagtctgac cttgaccgag    1020
accccaatag tgcaacggac tctgatggca gcccgctgtc caacagccag ccttccttcc    1080
cggtggagat tttgcccttc ctttacctgg gctgtgccaa ggactcgacc aacttggacg    1140
tgttggaaga gtttggcatc aagtacatct gaatgtcac ccccaatttg cccaatctgt    1200
ttgagaatgc gggcgagttc aaatacaagc aaattcctat ctcggatcac tggagccaaa    1260
acctgtccca gttttttccct gaggccattt ctttcataga tgaagcccga ggcaaaaact    1320
gtggtgtcct ggtgcattgc ttggcaggta tcagccgctc tgtcaccgtg acagtggcgt    1380
acctcatgca gaagctcaac ctgtccatga acgatgctta cgacattgtt aagatgaaga    1440
agtccaacat ctccccccaac ttcaacttca tgggccagct gcttgacttc gaaaggaccc    1500
tgggactgag cagcccttgt gacaaccgtg tccccactcc gcagctgtac ttcaccacgc    1560
cctccaacca gaacgtctac caggtggact ccctgcagtc tacgtgaaag gcacccacct    1620
ctcctagccg ggagttgtcc ccattccttc agttcctctt gagcagcatc gaccaggctg    1680
cttttctttct gtgtgtggcc ccgggtgtca aaagtgtcac cagctgtctg tgttagacaa    1740
ggttgccaag tgcaaaattg gttattacgg agggagagat ttgctccatt cattgttttt    1800
ttggaaggac aggacatgct gtctctagat ccagcaatag gtttgcttct gtaccccagc    1860
ctacccaagc agggactgga catccatcca gatagagggt agcataggaa tagggacagg    1920
agcatctgtt ctttaaggcc ttgtatggct gtttcctgtt gcatctggaa ctaactatat    1980
atattgtctt cagtgaagac tgattcaact ttgggtatag tggagccaaa gagattttta    2040
gctctgtatt tgcggtatcg gtttagaaga caaaaaaaat taaaacctga tacttttatc    2100
tgattattgt aaatatttga tcttcaatca cttgacagtg tttgtttggc ttgtatttgt    2160
ttttatcttt tgggcttaaa agagatccaa agagagaaag agcagtatgc cacttcttag    2220
aacaaaagta taaggaaaaa aatgttcttt ttaatccaaa gggtatattt gcagcatgct    2280
tgaccttgat gtaccaattc tgacggcatt ttcgtggata ttattatcac taagactttg    2340
ttatgatgag gtcttcagtc tctttcatat atcttccttg taacttttttt tttcctctta    2400
```

```
atgtagtttt gactctgcct tacctttgta aatatttggc ttacagtgtc tcaagggta    2460 ttttggaaag acaccaaaat tgtgggttca cttttttttt ttttttttaaa taacttcagc   2520 tgtgctaaac agcatattac ctctgtacaa aattcttcag ggagtgtcac ctcaaatgca   2580
atactttggg ttggtttctt tccttttaaa aaaaaatacg aaactggaag tgtgtgtatg   2640
tgtgcgagta tgagcgccca tttggtggat gcaacaggtt gagaggaagg gagaattaac   2700
ttgctccatg atgttcgtgg tgtaaagttt tgagctggaa tttattataa gaatgtaaaa   2760
ccttaaatta ttaataaata actattttgg ctattgaaaa aaaaaaaaaa aaaa          2814
```

<210> SEQ ID NO 3
<211> LENGTH: 11
<212> TYPE: PRT
<213> ORGANISM: Mus musculus

<400> SEQUENCE: 3

Arg Arg Leu Gln Lys Gly Asn Leu Pro Val Arg
1               5                   10

<210> SEQ ID NO 4
<211> LENGTH: 176
<212> TYPE: PRT
<213> ORGANISM: Mus musculus

<400> SEQUENCE: 4

Phe Pro Val Glu Ile Leu Pro Phe Leu Tyr Leu Gly Cys Ala Lys Asp
1               5                   10                  15

Ser Thr Asn Leu Asp Val Leu Glu Glu Phe Gly Ile Lys Tyr Ile Leu
            20                  25                  30

Asn Val Thr Pro Asn Leu Pro Asn Leu Phe Glu Asn Ala Gly Glu Phe
        35                  40                  45

Lys Tyr Lys Gln Ile Pro Ile Ser Asp His Trp Ser Gln Asn Leu Ser
    50                  55                  60

Gln Phe Phe Pro Glu Ala Ile Ser Phe Ile Asp Glu Ala Arg Gly Lys
65                  70                  75                  80

Asn Cys Gly Val Leu Val His Cys Leu Ala Gly Ile Ser Arg Ser Val
                85                  90                  95

Thr Val Thr Val Ala Tyr Leu Met Gln Lys Leu Asn Leu Ser Met Asn
            100                 105                 110

Asp Ala Tyr Asp Ile Val Lys Met Lys Lys Ser Asn Ile Ser Pro Asn
        115                 120                 125

Phe Asn Phe Met Gly Gln Leu Leu Asp Phe Glu Arg Thr Leu Gly Leu
    130                 135                 140

Ser Ser Pro Cys Asp Asn Arg Val Pro Thr Pro Gln Leu Tyr Phe Thr
145                 150                 155                 160

Thr Pro Ser Asn Gln Asn Val Tyr Gln Val Asp Ser Leu Gln Ser Thr
                165                 170                 175

<210> SEQ ID NO 5
<211> LENGTH: 23
<212> TYPE: DNA
<213> ORGANISM: Artificial Sequence
<220> FEATURE:
<223> OTHER INFORMATION: targeting exon 1 of dusp6 gene

<400> SEQUENCE: 5
gatcgccatt tccgacgcga agg                                            23

ANTI-OBESITY MICROBIOTA COMPOSITIONS AND PREPARATION METHODS AND USES THEREOF

RELATED APPLICATION

This application claims priority to U.S. Provisional Application No. 62/323,053, filed on Apr. 15, 2016, the content of which is hereby incorporated by reference in its entirety.

TECHNOLOGY FIELD

The present invention relates to microbiota compositions and their preparation methods and uses. Particularly, the present invention provides microbiota compositions collected from a dual-specificity phosphatase 6 (dusp6) deficient mammal, which is effective in altering a relative abundance of gut microbiota and also useful in reducing body weight, fat mass, and/or size of adipocytes and increasing oxygen consumption and/or energy expenditure and thus can be used to treat or prevent obesity or its associated disorders or conditions in a subject in need.

BACKGROUND OF THE INVENTION

Obesity is now a plague in developed countries as well as in many developing countries[40]. Since obesity increases the risk of many health conditions, including cardiovascular disease, stroke, type 2 diabetes, fatty liver and certain cancers[41], it is important to understand the detailed mechanism of obesity development and search for novel ways to treat obesity.

Dual-specificity phosphatases (DUSPs) are canonically characterized as negative regulators of the mitogen-activated protein kinase (MAPK) pathway[1,2]. Some studies have demonstrated that DUSP6, also known as MKP-3, negatively regulates ERK1/2 activity via dephosphorylation, although this dephosphorylation activity could be context-dependent[3,4]. Dusp6-deficient mice have been shown to have enlarged hearts and an increased resistance to some heart diseases[4]. Recently, it has been reported that dusp6 is upregulated in the liver of obese and diabetic mice and promotes glucose output in both cultured liver cells and mouse livers[5]. Furthermore, it has been shown that systemic dusp6 deficiency could significantly decrease blood glucose levels, improve insulin sensitivity and increase the resistance to diet-induced obesity (DIO)[6]. Besides host genetic and environmental factors, the gut microbiota has been recognized as a major regulator in the development of obesity[7-9]. However, whether or not dusp6-deficiency-mediated effects on obesity function via the gut microbiota remains unclear.

BRIEF SUMMARY OF THE INVENTION

The present invention is based on the unexpected finding that gut microbiota collected from a dual-specificity phosphatase 6 (dusp6) deficient mammal, when administrated into a subject, can change relevant abundance of microbiota in a gastrointestinal tract of the subject. It is also found in the present invention that the gut microbiota collected from a dusp6 deficient mammal exhibit anti-obesity activities, which are effective in reducing of body weight, fat mass, and/or size of adipocytes and increasing oxygen consumption and/or energy expenditure, and thus can be used to treat obesity or its associated disorders or conditions in a subject in need. The present invention also provides a platform technology to obtain microbiota from a dusp6 deficient mammal and identify/isolate anti-obesity microbes therefrom for treatment/prevention of obesity or its associated disorders or conditions.

In one aspect, the present invention provides a method for obtaining probiotic microbiota, comprising:
(a) providing a dusp6 deficient mammal; and
(b) collecting gut microbiota from the dusp6 deficient mammal.

In some embodiments, the method of the present invention further comprises culturing the gut microbiota to obtain culcurable microbiota.

In some embodiments, the method of the present invention further comprises measuring the gut microbiota's anti-obesity activity in a subject.

In some embodiments, the method of the present invention further comprises identifying lean-associated microbes from the gut microbiota.

In certain embodiments, the lean-associated microbes are identified by measuring whether the microbes are effective in reducing body weight, fat mass, and/or size of adipocytes in a subject upon administration of the microbes.

In certain embodiments, the lean-associated microbes are identified by measuring whether the microbes are effective in increasing oxygen consumption and/or energy expenditure in a subject upon administration of the microbes The gut microbiota profile from the dusp6 deficient mammal is further identified in the present invention.

Accordingly, the present invention also provides a composition, which comprises
(i) substantially purified Actinobacteria, (ii) substantially purified Bacteroidetes, (iii) substantially purified Cyanobacteria, (iv) substantially purified Deferribacteres, (v) substantially purified Firmicutes, (vi) substantially purified Proteobacteria, (vii) substantially purified TM7, (viii) substantially purified Tenericutes, and/or any combination thereof; and/or
(a) substantially purified Bacteroidaceae. (b) substantially purified S24-7, (b) substantially purified Rikenellaceae, (d) substantially purified Porphyromonadaceae, (e) substantially purified Odoribacteraceae, (f) substantially purified Ruminococcaceae, (g) substantially purified Erysipelotrichaceae, (h) Lachnospiraceae, (i) Lactobacillaceae, (j) Clostridiaceae, and/or any combination thereof.

In some embodiments, the composition of the invention comprises (iv) substantially purified Deferribacteres or (v) substantially purified Firmicutes, or a combination thereof.

In some embodiments, the composition of the invention comprises (f) substantially purified Ruminococcaceae or (h) Lachnospiraceae, or a combination thereof.

In certain embodiments, in the composition of the invention, (ii) substantially purified Bacteroidetes and (v) substantially purified Firmicutes are present in a ratio of about 1:1.2.

In certain embodiments, in the composition of the invention, (i) substantially purified Actinobacteria, (iv) substantially purified Deferribacteres and (vi) substantially purified Proteobacteria are present in a ratio of about 1:120:20.

In certain embodiments, in the composition of the invention, (i) substantially purified Actinobacteria, (ii) substantially purified Bacteroidetes, (iv) substantially purified Deferribacteres, (v) substantially purified Firmicutes, and (vi) substantially purified Proteobacteria are present in a ratio of about 1:1400:120:1770:20.

In certain embodiments, the composition of the invention is obtained from a dusp6 deficient mammal according to a method as described herein.

In some embodiments, the composition of the invention is formulated as a food product, dietary supplement or medicament.

In particular embodiments, the composition of the invention is for use in altering a relative abundance of microbiota in a subject.

In particular embodiments, the composition of the invention is for use in in reducing body weight and/or body fat, preventing an increase in body weight and/or body fat, and/or treating or preventing obesity or its associated disorders or conditions in a subject.

The present invention further provides a method of using a composition as described herein.

In particular, the present invention provides a method for altering a relative abundance of microbiota in a subject in need thereof by administering to the subject an effective amount of a composition as described herein. Also within the scope of the present invention is use of a composition as described herein for manufacturing a food product, dietary supplement or medicament for altering a relative abundance of microbiota in a subject in need thereof.

In some embodiments, the amount of the composition as used in the method of the invention is effective in decreasing a relative abundance of TM7 in the subject.

In some embodiments, the amount of the composition as used in the method of the invention is effective in decreasing a relative abundance of *Streptococcaceae* in the subject.

In some embodiments, the amount of the composition as used in the method of the invention is effective in increasing a relative abundance of *Escherichia, Parabacteroides* and/or *Lactobacillus* in the subject.

In some embodiments, the amount of the composition as used in the method of the invention is effective in increasing a relative abundance of Proteobacteria in the subject.

The present invention also provides a method for reducing body weight and/or body fat and/or preventing an increase in body weight and/or body fat in a subject in need thereof by administering to the subject an effective amount of a composition as described herein. The present invention also further provides a method for treating or preventing obesity or its associated disorders or conditions in a subject in need thereof by administering to the subject an effective amount of a composition as described herein. Also within the scope of the present invention is use of a composition as described herein for manufacturing a food product, dietary supplement or medicament for reducing body weight and/or body fat, preventing an increase in body weight, and/or body fat and/or treating or preventing obesity or its associated disorders or conditions in a subject in need thereof.

In some embodiments, the obesity to be treated is diet induced obesity (DIO).

In some embodiments, the obesity associated disorders or conditions are selected from the group consisting of type 2 diabetes, hyperglycemia, glucose intolerance, dyslipidemia, insulin resistance, hyperinsulinemia, fatty liver, cardiovascular disease, stroke, and cancer.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

Figure 4:
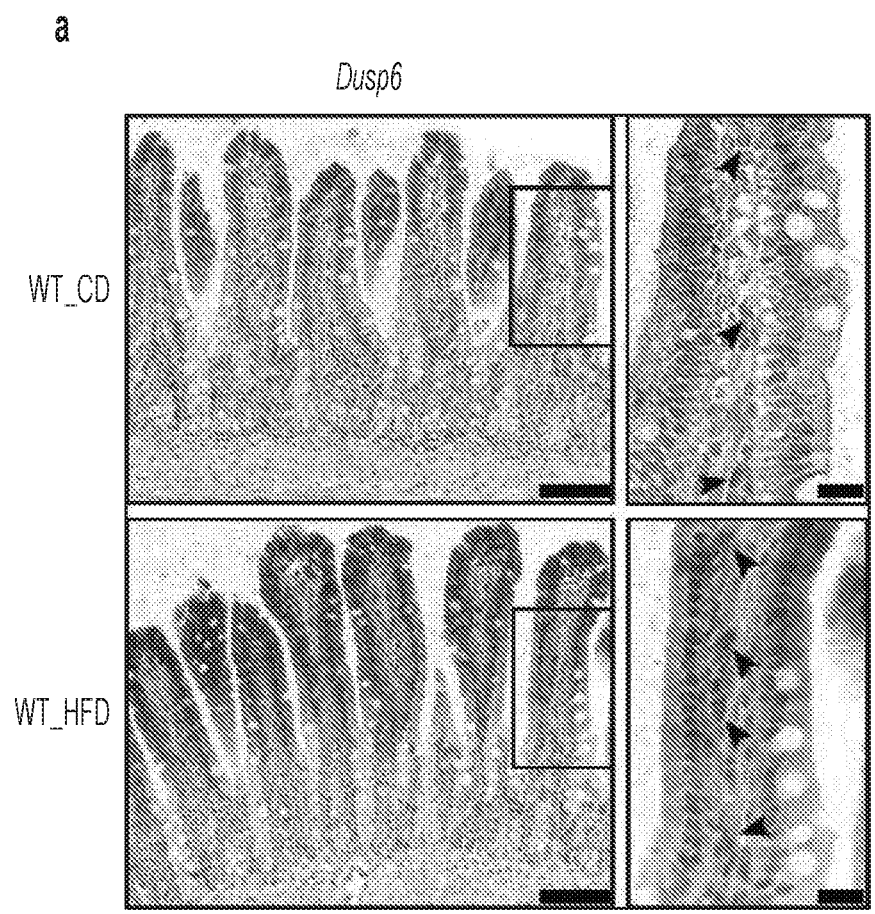

FIG. 4 shows that intestine transcriptome analysis of dusp6-deficient and WT mice. a, Left: Immuno-histochemistry analysis of DUSP6 protein in WT mouse intestine after 16 weeks of CD or HFD treatment. Scale bars, 100 μm. Right: Zoomed images of the areas indicated in the left panels. Arrows indicate DUSP6-expressed intra-epithelial immune cells. Scale bars, 20 μm. b,c, Validations (from qRT-PCR) of the KEGG Ppar pathway and TJ pathway that were significantly enriched in the upregulated genes of the comparison of dusp6-deficient mice to WT mice in CD. N=5 mice for each group. Data are presented as mean±s.e.m. NS, statistically non-significant; *P<0.05 according to Mann-Whitney analysis.

Figure 5:
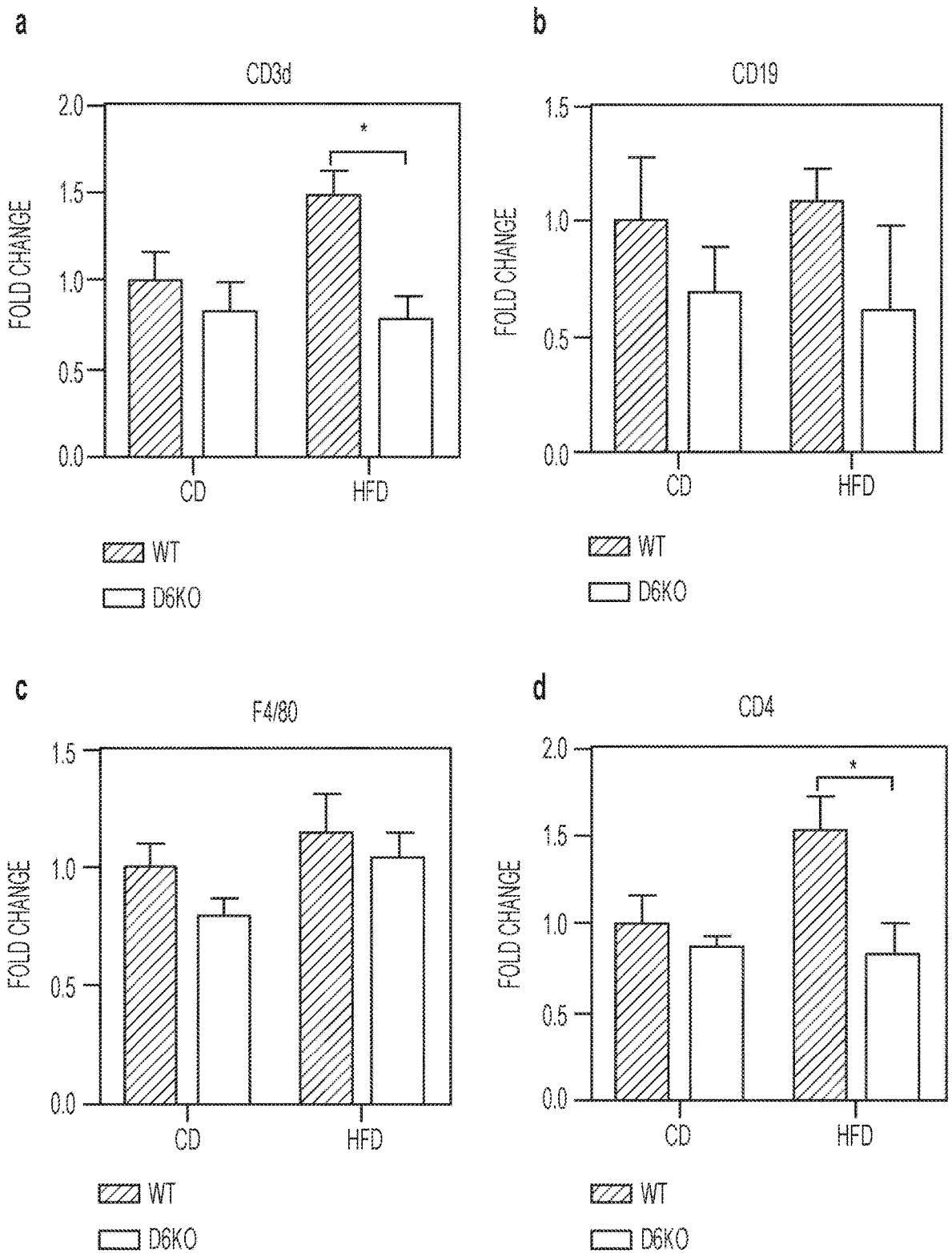

FIG. 5 shows that dusp6 deficiency modulates intestinal mucosal immunity to adapt HFD challenging. a-d, Analysis of CD3d (a), CD19 (b), F4/80 (c) and CD4 (d) in mouse intestine of each representative treatment using qRTPCR. Data are presented as the mean±s.e.m. Number of mice for each group: WT-CD, N=9; WT-HFD, N=9; D6KO-CD, N=7; D6KO-HFD, N=6. *P<0.05, according to one-way ANOVA analysis and Tukey's post-hoc test. e-f, IHC analysis of CD3 (e) and CD4 (f) T-cell marker protein in WT and D6KO mouse intestine after 16 weeks of CD or HFD treatment. Magnification, ×200. Scale bars, 200 μm.

Figure 6:
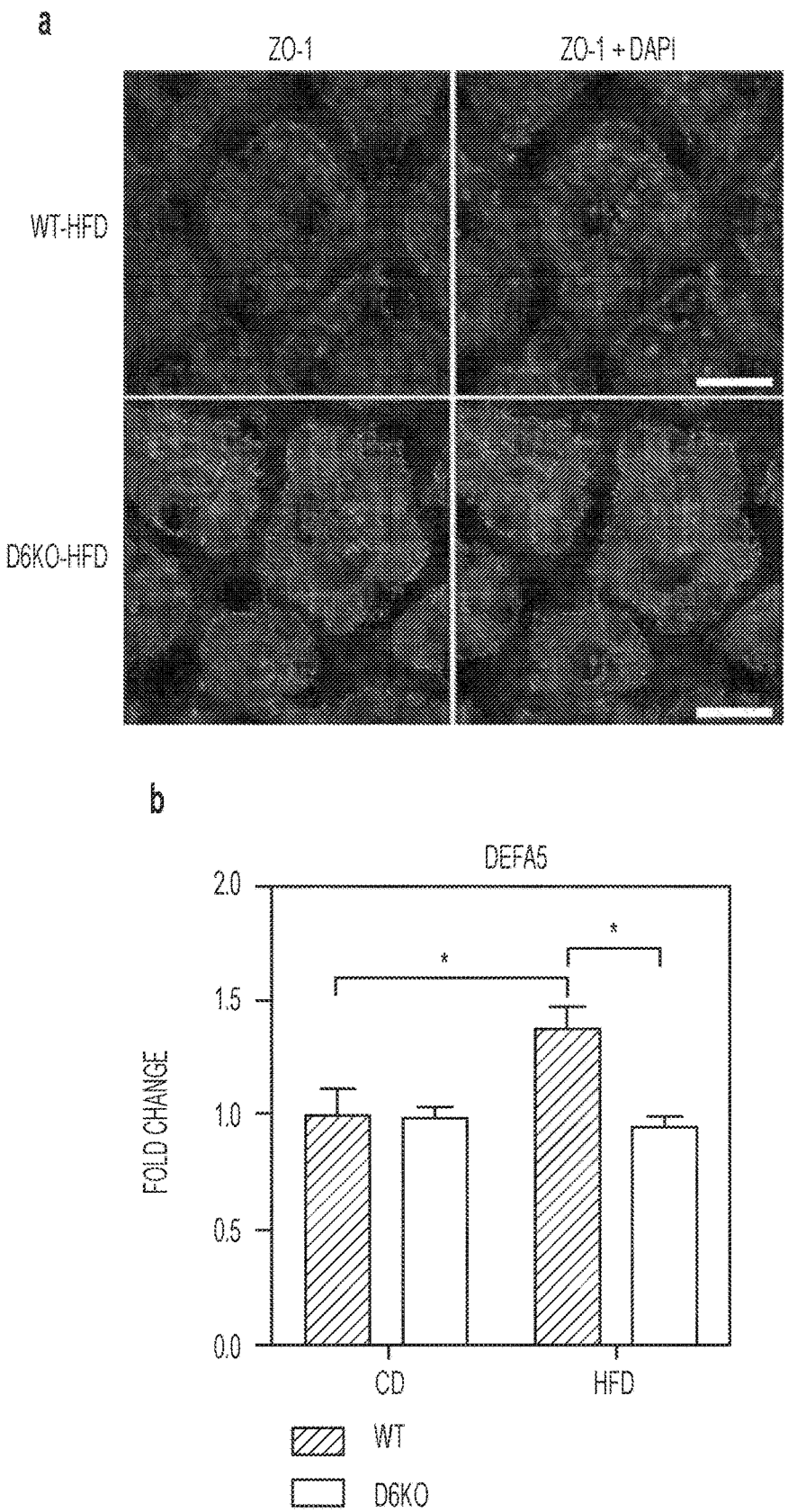

FIG. 6 shows that dusp6 deficiency confers HFD-specific modulation to maintain physiological barrier function. a, Fluorescent IHC analysis of ZO-1 protein of HFD-fed WT and dusp6-deficient mice. Scale bars, 50 μm. b, Analysis of the intestinal Defa5 gene of WT/dusp6-deficient mice before and after HFD treatment using qRT-PCR. Number of mice for each group: WT-CD, N=10; WT-HFD, N=9; D6KO-CD, N=8; D6KO-HFD, N=7. Data are presented as mean±s.e.m. *P<0.05, according to one-way ANOVA analysis and Tukey's post-hoc test. c, Validation of 16S rRNA gene of segmented filamentous bacteria (SFB) before and after 16 weeks of HFD treatment using qPCR. The SFB plasmid CTLS-6 was used as a standard to validate the absolute copy number of each sample. Number of mice for each group: before HFD treatment: WT, N=18 and D6KO, N=17; after 16 weeks of HFD treatment: WT, N=8 and D6KO, N=7. The middle lines indicate the mean of each group. *P<0.05, according to Mann-Whitney analysis. d, Graphical summary of the potential roles of dusp6 deficiency in regulating microbiota response and obesity resistance.

Figure 7:
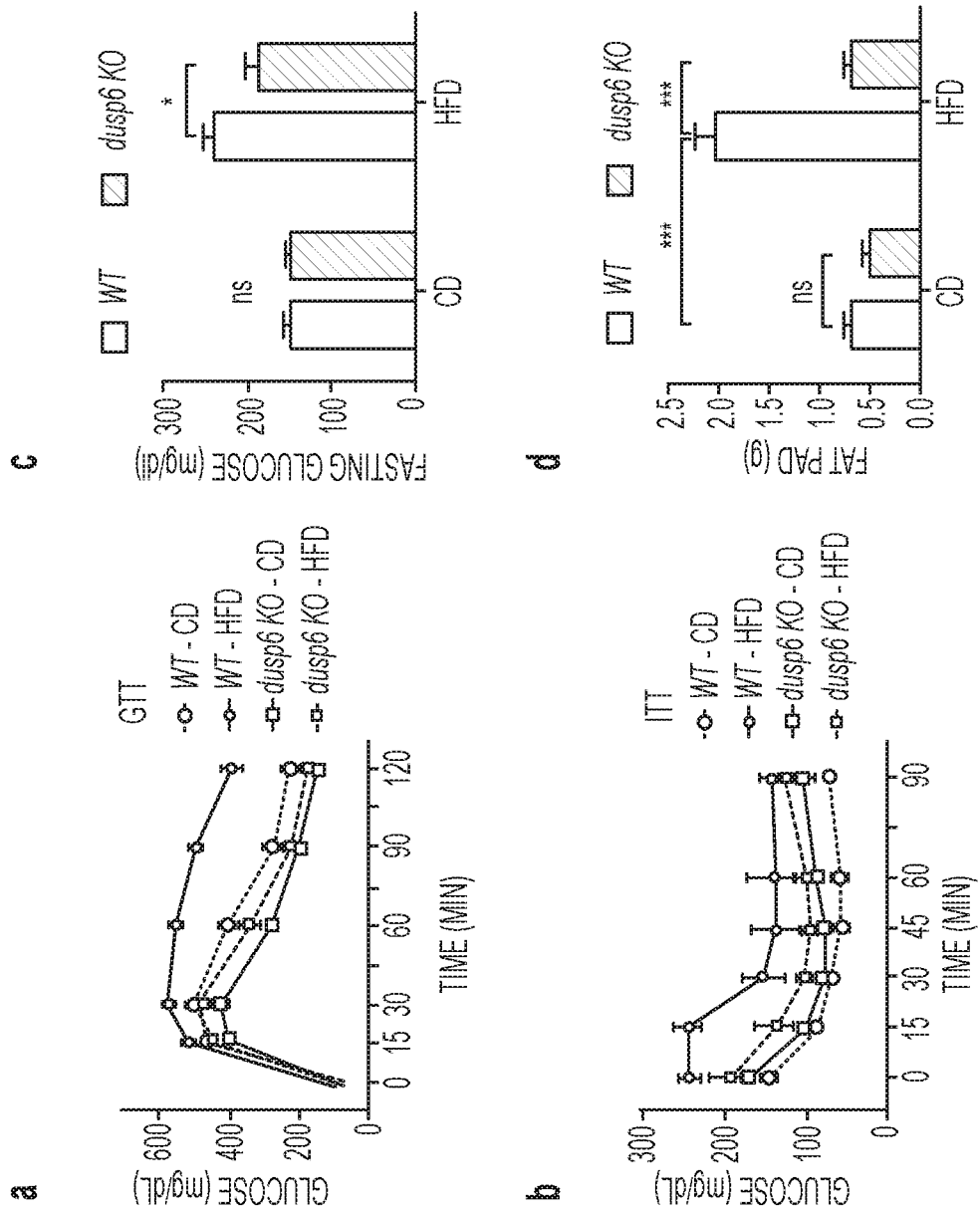

FIG. 7 shows that dusp6-deficiency increased glucose tolerance and alleviated obesity-associated phenotypes in mice. a, Glucose tolerance test after 12 hours fasting of male WT/dusp6 KO mice were fed on CD or HFD for 16 weeks. Data are presented as the mean±SEM of each time point. WT-CD, N=17; WT-HFD, N=15; dusp6 KO-CD, N=17; dusp6 KO-HFD, N=13. b, Insulin tolerance test after 6 hours fasting of male WT/dusp6-KO mice were fed on CD or HFD for 16 weeks. Data are presented as the mean±SEM of each time point. WT-CD, N=7; WT-HFD, N=7; dusp6 KO-CD, N=5; dusp6 KO-HFD, N=5. c, Blood glucose level after 6 hours fasting of male WT/dusp6-KO mice fed on CD or HFD for 16 weeks. Data are presented as the mean±SEM. WT-CD, N=7; WT-HFD, N=7; dusp6 KO-CD, N=7; dusp6 KO-HFD, N=6. d, Weight of flank adipose tissue of male WT/dusp6-KO mice fed on CD or HFD for 16 weeks. Data are presented as the mean±SEM. WT-CD, N=10; WT-HFD, N=8; dusp6 KO-CD, N=9; dusp6 KO-HFD, N=7. For (c) and (d), asterisks indicate statistical difference (*P<0.05, ***P<0.0005) according to One-Way ANOVA analysis and Tukey post-hoc test. e-f, Haematoxylin & eosin (H&E)-stained sections of flank adipose tissue (e) and liver tissue (f) from male WT and dusp6-KO mice fed on CD or high-fat diet HFD for 16 weeks. Scale bar, 100 μm.

Figure 8:
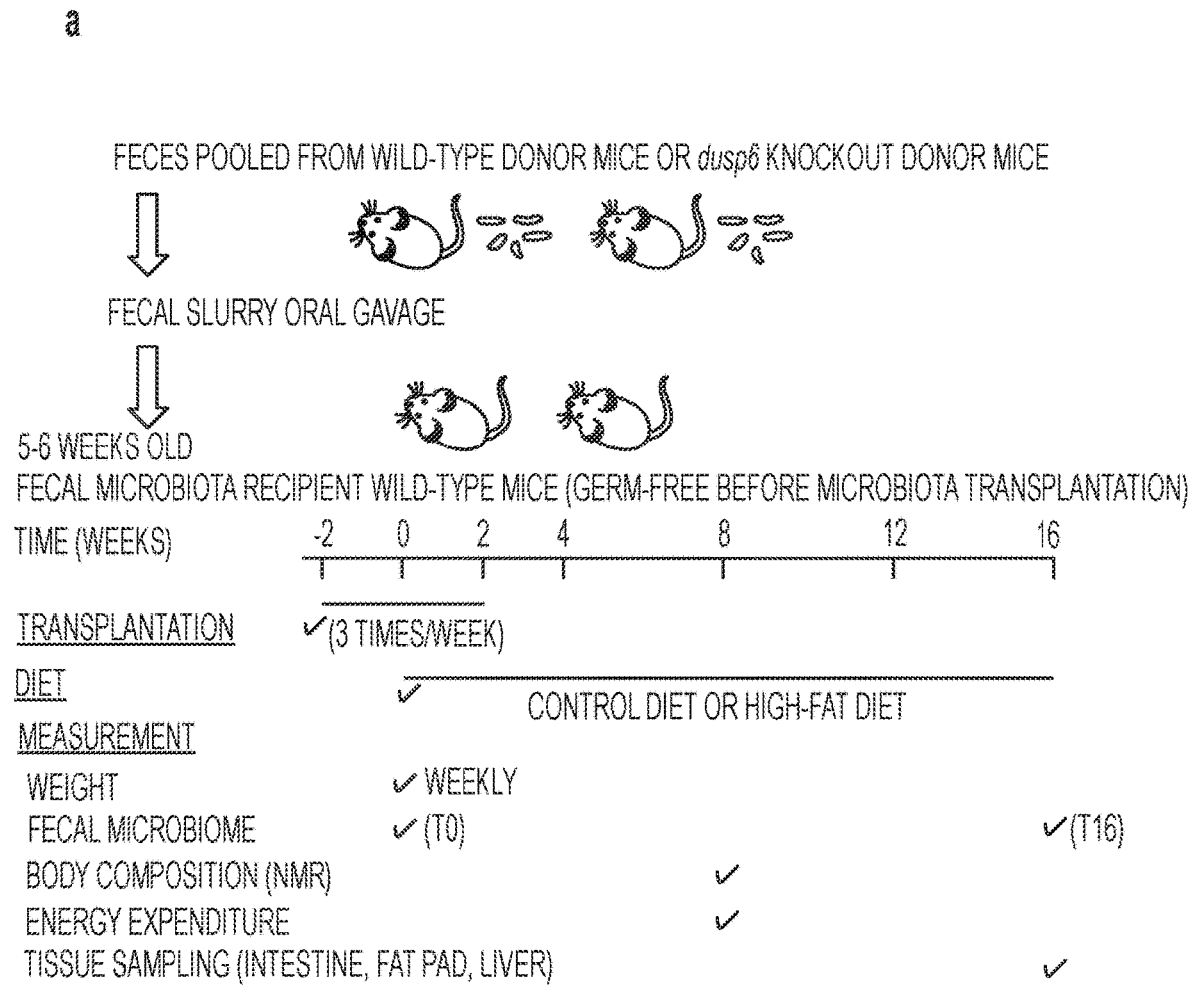

FIG. 8 shows that fecal/gut microbiome composition of FMT recipient mice. a, Schematic diagram of fecal microbiome transplantation, metabolic tests and tissue sampling of WT/D6KO microbiota recipient mice. b, Quantitative PCR validation of 16S rRNA gene of all eubacteria before and after 16 weeks of HFD treatment. The plasmid contained 16S rRNA sequence of Eubacteria was used as the standard to validate the absolute copy number of each sample. The number of mice for each group: before HFD treatment, WT, N=18 and dusp6KO, N=17; after 16 weeks of HFD treatment, WT, N=8 and dusp6KO, N=7. The middle line indicates the mean of each group. Double asterisks and triple asterisks indicate statistical difference (P<0.005 and P<0.0005) of mean±SEM according to Mann-Whitney analysis. c-d, Weighted-UniFrac (c) and Unweighted-UniFrac (d) Principle coordinates analysis (PCoA) plot represents changes between chow diet (T0) and HFD (T16) fed wild-type and dusp6 knockout mice. The number of mice per group: T0: WT-CD, N=11; dusp6 KO-CD, N=13; T16: WT-HFD, N=6; dusp6 KO-HFD, N=6. e, Composition of Firmicutes family of WT/dusp6 KO microbiota recipient mice before and after 16 weeks of HFD treatment. f, Composition of Proteobacteria family of WT/dusp6 KO microbiota recipient mice before and after 16 weeks of HFD treatment. g, LDA scores of the differentially abundant microbial clades (with LDA score>2 and significance of α<0.1 determined by Kruskal-Wallis test). h, 5-6 weeks old male germ-free mice were oral gavaged with BHI broth culture of fecal microbiota derived from representative donors and then fed on HFD for 16 weeks. Body weights were monitored weekly. Data are presented as the mean±SEM of each time point. CFMT-WT, N=11; CFMT-dusp6 KO, N=12. i, Weight gain of WT/dusp6 KO CFMT recipient mice after 16 weeks of HFD treatment. Data are presented as the mean±SEM. The asterisk indicates statistical difference (P<0.05) according to Mann-Whitney analysis. CFMT-WT, N=11; CFMT-dusp6 KO, N=12.

Figure 9:
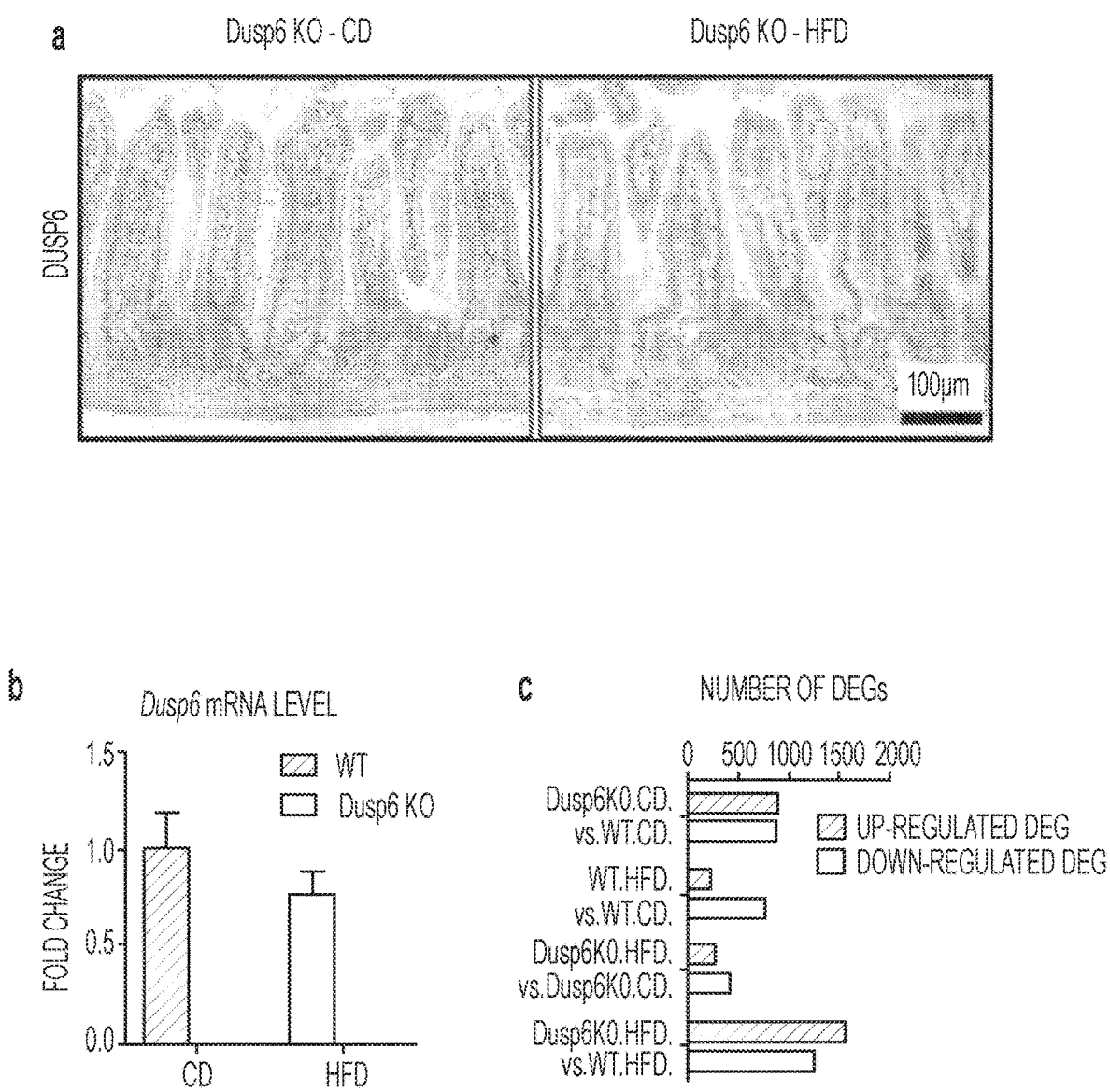

FIG. 9 shows that transcriptome profile of CD or HFD treated WT/dusp6-KO mice. a-b, Immuno-histochemistry analysis (a) and qRT-PCR analysis (b) of DUSP6 protein or dusp6 gene expression in intestine of chow diet of HFD fed dusp6 KO mice. Scale bar, 100 μm. c, The number of overall DEGs (c) that were significantly enriched among up-regulated genes or down-regulated genes in the comparisons of HFD-fed WT and dusp6-KO mice. d, Immunoblot analysis of DUSP6 protein in WT and DUSP6 KO Caco-2 cells. e, TEER analysis of WT and DUSP6 KO Caco-2 cells after 21 days of differentiation. Data are presented as the mean±SEM (N=3 separate experiments). The asterisk indicates statistical difference (P<0.05) according to two-tailed t-test. f, 2 hours after oral gavaged with FITC conjugated 4 kDa dextran, mouse serum was collected for fluorescence measurement. Data are presented as the mean±SEM. N=11 for each group. The asterisk indicates statistical difference (P<0.05) according to Mann-Whitney analysis. g-h, qRT-PCR validations of the KEGG Ppar pathway (g) and tight junction pathway (h) that were significantly enriched in the up-regulated genes of the comparison of dusp6-deficient mice to wild-type mice in control diet in CD fed FMT recipient mice. Data are presented as the mean±SEM. N=8 for FMT-WT recipient mice and N=7 for FMT-Dusp6 KO recipient mice. The asterisk indicates statistical difference (P<0.05) according to Mann-Whitney analysis. Ns indicates statistically non-significant.

Figure 10:
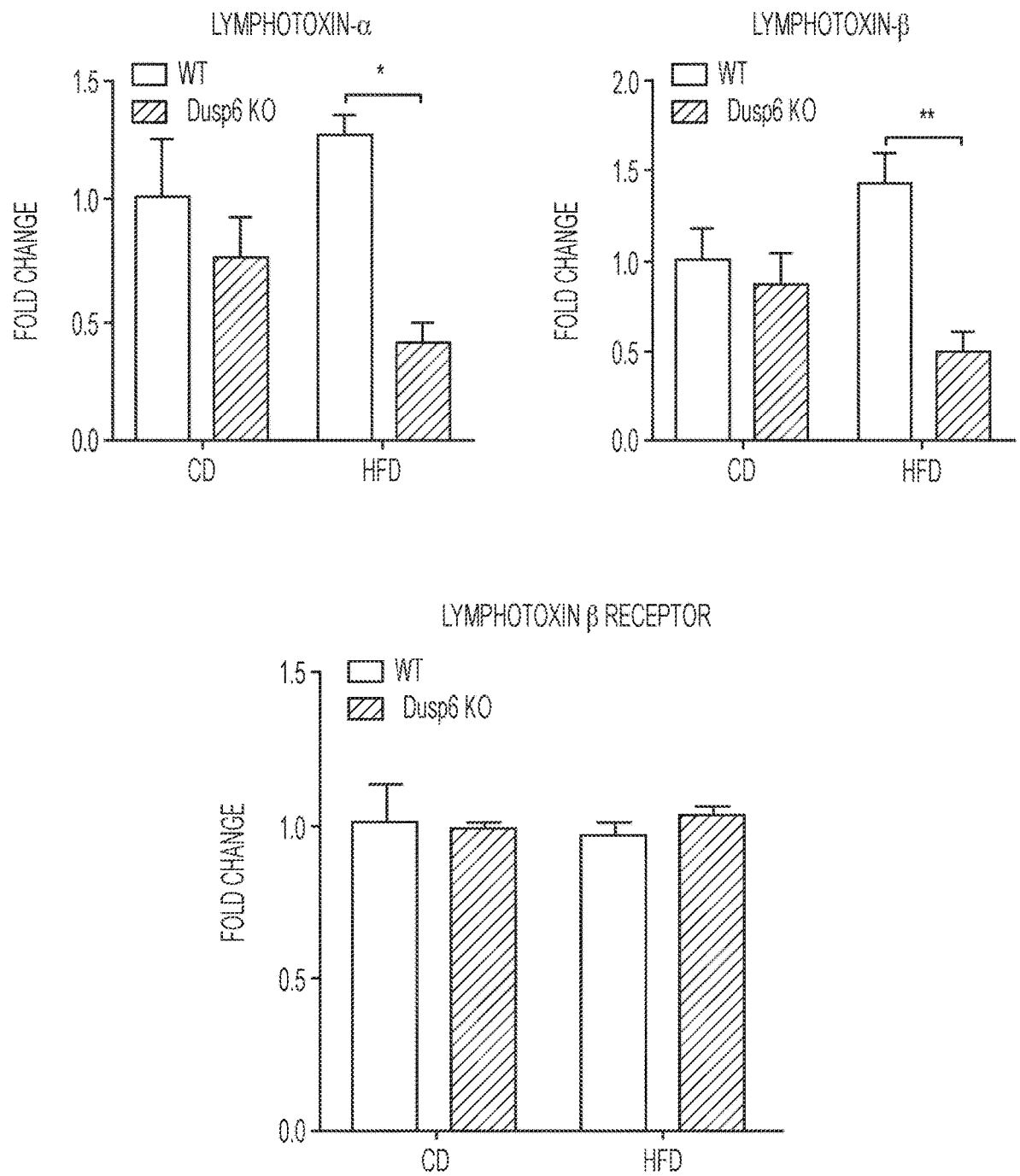

FIG. 10 shows that KEGG immunological pathways down-regulated in HFD-fed dusp6-deficient mice. qRT-PCR analysis of Ltα, Ltβ and LTβR of WT and dusp6-deficient mice before and after HFD treatment. Data are presented as the mean±SEM. Asterisk (P<0.05) and double asterisks (P<0.005) indicate statistical difference according to One-Way ANOVA analysis and Tukey post-hoc test. The number of mice for each group: WT-CD, N=7; WT-HFD, N=8; Dusp6KO-CD, N=7; Dusp6KO-HFD, N=8.

Figure 11:
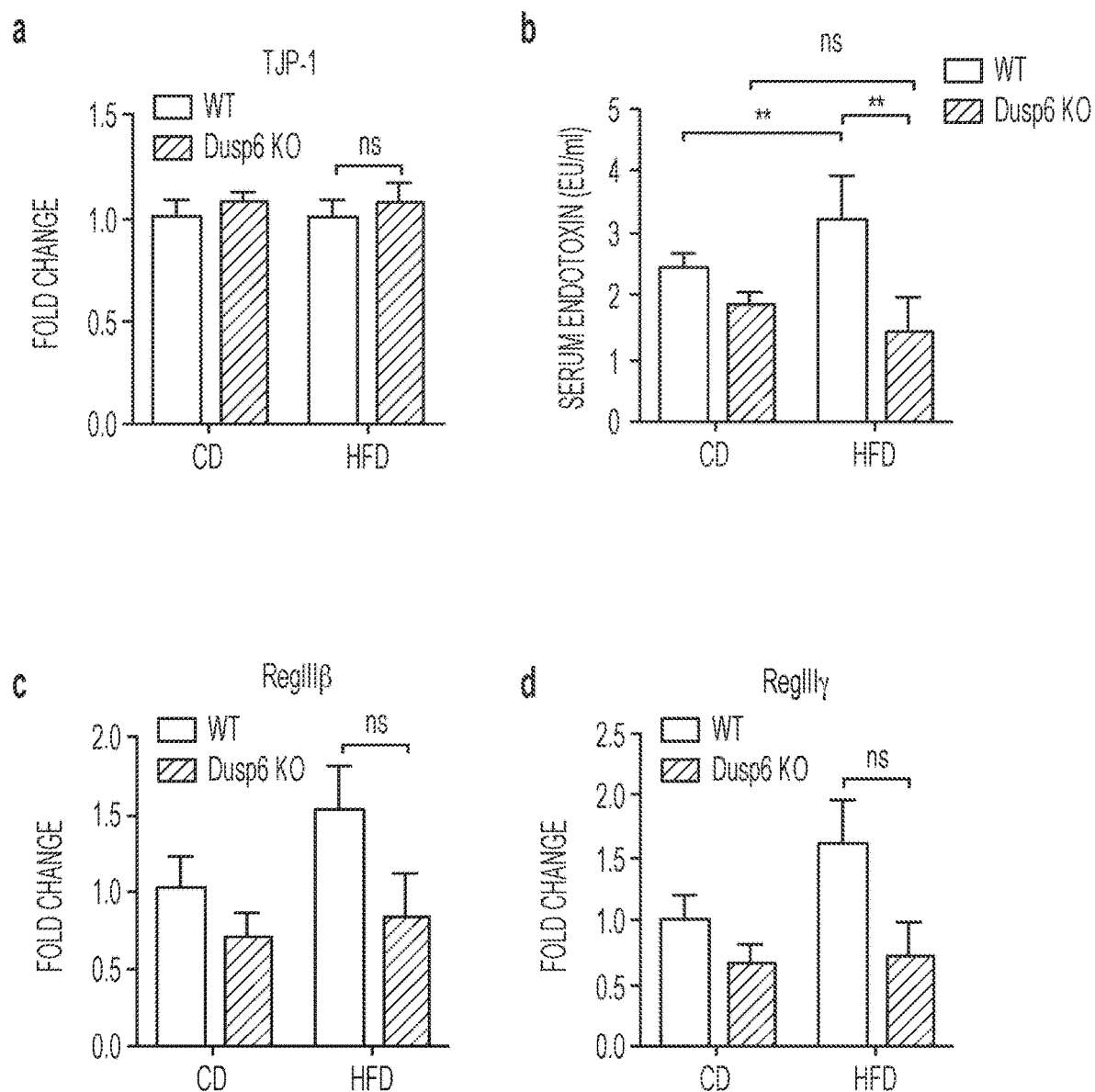

FIG. 11 shows that dusp6-deficiency reversed HFD-mediated induction of intestinal antimicrobial peptides (AMPs). a, qRT-PCR analysis of intestinal TJP-1 gene of WT/dusp6-deficient mice before and after HFD treatment. Data are presented as the mean±SEM. ns indicates statistical non-significant according to One-Way ANOVA analysis and Tukey post-hoc test. N=5 for each group. b, Serum endotoxin levels of WT/dusp6-deficient mice before and after HFD treatment were determined by LAL test. Data are presented as mean±SEM. Double asterisks indicate statistical difference (P<0.005) according to One-Way ANOVA analysis and Tukey post-hoc test. The number of mice for each group: WT-CD, N=9; WT-HFD, N=13; Dusp6KO-CD, N=9; Dusp6KO-HFD, N=13. c-d, Quantitative RT-PCR validation of RegIIIβ (c) and RegIIIγ (d). Data are presented as the mean±SEM. The number of mice for each group: WT-CD, N=10; WT-HFD, N=8; Dusp6 KO-CD, N=9; Dusp6 KO-HFD, N=7. ns indicates statistically non-significant according to One-Way ANOVA analysis and Tukey post-hoc test.

DETAILED DESCRIPTION OF THE INVENTION

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

As used herein, the term "about" refers to a range of values+10% of a specified value.

I. A Dual-Specificity Phosphatase 6 (Dusp6) Deficient Animal

In the present invention, a dusp6 deficient animal is provided as a model or platform for providing probiotic microbiota.

As used herein, the term "microbiota" refers to one or more microbial communities or groups of microorganisms which can be found or can be present (colonize) in a location of the body. In particular, microbiota as described herein includes bacterial groups and more particular gut bacterial groups that are found within a gastrointestinal tract of a mammal. Microbiota, as used herein, may be of the same type or may be a mixture of different types (e.g. phylum, class, order, family, genus, species, strain) of microorganisms. In particular, the microbiota disclosed can be probiotic microbiota, which includes probiotic, non-pathogenic bacteria that can confer a health benefit to the host (e.g., altering the gut microbiota profile and/or providing anti-obesity effects).

As used herein, the term "animal" includes mammals, particularly non-human mammals. In some embodiments, the animal is a rodent (e.g., mouse, rat, chipmunk, prairie dog, squirrel, beaver, gopher, hamsters, voles, gerbils, porcupines, guinea pigs, etc.) In some embodiments, the animal is a livestock animal (e.g., pigs, cattle, goats, deer, sheep, yaks, etc.). In some embodiments, the animal is a companion animal (e.g., cat, dog, etc.). In some embodiments, the animal is a primate (e.g., lemurs, monkeys, apes, etc.).

As used herein, dual specificity phosphatase (dusp6), also known as MKP3, is a mitogen-activated protein kinase (MAPK) phosphatase, which negatively regulates ERK1/2 activity via dephosphorylation. In particular, dusp6 is a polypeptide containing about 381 amino acids and has the molecular weight of about 40 kDa. Dusp6 possesses a linker region between its N-terminal MAPK-binding domain and its C-terminal catalytic domain, which is highly conserved in related DUSPs. The amino acid sequences of dusp6 of various species are well known in the art. For example, in mice, an exemplary dusp6 is as set forth in SEQ ID NO: 1, where its N-terminal MAPK-binding domain from positions 64 to 74 (SEQ ID NO: 3) and its C-terminal catalytic domain from positions 206 to 381 (SEQ ID NO: 4); the corresponding nucleotide sequence encoding the mouse dusp6 is SEQ ID NO: 2. Dusp6 as described herein can also include a polypeptide containing an amino acid sequence highly identical to the amino acid sequence of SEQ ID NO: 2 and in particular contains an amino acid sequence highly identical to the C-terminal catalytic domain of SEQ ID NO: 2 and having substantially the same phosphatase catalytic activity. The phosphatase catalytic activity can be determined by methods known in the art e.g. a fluorometric assay or a luminescent measurement.

As used herein, the term "protein" or "polypeptide" refers to a polymer composed of amino acid residues linked via peptide bonds, for example, containing about 2,000 or less, 1,000 or less, 500 or less, 400 or less. Amino acids can be expressed by three letters or one letter as known in the art.

As used herein, the term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." A "gene" refers to a polynucleotide containing at least one open reading frame (ORF) that is capable of encoding a particular polypeptide or protein after being transcribed and translated. The term "encoding" refers to the inherent property of specific nucleotide sequences in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence or a gene encoding an amino acid sequence" includes all nucleotide sequences that are degenerate versions of each other and that encode the same amino acid sequence. Nucleotide sequences that encode proteins and RNA may include introns.

As used herein, the phrase "a gene encoding dusp6 or a gene homologous to the gene" can include a gene encoding a polypeptide containing the amino acid sequence of SEQ ID NO: 1, a polymorphic gene of the gene in the same species, or a gene encoding a polypeptide having the same phosphatase activity as the polypeptide that is conserved across the species. It also includes a naturally-occurring DNA which is highly identical to the nucleotide sequence of SEQ ID NO: 2 and that contains a nucleotide sequence encoding a phosphatase; or a naturally-occurring DNA encoding a polypeptide that contains an amino acid sequence highly identical to the amino acid sequence of SEQ ID NO: 2 and in particular contains an amino acid sequence highly identical to the C-terminal catalytic domain of SEQ ID NO: 2 and having substantially the same phosphatase catalytic activity.

As used herein, the term "highly identical" refers to sequence identity of, for example, 70% or more, preferably 80% or more, 85% or more, 90% or more, and most preferably 95% or more (for example, 96%, 97%, 98%, or 99% or more). To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

As used herein, "a dusp6 deficient animal" means an animal that is deficient in functional dusp6. The term "functional dusp6" refers to dusp6 that retains its phosphatase activity as above-described. Deficiency in functional dusp6 can mean substantial loss or absence of dusp6 which is normally observed in intestinal epithelium and/or intra-epithelium immune cells and can be determined by conventional assays such as immunostaining, quantitative reverse transcription (qRT) polymer chain reaction (PCR) analysis. "Substantial loss or absence" refers to particularly 50% or less, 25% or less, 10% or less, 5% or less, of the amount of dusp6 detected in the wild-type intestinal epithelium and/or intra-epithelium immune cells, and even particularly to an amount that is below the detection limit (or background level).

Deficiency in functional dusp6 in an animal can be achieved by targeted disruption of the animal's corresponding dusp6 gene. Targeted disruption can mean a technique for introducing a mutation into a target gene that involves introducing into cells a DNA in which a mutation has been introduced into the nucleotide sequence of the target gene, preferably a DNA into which a selection marker has been inserted, and more preferably a DNA into which a drug resistance gene has been inserted; and selecting cells in which homologous recombination has occurred between the introduced DNA and the target gene. More specifically, when a gene encoding dusp6 is deleted by targeted disruption, whole or a portion of the gene is replaced with an exogenous nucleic acid used for targeted disruption. The exogenous nucleic acid may simply be a sequence derived from a genome from which a gene encoding dusp6 has been deleted, or may contain a desired sequence. For example, the nucleic acid may contain a desired marker gene, preferably a drug resistance gene.

In particular, targeting vectors can be used to disrupt a gene encoding dusp6. The targeting vectors contain a portion of a DNA encoding dusp6 and contain a DNA in which the genetic sequence has been altered by deletion, addition, substitution or the like so as to prevent expression of functional dusp6. Preferably, the targeting vectors for a gene encoding dusp6 contain an exogenous nucleic acid, preferably a desired marker gene, and preferably a drug resistance gene, in a portion of a DNA encoding dusp6. More preferably, the targeting vectors contain a negative marker, such as the thymidine kinase gene or diphtheria toxin gene.

According to the present invention, targeting vectors can be used to produce dusp6 knockout animals. The term "gene knockout" as used herein, refers to the targeted disruption of a gene in vivo with complete loss of function that has been achieved by any transgenic technology known in the art. In one embodiment, transgenic animals having gene knockouts are those in which the target gene has been rendered nonfunctional by an insertion targeted to the gene to be rendered non-functional by homologous recombination.

Briefly, the targeting vectors are cleaved with a proper restriction enzyme to obtain a linear DNA, purified and then transfected into embryonic stem cells (ES cells) such as TT2 ES cells generated from (C57BL/6). Transfection methods include, but are not limited to, electroporation and lipofection. The transfected cells are then cultured in any suitable selective medium. For example, when a targeting vector is constructed to incorporate the neomycin resistance gene and thymidine kinase gene, cells are cultured in a selective medium containing neomycin and ganciclovir. Incorporation of an introduced gene, such as the neomycin resistance gene, into the ES cells that show resistance to both drugs and proliferate can be easily confirmed by PCR. Further, whether or not homologous recombination has occurred can be confirmed by Southern blot analysis, using as a probe a portion of the DNA of the 5' side upstream or the 3' side downstream outside the targeting vector. In addition, Southern blot analysis can be used to confirm that the targeting vector has not been randomly inserted, for example, using as a probe a DNA within the targeting vector. ES cells that have undergone homologous recombination can be acquired by combining these methods. Subsequently, knockout mice can be produced through the following steps: collecting 8-cell stage embryos or blastocysts after fertilization; microinjecting with ES cells where homologous recombination has occurred; transplanting the manipulated eggs into pseudopregnant mice; allowing the pseudopregnant mice to deliver and raising the offspring; selecting transgenic mice by PCR and Southern blotting; and establishing a mouse strain having the transgene.

Alternatively, deficiency in functional dusp6 in an animal can be achieved by using dusp6 antagonists. As used herein, the term "dusp6 antagonist" refers to a substance or an agent which can substantially reduce, inhibit or block the function of dusp6 e.g. its phosphatase activity. Dusp6 antagonists for use in generating a dusp6 deficient animal as described herein may include an anti-dusp6 antibody, an anti-sense nucleic acid molecule directed to a dusp6 gene, a small interfering RNA (siRNA) directed toward a dusp6 nucleic acid, or a small molecule dusp6 inhibitory compound.

An anti-dusp6 antibody is an antibody capable of binding to dusp6 and inhibits dusp6 biological activity. The term "antibody" encompasses not only intact (e.g., full-length) polyclonal or monoclonal antibodies, but also antigen-binding fragments thereof (such as Fab, Fab', F(ab')$_2$ and Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Antibodies described herein may be either monoclonal or polyclonal. Antibodies can be made by the conventional technology. For example, monoclonal antibodies may be prepared by the hybridoma methodology, or may be made using recombinant DNA methods in bacterial, eukaryotic animal or plant cells. Monoclonal antibodies may also be isolated from phage antibody libraries.

In some embodiments, dusp6 antagonists can be an antisense nucleic acid molecule capable of blocking or decreasing the expression of a functional dusp6. Nucleotide sequences of dusp6 genes are known and are readily available from publicly available databases. It is routine to prepare antisense oligonucleotide molecules that will specifically bind a target mRNA without cross-reacting with other polynucleotides. Exemplary sites of targeting can be the initiation codon, the 5' regulatory regions, the coding sequence and the 3' untranslated region. In some examples, the oligonucleotides are about 10 to 100 nucleotides in length, about 20 to 50 nucleotides in length, or about 15 to 30 nucleotides in length.

In some embodiments, dusp6 expression can be decreased using small interfering RNA (siRNA or RNAi) or microRNA or ribozymes, methods of which are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. A siRNA can be a double-stranded nucleic acid molecule comprising two nucleotide strands, each strand having about 19 to about 28 nucleotides. A short hairpin RNA (shRNA) is a sequence of RNA that makes a tight hairpin turn that can be used to silence gene expression via RNA interference. It is typical to use a vector to introduce shRNA into cells and to use a promoter (e.g., the U6 promoter) to ensure that the shRNA is expressed. The shRNA hairpin structure is cleaved by the cellular machinery into siRNA, which is then bound to the RNA-induced silencing complex (RISC). This complex binds to and cleaves mRNAs which match the siRNA that is bound to it. MicroRNAs (miRNAs) are a class of endogenous, single or double-stranded, about 22 nucleotide-long RNA molecules that regulate as much as about 30% of mammalian genes, with important roles in regulation of cellular differentiation, proliferation, and apoptosis. Specific patterns of up- and down-regulation of miRNAs in various human tumor types are recognized. miRNA represses protein production by blocking translation or causing transcript degradation.

In some embodiments, a dusp6 antagonist can be a dusp6 inhibitory compound. Ddusp6 inhibitory compound, as used herein, can be a compound other than antibodies or nucleic acids, which can reduce, inhibit or block the function of dusp6, by acting within the phosphatase domain to prevent the catalytic stimulation of phosphatase activity, for example. Dusp6 inhibitory compound can have a molecular weight of about any of 100 to 20,000 daltons, 150 to 10,000 daltons, or 250 to 500 daltons. Typical examples of a dusp6 inhibitory compound include (E)-2-benzylidene-3-(cyclohexylamino)-2,3-dihydro-1H-inden-1-one (BCI).

II. Features of a Dusp6 Deficient Animal

A dusp6 deficient animal according to the present invention exhibits one more features as compared wild-type animals.

Resistance to Obesity

Dusp6 deficient animal exhibits resistance to obesity, especially diet induced obesity.

It is found that a dusp6 deficient animal exhibits reduced body weight, attenuated fat pad mass, reduced adipocyte size, and attenuated symptoms of hepatosteatosis, induced by high-fat diet. It is also found that a dusp6 deficient animal shows a higher food intake then wild type. Therefore, it is suggested that dusp6 deficient does not protect mice from diet induced obesity via a decrease in food consumption.

Changes in Gut Microbiota Profile

Dusp6 deficient animal exhibits changes in gut microbiota profile. In particular, a relative abundance of one or more microbiota is altered either when the animal is fed with a low-fat diet or when the animal received high-fat diet (HFD) treatment.

As used herein, a high-fat diet (HFD) is a diet which is rich in fat content or calories coming out of fat portion of the diet. In one example, a high fat diet contains 40% or more calories from fat. A low-fat diet refers to a diet that provides less than 40%, particularly between 10% to 40% of total calories from fat, such as no more than 40%, 30%, 25%, 15% or 10% of total calories from fat. It will be appreciated that this range can vary for example depending upon the animal.

Altering microbiota can include changing a relative abundance of microbiota by increasing and/or decreasing the relative abundance of one or more microbiota. As used herein, the term "relative abundance" refers to the commonality or rarity of a microorganism relative to other microorganisms in a defined location or community. For example, the relative abundance can be determined by generally measuring the presence of a particular microorganism compared to the total presence of microorganisms in a sample. As used herein, the "total abundance" refers generally to the total microorganisms in a sample. As used herein, "microbiota profile" refers to a representation, such as a graph, of the relative abundance of one or more microbiota in a subject or sample from a subject. The relative abundance of microbiota can be measured for example by culture based methods (direct measurement), or comparing the prevalence of a molecular indicator of identity, such as ribosomal RNA (rRNA) gene sequences, specific for an organism or group of organisms in relation to the overall sample (indirect measurement). For example, a ratio of rRNA specific for Actinobacteria, Bacteroidetes, Cyanobacteria, Deferribacteres, Firmicutes, Proteobacteria, TM7, or Tenericutes in a total number of rRNA gene sequences obtained from a faeces sample can be used to determine the relative abundance of Actinobacteria, Bacteroidetes, Cyanobacteria, Deferribacteres, Firmicutes, Proteobacteria, TM7, or Tenericutes in the faeces sample.

In certain embodiments, the changed abundance of microorganisms in a dusp6 deficient animal according to the present invention, as compared wild-type animals, is as described in Table A.1-Table A.3 (also seen in Table 1 in examples below).

TABLE A.1

(phyla)

| Diet | Changes | Microbiota |
|---|---|---|
| Low-fat diet | increased abundance | Firmicutes (53.2%) vs. 33.97% in wild-type |
| | | Deferribacteres (3.62%) vs. 0.83% in wild-type |
| | decreased abundance | Bacteroidetes (42.13%) vs. 63.75% in wild-type |
| | | Actinobacteria (0.03%) vs. 0.06% in wild-type |
| | | Proteobacteria (0.59%) vs. 0.92% in wild-type |
| | enhancement in Firmicutes/Bacteroidetes ratio (about 1.23:1) vs. 0.53:1 | |
| High-fat diet | increased abundance | Bacteroidetes (62.94%) vs. 44.98% in wild-type |
| | decreased abundance | Firmicutes (34.62%) vs. 47.70% in wild-type |
| | reduction in Firmicutes/Bacteroidetes ratio (about 0.55:1) vs. 1.06:1 in wild type | |

TABLE A.2

(family)

| Diet | Changes in abundance | Microbiota |
|---|---|---|
| Low-fat diet | increased abundance | Ruminococcaceae (10.30%) vs. 6.34% in wild-type |
| | | Lachnospiraceae (12.43%) vs. 6.53% in wild-type |
| | decreased abundance | S24-7 (27.33%) vs. 52.13% in wild-type |
| High-fat diet | increased abundance | Bacteroidaceae (29.42%) vs. 10.98% in wild-type |
| | decreased abundance | Erysipelotrichaceae (8.21%) vs. 19.09% in wild-type |

TABLE A.3

(genus)

| Diet | Changes in abundance | Microbiota |
|---|---|---|
| Low-fat diet | increased abundance | *Mucispirillum* |
| | | *Lachnobacterium* |
| | | *Roseburia* |
| | decreased abundance | *Sutterella* |
| | | *Adlercreutzia* |
| High-fat diet | increased abundance | *Bacteroides* |
| | decreased abundance | *Sutterella* |

It shows that dusp6 deficiency not only alter the composition of the gut microbiota, but also change the intestinal microbiota response to HFD.

Changes in Basal Gut Transcriptome

Dusp6 deficient animal also exhibits changed basal gut transcriptome. Most up biological processes are involved in metabolism (for example, brown fat cell differentiation, fatty acid and triglyceride metabolism) and adhesion/cellular structure (for example, cell adhesion and extracellular matrix organization). In addition, many of the genes related to peroxisome proliferator-activated receptor gamma (Pparγ) signaling and tight junction (TJ) signaling pathways are significantly up-regulated. It suggests that dusp6 deficiency play a role in the regulation of gut barrier permeability.

Reversion of High-Fat-Diet Altered Gut Transcriptome

Dusp6 deficient animal exhibits high-fat-diet-specific transcriptomic responses to reverse the expression of genes associated with intestinal barrier functions and mucosal immunity involved in microbiome homeostasis, at least including (1) inhibition of increase in CD3+ T cells induced by HFD, inhibition of HFD induced CD4 gene expression, and prevention of HFD increased infiltration of CD3+ and CD4+ T cells (which suggests that dusp6 deficiency alters the HFD induced behavior of T lymphocytes in gut mucosal immunity); (2) downregulation of Ltα and Ltβ expression, enhancement of the junction structure of the ZO-1, and resistance to HFD-induced endotoxaemia (which suggests dusp6 deficiency can coordinate the formation of intestinal TJs and protects the intestinal epithelial barrier from FHD-induced interruption); (3) prevention of HFD-mediated Defa5 induction, prevention of HFD-mediated RegIIβ and RegIIIγ induction (which suggests that dusp6 deficiency can regulates the gut microbiota response against FHD by maintaining physiological levels of expression for specific antimicrobial peptides (AMPs)); and (4) induction of segmented filamentous bacteria (SFB).

III. Gut Microbiota from a Dusp6 Deficient Animal

According to the present invention, gut microbiota collected from a dusp6 deficient animal can be probiotic which confers benefit effects (e.g. altering the gut microbiota profile and providing anti-obesity effects).

Therefore, the method of the invention includes providing a dual-specificity phosphatase 6 (dusp6) deficient non-human animal; and collecting gut microbiota from the dusp6 deficient animal.

In one particular embodiment, gut microbiota are collected from a faecal sample of the dusp6 deficient animal, which can be suspended in saline and centrifuged to obtain the supernatant before administration to a receipt subject. In another particular embodiment, the gut microbiota as collected are subjected to a culture medium for culture for a period of time to obtain culcurable microbiota before administration to a receipt subject.

In some embodiments, the method of the invention further includes identifying at least one microbiota in a sample collected from the dusp6 deficient animal. Specifically, such a method for identifying a microbiota in a sample can include providing a sample, e.g. a faecal sample, comprising one or more microbiota, and detecting at least one microbiota in the sample based on specific molecular indicator(s) that can identify the microbiota. For example, the method can include preparing at least one nucleic acid sample, and the molecular indicator(s) as used can be a polymorphic polynucleotide, such as an rRNA gene (e.g. a 16S rRNA gene), which can be detected by determining the nucleotide sequence of the polymorphic polynucleotide. The method of the invention can further provide a microbiota profile found in the dusp6 deficient animal.

In some embodiments, the method of the invention can also include measuring a relative abundance of one or more microbiota to produce a microbiota profile found in the dusp6 deficient animal. The relative abundance of one or more microbiota or a microbiota profile can be compared to a reference abundance or a reference profile. For example, the reference profile can be a standardized (or normalized) microbiota profile obtained from a healthy animal (e.g. a wild type animal without a dusp6 deficiency) of the same species with similar conditions e.g. weight, age and gender.

In some embodiments, the method of the invention includes measuring anti-obesity activities of the microbiota obtained from a dusp6 deficient animal.

In some embodiments, the method of the invention includes identifying lean-associated microbes from the gut microbiota.

In certain embodiments, the lean-associated microbes can be identified by measuring whether the microbes are effective in reducing body weight, fat mass, and/or size of adipocytes in a subject upon administration of the microbes.

In certain embodiments, the lean-associated microbes can be identified by measuring whether the microbes are effective in increasing oxygen consumption and/or energy expenditure in a subject upon administration of the microbes.

In some embodiments, the method of the invention includes isolating the lean-associated microbes from the gut microbiota.

III. Microbiota Compositions and Uses Thereof

According to the present invention, the microbiota in the gut microbiota of a dusp6 deficient animal can be identified and then substantially purified/isolated. The term "substantially purified" or "substantially isolated" can be used interchangeably, as used herein, which refers to a bacterial type (e.g. phylum, class, order, family, genus, species, strain)) or a mixture of more than one bacterial types that are substantially enriched in a sample. It is understood that the term "purified" or "isolated" does not necessarily reflect the extent to which the peptide has been "absolutely" purified or isolated. For example, the sample substantially purified/isolated or enriched for the bacterial strain or mixture of strains of interest can mean that the sample has at least about 50%, 60%, 70%, 80%, 90% or greater of the desired bacterial strain(s) or less than about 40%, 30%, 20%, 10, 5%, 2%, 1% or less of the undesirable or other bacterial strains present.

Therefore, the present invention provides a microbiota composition and uses thereof.

In some embodiments, the composition of the invention comprises one or more substantially purified bacterial phyla, selected from the group consisting of: (i) Actinobacteria, (ii) Bacteroidetes, (iii) Cyanobacteria, (iv) substantially purified Deferribacteres, (v) substantially purified Firmicutes, (vi) substantially purified Proteobacteria, (vii) substantially purified TM7, (viii) substantially purified Tenericutes, and any combination thereof.

In some embodiments, the composition of the invention comprises one or more substantially purified bacterial families selected from the group consisting of (a) substantially purified Bacteroidaceae. (b) substantially purified S24-7, (b) substantially purified Rikenellaceae, (d) substantially purified Porphyromonadaceae, (e) substantially purified Odoribacteraceae, (f) substantially purified Ruminococcaceae, (g) substantially purified Erysipelotrichaceae, (h) Lachnospiraceae, (i) Lactobacillaceae, (j) Clostridiaceae, and any combination thereof.

In some embodiments, the composition of the invention comprises one or more substantially purified bacterial phyla and one or more substantially purified bacterial families as described herein.

In some embodiments, the composition of the invention comprises (iv) substantially purified Deferribacteres or (v) substantially purified Firmicutes, or a combination thereof.

In some embodiments, the composition of the invention comprises (f) substantially purified Ruminococcaceae or (h) Lachnospiraceae, or a combination thereof.

In certain embodiments, in the composition of the invention, (ii) substantially purified Bacteroidetes and (v) substantially purified Firmicutes are present in a ratio of about 1:1.2.

In certain embodiments, in the composition of the invention, (i) substantially purified Actinobacteria, (iv) substantially purified Deferribacteres and (vi) substantially purified Proteobacteria are present in a ratio of about 1:120:20.

In certain embodiments, in the composition of the invention, (i) substantially purified Actinobacteria, (iv) substantially purified Deferribacteres and (vi) substantially purified Proteobacteria are present in a ratio of about 1:120:20.

In certain embodiments, in the composition of the invention, (i) substantially purified Actinobacteria, (ii) substantially purified Bacteroidetes, (iv) substantially purified Deferribacteres, (v) substantially purified Firmicutes, and (vi) substantially purified Proteobacteria are present in a ratio of about 1:1400:120:1770:20.

In certain embodiments, the composition of the invention can be obtained from a dusp6 deficient animal according to the method as described herein.

A composition can be prepared by formulating active ingredients (e.g. probiotic microbiota) with a physiologically acceptable carrier such that the composition is in an appropriate form for the purpose of delivery, for example. The composition of the present invention particularly comprises about 0.1% by weight to about 100% by weight of the active ingredient, wherein the percentage by weight is calculated based on the weight of the whole composition. In some embodiments, the composition of the present invention can be formulated as a pharmaceutical composition or medicament for treatment. In some embodiments, the composition of the present invention can be formulated as a food product or dietary supplement.

As used herein, "physiologically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. The composition may additionally comprise lubricants; wetting agents; emulsifying and suspending agents; preservatives; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, fluid, and packaged powder.

The composition of the present invention may be delivered via any physiologically acceptable route, particularly oral. Preparation of an appropriate parenteral composition under sterile conditions may be accomplished with standard pharmacological techniques well known to persons skilled in the art.

In some embodiments, the composition of the present invention is useful in altering a relative abundance of microbiota in a subject in need thereof.

In some embodiments, the composition of the present invention is useful in reducing body weight and/or body fat or preventing an increase in body weight and/or body fat or increasing oxygen consumption and/or energy expenditure to facilitate a reduction in body weight and/or body fat in a subject in need thereof. The composition of the present invention also is useful in treating or preventing obesity or its associated disorders or conditions in a subject in need thereof.

In particular, the composition of the present invention does not reduce appetite and food intake in a subject receiving the composition. In more particular, the composition of the present invention does not reduce lean body mass in a subject According to another aspect of the invention, there is provided a method of administrating an effective amount of a composition as described herein to confer desired effects in a subject in need thereof.

In particular, there is provided a method for altering a relative abundance of microbiota in a subject in need thereof. There is also provided a method for reducing body weight and/or body fat or preventing an increase in body weight and/or body fat in a subject in need thereof. There is also provided a method for treating obesity or its associated disorders or conditions in a subject in need thereof.

The term "effective amount" used herein refers to the amount of an active ingredient to confer a desired biological effect in a treated subject or cell. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

As used herein, altering a relative abundance of microbiota in a subject can include increase and/or decrease the relative abundance of one or more microbiota in the subject, as compared to the corresponding abundance in a control subject.

As used herein, a control subject can be the same subject before being administrated with a composition as described herein, or a subject, preferably of similar weight, age, gender, race and/or having undergone a similar diet program which has not received a composition as described herein.

In some embodiments, the amount of the composition is effective in decreasing a relative abundance of TM7 in the subject. Particularly, the subject consumes a low-fat diet.

In some embodiments, the amount of the composition is effective in decreasing a relative abundance of *Streptococcaceae* in the subject. Particularly, the subject consumes a high fat diet.

In some embodiments, the amount of the composition is effective in increasing a relative abundance of *Escherichia, Parabacteroides* and/or *Lactobacillus* in the subject. Particularly, the subject consumes a low-fat diet.

In some embodiments, the amount of the composition is effective in increasing a relative abundance of Proteobacteria in the subject. Particularly, the subject consumes a high fat diet.

As used herein, the term "body fat" as used herein refers the loose connective tissue known as "adipose tissue". Body fat can be present throughout the body of an individual. The amount of body fat in an individual can be determined and/or estimated by a variety of methods identifiable to a skilled person, such as ultrasound measurements, magnetic resonance imaging, computed tomography. Additionally, an individual's body mass index (BMI) can also be indicative of the amount of body fat in an individual.

As used herein, the term "lean body mass" refers to the mass of a subject minus mass associated with fat content, and is often expressed as a percentage of total mass of a subject. Lean body mass is generally the mass of the bone, organs, muscle and proteins of the body such as collagen.

The term "treating" as used herein refers to the application or administration of a composition including one or more active agents to a subject afflicted with a disorder (e.g. obesity or its associated disorders or conditions), a symptom or conditions of the disorder, or a progression or predisposition of the disorder, with the purpose to cure, heal, alleviate, relieve, alter, remedy, ameliorate, improve, or affect the disorder, the symptoms or conditions of the disorder, the disabilities induced by the disorder, or the progression or predisposition of the disorder. Therefore, the term "treating" can also include, depending on the condition of the subject to be treated, preventing the disorder, including preventing onset of the disorder or of any symptoms associated therewith as well as reducing or alleviating the severity of the disorder or any of its symptoms prior to onset. In an exemplary embodiment, a method to treat or prevent obesity can include reducing the body weight, fat mass, and/or size of adipocytes, and/or increasing oxygen consumption and/or energy expenditure in a subject in need, as compared to a control subject. A control subject can be the same subject before being administrated with a composition as described herein, or a subject, preferably of similar weight, age, gender, race and/or having undergone a similar diet program which has not received a composition as described herein.

The subject to be treated by the methods as described herein can be a mammal, particularly a human. Examples of mammals can include a rodent (e.g., mouse, rat, chipmunk, prairie dog, squirrel, beaver, gopher, hamsters, voles, gerbils, porcupines, guinea pigs, etc.), a livestock animal (e.g., pigs, cattle, goats, deer, sheep, yaks, etc.), a companion animal (e.g., cat, dog, etc.), or a primate (e.g., lemurs, monkeys, apes, humans, etc.). In particular, a subject in need of the treatment method as described herein can be a human individual that has, is suspected to have, or is at risk for having a target disease/disorder/condition, e.g. a human who is overweight or obese or consumes high-fat diet or is sensitive to diet-induced obesity, or has a family histories of obesity or its associated disorders or conditions.

The term "obesity" as used herein generally refers to an excess of body weight in a subject. Typically, a human subject who has a body mass index (BMI) of 30 kg/m² or more is considered to have an excess of body weight. A "morbidly obese" individual has a body mass index greater than 35 kg/m². Obesity also can be defined on the basis of body fat content or percentage body fat. Obesity is generally defined as greater than 25% body fat for a male or more than 30% body fat content for a female. In an exemplary embodiment, obesity refers to diet induced obesity. A non-obese or normal subject can have a BMI and/or percentage body fat that is within recommended levels or close to recommended levels (also referred to as "normal" levels). Recommended BMI ranges from about 18.5-25. Regarding recommended percentage body fat, levels as high as 25-30% for women and 18-25% for men are acceptable. In an exemplary embodiment, a method to treat obesity can include reducing the BMI and/or percentage body fat in a subject in need to normal levels.

Obesity is linked to a variety of medical conditions. In particular, the method of the invention is effective in treating obesity associated disorders or conditions, such as type 2 diabetes, hyperglycemia, glucose intolerance, dyslipidemia, insulin resistance, hyperinsulinemia, fatty liver, cardiovascular disease, stroke, and cancer.

According to the method of the present invention, the composition can be administrated to a subject in need by a proper route. In an exemplary embodiment, the composition is administrated via oral route (e.g., by a solid such as a pill, tablet, or capsule, or by liquid). The composition can be delivered to one or more regions within the subject. The regions can include but are not limited to a region within the gastrointestinal tract system such as an oral cavity, stomach, small intestine, large intestine, or colon. Examples of routes of administration include but are not limited to rectal administration (e.g., by suppository, enema, upper endoscopy, upper push enteroscopy, or colonoscopy), or intubation through the nose or the mouth (e.g., by nasogastric tube, nasoenteric tube, or nasal jejunal tube).

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

In this study, using a germ-free mouse model, we found that faecal/gut microbiota derived from dusp6-deficient mice significantly increased energy expenditure and reduced weight gain in recipient wild-type mice fed on a high-fat diet. On analysis of the intestinal transcriptome of dusp6-deficient mice, we found that dusp6 deficiency mainly induced biological processes involved in metabolism and the extracellular matrix, particularly the peroxisome proliferator-activated receptor gamma (Ppar$\gamma$) pathway and tight junction genes. Furthermore, dusp6-deficient mice have a high-fat-diet-specific transcriptomic response to reverse the expression of genes associated with intestinal barrier functions and mucosal immunity involved in microbiome homeostasis. This study demonstrates that dusp6 deficiency is a strong genetic factor shaping gut microbiota, and that it confers obesity protection by ameliorating the gut microbiota response to diet-mediated stress.

1. Materials and Methods 1.1 Mice

C57BL/6J dusp6−/− mice (generated from a dusp6−/− embryonic stem cell clone purchased from the Jackson Laboratory) and WT C57BL/6J mice were maintained under semi-specific pathogen-free (SPF) conditions. Mice with the same genotype and with similar initial weight (no blinding) from different litters were caged together (three to four mice per cage), housed under a 12 hour light cycle and then fed autoclaved chow diet, 10% kcal control diet (CD) or 45% kcal high-fat diet (HFD). Five- to six-week-old male germ-free C57BL/6J mice were purchased from National Laboratory Animal Center (NLAC) and sterility was certified by NLAC and further confirmed by qPCR analysis of eubacteria 16S rRNA genes. Groups of five to eight-week-old male mice were used in the following experiments and the sample sizes for the DIO experiments were chosen based on pilot experiments to have at least 80% power at the $\alpha$=0.05 threshold. All mouse experiments were completed following a protocol approved by the institutional animal care and use committee of the National Health Research Institutes, Taiwan.

1.2 Glucose and Insulin Tolerance Tests

For the glucose tolerance test (GTT), mice were fasted for 12 h with free access to water, and intraperitoneally injected with glucose at a dose of 2 g per kg body weight. Blood glucose level was measured with a glucometer (Johnson & Johnson) immediately before and 15, 30, 60, 90 and 120 min after glucose injection. For the insulin tolerance test (ITT), mice were fasted for 6 h with free water access, and intraperitoneally injected with insulin at a dose of 0.75 U per kg body weight. Blood glucose level was measured immediately before and 15, 30, 45, 60 and 90 min after insulin injection.

1.3 Faecal DNA Extraction, 16S Ribosomal RNA Sequencing and Microbiome Analysis

Faecal DNA was extracted using the PowerFecal DNA Isolation Kit (Mo Bio Laboratories) and the V3-V5 region of 16S ribosomal RNA gene was amplified using barcoded primers. Barcoded amplicons were sequenced using the Illumina MiSeq platform. 16S rRNA analysis was performed using the open-source software package Quantitative Insights Into Microbial Ecology (QIIME), v.1.8.0 (ref. 38). Primer sequences were trimmed and low-quality reads below a quality score of 20 were removed. Sequences were clustered based on 0.99 similarity using UClust into operational taxonomic units (OTUs) using the May 2013 release of Greengenes as a reference for closed-reference-based OTU picking[39,40]. A representative sequence was selected from each OTU and Ribosomal Database Project classifier was used to assign taxonomy to the representative sequence, using the Greengenes reference database clustered at 99% identity as the training set41. Both alpha (Shannon and Good's) and beta diversity (weighted and unweighted UniFrac) analysis was performed, using a rarefaction of 1,000 sequences42. The PERMANOVA/Adonis test was conducted using vegan: Community Ecology Package (R package version 2.3-4; http://CRAN.R-project.org/package=vegan). Faecal samples were collected from both WT and D6KO mice before switching to CD or HFD (T0) and at 16 weeks after HFD or CD (T16). Next-generation sequencing of the V3-V5 region of bacterial 16S ribosomal DNA genes was then performed on genomic DNA extracted from these faecal samples.

1.4 DIO, FMT and CFMT

For the DIO model, groups of six- to eight-week-old male dusp6−/− mice were fed on a control diet (10% kcal from fat) or HFD (45% kcal from fat) (Research Diet) for 16 weeks. Body weight and food intake were monitored every week. Germ-free male C57BL/6J mice were purchased from the National Laboratory Animal Center, Taiwan. For FMT, groups of five to eight male donor mice at six to eight weeks of age were placed into autoclaved cages and 0.5 g of fresh of faeces was collected within 30 min. The faeces were then immediately resuspended in 5 ml sterile phosphate buffer saline (PBS) and centrifuged for 30 s to pellet the particle mass. The supernatant slurries were collected and orally gavaged into five- to six-week-old germ-free recipient mice. For CFMT, 10 μl PBS slurries (described above) were subjected to 3 ml BHI broth and cultured in an anaerobic jar at 37° C. for 48 h. The cultures were then used to perform CFMT. FMT and CFMT were performed three times per week for four weeks (total 12 times) and recipient mice were fed CD or HFD after 2 weeks of FMT for 16 weeks. Immediately after first FMT or CFMT, the formerly germ-free FMT/CFMT recipient mice were maintained under semi-SPF conditions. The experiments on FMT and CFMT recipient mice were manipulated carefully and separately to prevent cross-contamination of faecal microbiota.

1.5 RNA Isolation, RNA Sequencing and Bioinformatics.

Total RNA was isolated from 20 mg homogenized intestinal tissue adjacent to the caecum from four to five mice per group using RNeasy Plus mini kit (Qiagen) following the manufacturer's instructions. After RNA extraction, RNA integrity (RIN score>9.0) and quantity were determined on a Nanodrop spectrophotometer (Thermoscientific) and Agilent 2100 Bioanalyzer (Agilent Technologies) following the manufacturers' instructions. Total RNA samples (2 μg) were processed by Beijing Genomics Institute (BGI) for mRNA enrichment using the oligo(dT) magnetic beads and indexed dsDNA libraries constructed using the Illumina TruSeq RNA sample preparation kit (Illumina) were run on a HiSeq2000 for SR50 according to the BGI experiment pipeline. HiSeq2000 reads were imported to R with Bioconductor for alignment to Mus_musculus.GRCm38 release-79 from Ensembl using Spliced Transcripts Alignment to Reference (STAR) software43 and the differential analysis of count data was completed using the DESeq2 package44. Genes with an adjusted P less than 0.05 were selected as differentially expressed genes (DEGs) for further gene ontology and pathway enrichment analyses using DAVID v6.7 (refs 45,46) and X2K Expression2Kinases softwares (enrichment cutoff is at least five DEGs in one pathway)47. This network analysis was performed using the GeneMANIA app and the visualization was created using Cytoscape 3.2.1 (ref. 48).

1.6 Real-Time RT-PCR and Real-Time PCR for Bacterial Detection cDNA was synthesized from 1 μg total RNA by M-MLV reverse transcriptase (Promega). Fast start Universal SYBR GreenMaster (Rox) (Roche Applied Science) was used to perform real time PCR reactions on a LightCycler 480 System (Roche Applied Science). Expressions were normalized to tbp-1 for all intestinal genes. The plasmid containing the 16S sequence of *A. muciniphila* (GenBank: LC071790.1, nucleotide 1089-1418) was used as a standard to assess the abundance of *A. muciniphila*. For detailed information regarding the primers used in this study, see Supplementary Table 4.

1.7 Tissue Collection and Histology

After the mice were killed, intestine, liver and flank adipose tissue were collected and fixed in 4% formaldehyde. Tissues were then paraffin-embed, sectioned and stained by haematoxylin and eosin (H&E). Immunohistochemistry was performed as previously described49. The appropriate volume of diluted primary anti-DUSP6 (LS-B5975, LifeSpan BioSciences), anti-CD3 (C7930, Sigma-Aldrich) or anti-CD4 (14-9766-82, eBioscience) antibody was added to cover the specimen and the samples were incubated at 4° C. overnight. Nuclei were then counterstained with haematoxylin. For fluorescence immunohistochemistry, intestine tissues adjacent to caecum were excised, directly embedded in frozen section media (Leica) and snap-frozen in liquid nitrogen. Several 6-μm-thick sections were then collected and fixed in ice-cold acetone. The fixed tissues were immuno-stained using anti-ZO-1 antibody (61-7300, Invitrogen), followed by Alexa Fluor-488 conjugated secondary antibody (Invitrogen). Cell nuclei were stained with 4,6-diamidino-2-phenylindole (DAPI) containing mounting solution (Invitrogen). All images in this study were captured by a Leica DM2500 microscope.

1.8 Generation of D6KO Caco-2 Cell

D6KO Caco-2 cells were generated with the CRISPR/Cas9 system. Expression vectors of guide RNA (target sequence: GATCGCCATTTCCGACGCGAAGG (SEQ ID NO: 5), targeting Exon1 of the dusp6 gene) and the Cas9 gene were co-transfected into human Caco-2 cells (a gift from Chiung-Tong Chen, NHRI) by using Lipofectamine LTX & PLUS Reagent (15338-100, Thermo Fisher Scientific). At 72 h after transfection, cells were subjected to hygromycin selection. Single cells were isolated by appropriate dilution and maintained until clonal colonies were obtained. The knockout candidate clones were screened by T7E1 assay and the nonsense mutation of the DUSP6 gene was confirmed by DNA sequencing. The depletion of DUSP6 expression of DUSP6 KO Caco-2 cells was confirmed by immunoblot analysis (ab76310, Abcam). The Caco-2 cell line has been authenticated with the Promega StemElite ID System and tested for *mycoplasma* contamination.

1.9 Trans-Epithelial Electrical Resistance (TEER)

Caco-2 cells were maintained and differentiated following previously described protocols50. In brief, for differentiation, 1×104 cells were seeded on polyester membrane insert (costar 3470, Corning) and the medium was changed three times a week. After 21 days of differentiation, the TEER was measured by voltohmmeter (Millicell ERS-2, Millipore).

1.10 Mouse Gut Permeability Assay

Before the assay, eight-week-old male WT and D6KO mice were fasted without water supplement for 4 h. Mice were then orally gavaged with fluorescein isothiocyanate conjugated 4 kDa dextran (50 mg per 100 g body weight) (46944, Sigma-Aldrich). At 2 h after gavage, blood was collected from the facial vein and the serum was prepared for fluorescence measurements (excitation, 490 nm; emission, 520 nm).

1.11 Limulus Amoebocyte Lysate (LAL) Test.

Mouse serum was diluted with PBS at 1:10 dilution and digested with 1/200 (vol/vol) PYROSPERSE dispersing agent (F188, Lonza). The PYROSPERSE digested serum samples were then subjected to endpoint chromogenic LAL assays (QCL-1000, Lonza) for serum endotoxin level determination according to the manufacturer's instructions.

1.12 Statistical Analysis.

Statistical analysis, excluding RNA-seq and microbiome, was performed using Prism 5.0 (GraphPad Software). Animals not meeting the preestablished criteria were excluded from analysis. Statistical analyses were performed with averages of biological replicates. Comparisons for animal experiments between two groups without a distribution assumption were analysed using a two-tailed Mann-Whitney test. Comparisons for in vitro cell culture experiments between two groups were analysed using an unpaired two-tailed t-test. Any comparisons of more than two data sets were performed with an analysis of one-way ANOVA followed by Tukey's post-hoc test. Differences were considered significant when P<0.05.

1.13 Data Availability.

Raw sequencing data files have been uploaded to NCBI under the following BioProject ID: PRJNA320922 (SRA: SRP074626). The data that support the findings of this study are available, on request, from C.Y.K.

Figure 1:
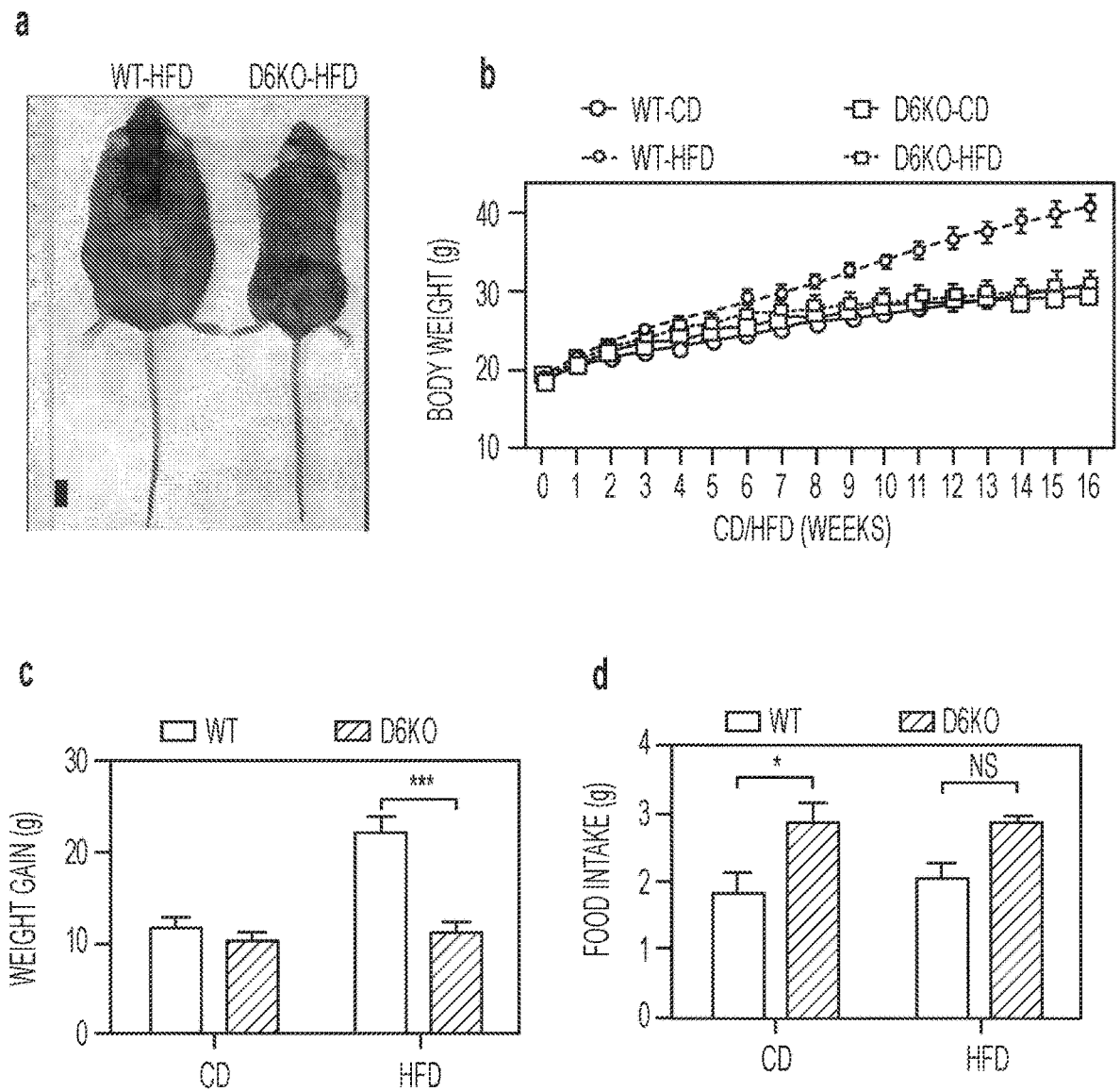
FIG. 1 shows that dusp6-deficient-mice-derived faecal microbiota increases DIO resistance in fecal microbiota transplant (FMT) recipient mice. a,e, Representative images of mice after 16 weeks of high fat food (HFD) feeding: wild-type (WT) and dusp6-knockout mice (designated as D6KO) (a) and FMT recipient mice (e). Scale bars, 10 mm. b,f, Male mice were fed on CD or HFD for 16 weeks, and body weights were monitored weekly: 6-8-week-old WT and D6KO mice (b) and 5-6-week-old FMT recipient mice (f). c,g, Weight gain of mice after 16 weeks of CD or HFD treatment: WT and D6KO mice (c) and FMT recipient mice (g). d,h, Twenty-four-hour food intake of an individual male WT/D6KO mouse (d) and a WT/D6KO-microbiota recipient mouse (h). Number of mice per group in b-d: WT-CD, N=10; WT-HFD, N=8; D6KO-CD, N=10; D6KO-HFD, N=6. In f, donor: WT-CD, N=12; donor: WT-HFD, N=12; donor: D6KO-CD, N=13; donor: D6KO-HFD, N=13. In g,h, N=8 mice for each group. i,j, Nuclear magnetic resonance fat/lean body composition analysis was performed on WT/D6KO FMT recipient mice after eight weeks of CD/HFD treatment: donor: WT-CD, N=4; donor: WT-HFD, N=4; donor: D6KO-CD, N=5; donor: D6KO-HFD, N=5. k,l, Consumption of $O_2$ ($VO_2$) (k) and energy expenditure (l) of representative mice measured by indirect calorimetry for 24 h. The 24-h average is indicated to the right. Number of mice per group: donor: WT-HFD, N=4; donor: D6KO-HFD, N=5. *P<0.05, according to Mann-Whitney analysis. m,n, H&E-stained sections of liver tissue (m) and flank adipose tissue (n) from male WT and D6KO mice fed on CD or HFD for 16 weeks. Scale bars, 100 µm. NS, statistically non-significant. *P<0.05, ***P<0.0005, according to one-way ANOVA analysis and Tukey's post-hoc test. Numerical data are presented as the mean±s.e.m. of each group.

2. Results 2.1 D6KO Faecal Microbiota Contributes to DIO (Diet-Induced Obesity) Resistance We found that D6KO mice show resistance to DIO (FIG. 1a-c), which is consistent with findings from a previous study[6]. We observed that D6KO mice show a higher food intake than wild-type (WT) control mice on a control diet (CD), and a similar trend was observed for D6KO and WT mice fed on a high-fat diet (HFD) (FIG. 1d). These results suggest that dusp6 deficiency does not protect mice from DIO via a decrease in food consumption. Dusp6 deficiency also improved glucose tolerance and increased insulin sensitivity in HFD-fed mice, whereas HFD fed WT mice exhibited severe glucose intolerance, insulin resistance and higher fasting glucose levels (FIG. 7a-c). Moreover, dusp6 deficiency attenuated the HFD-induced fat pad mass increase (FIG. 7d), reduced adipocyte size (FIG. 7e) and protected mice from developing HFD-induced hepatosteatosis (FIG. 7f).

To address whether dusp6 regulates DIO resistance by modulating the gut microbiota response, we performed faecal-microbiota transplantation (FMT) with germ-free mice (FIG. 8a). Our results demonstrate that D6KO-mice-derived faecal microbiota (D6KO-microbiota) significantly reduced the weight gain of recipient mice on HFD when compared with HFD-fed mice receiving WT-mice-derived faecal microbiota (WT-microbiota) (FIG. 1e-g). Similar to D6KO mice, D6KO-microbiota did not reduce the 24 h food intake of recipient mice on either CD or HFD (FIG. 1h). We further found that when challenged with HFD for 8 weeks, the fat mass of D6KO-microbiota recipient mice was reduced compared with WT-microbiota recipient mice (FIG. 1i). However, the lean body mass was not affected in either group of recipient mice (FIG. 1j). An indirect calorimetry analysis on FMT recipient mice showed that D6KO-microbiota recipient mice had an ~15% increase in both O2 consumption (FIG. 1k) and energy expenditure (FIG. 1l). In addition, D6KO-microbiota alleviated the development of HFD-induced hepatosteatosis (FIG. 1m) and reduced the size of adipocytes (FIG. 1n) in recipient mice on HFD. These results demonstrate that dusp6 deficiency could modulate the resistance to DIO through the gut microbiota.

2.2 Dusp6 Deficiency Alters the Gut Microbiome

We evaluated the overall gut bacterial load and found an increased bacterial load in HFD-fed WT mice but not in dusp6-deficient mice (FIG. 8b). This implies that dusp6 deficiency might regulate the gut microbiota response to HFD, so we then investigated whether dusp6 deficiency altered the gut microbiome.

Figure 2:
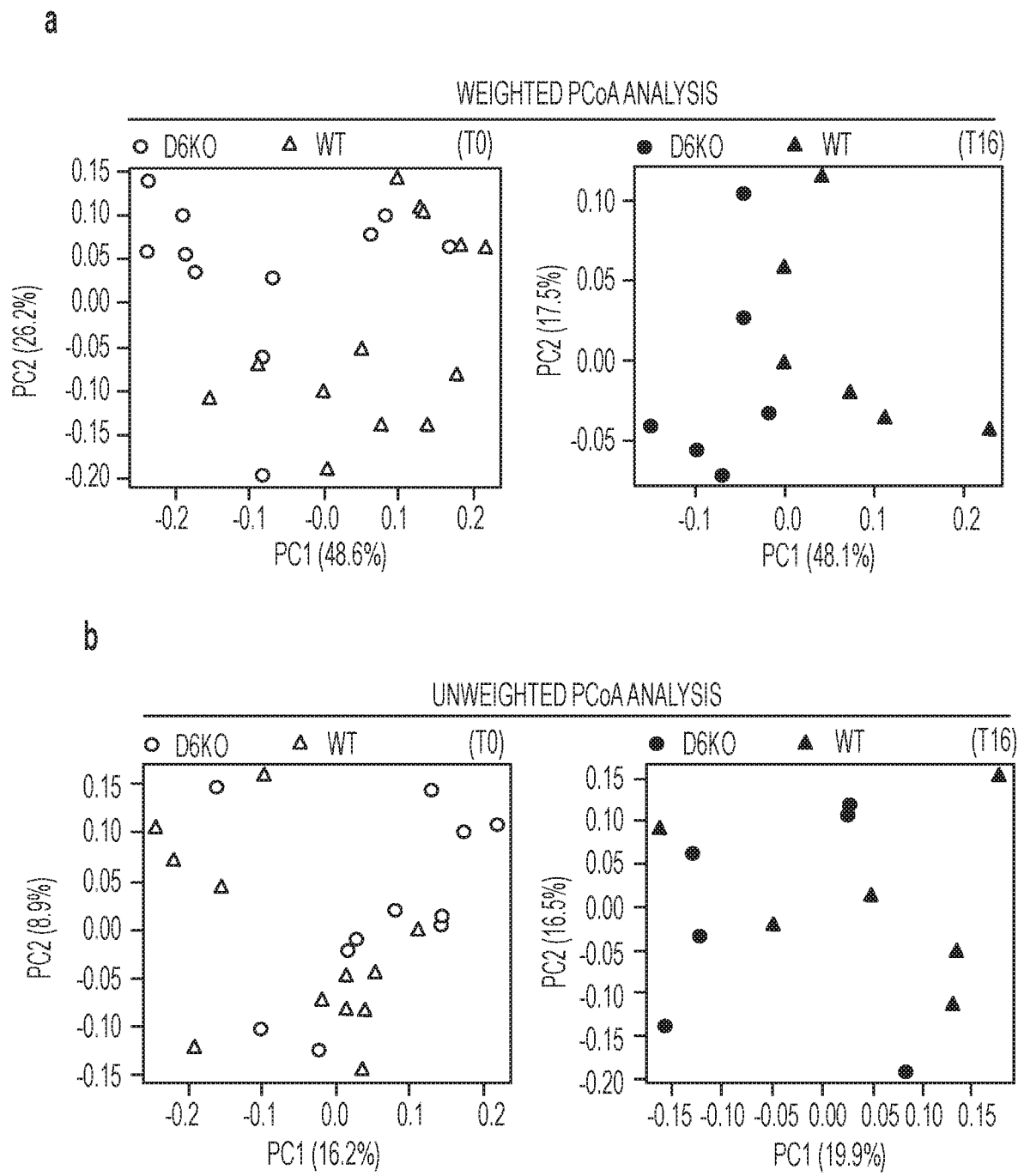
FIG. 2 shows that dusp6-deficient mice are resistant to HFD-mediated alteration of the gut microbiome. a,b, Weighted UniFrac (a) and unweighted UniFrac (b) PCoA plots representing changes between chow diet (T0) or HFD (T16)-fed WT and D6KO mice. c,d, Composition of gut microbiota before and after 16 weeks of HFD treatment at the phylum level. e,f, Abundance of Bacteroidetes (e) and Firmicutes (f) family members for each condition and time point. g, Changes in bacterial phyla after HFD treatment between WT and D6KO mice. Values are means of each group. See also Table 1. h,i, LDA scores of the differentially abundant microbial clades (with LDA score >2 and significance of α<0.05, determined by Kruskal-Wallis test). Number of mice per group: T0: WT-CD, N=11 and D6KO-CD, N=13; T16: WT-HFD, N=6 and D6KO-HFD, N=6.

HFD has been shown to alter the gut microbiome in mice[10] and we also had a similar finding in both WT and dusp6-deficient mice (FIG. 8c,d). Both weighted and unweighted UniFrac-principal coordinates analysis (PCoA) analyses showed that the faecal/gut microbiome in dusp6-deficient mice clustered separately from WT mice both before (T0) and after (T16) HFD treatment (FIG. 2a,b). The beta-diversity obtained using a permutational multivariate analysis of variance (PERMANOVA)/Adonis test for the faecal/gut microbiome between WT and dusp6-deficient mice showed significant differences at both time points (Table 1).

TABLE 1

Taxonomic composition at phylum and family level of fecal/gut microbiota of WT and dusp6 KO mice before and after HFD treatment.

|  | Dusp6 KO-Chow | WT-Chow | Dusp6 KO-HFD | WT-HFD |
|---|---|---|---|---|
| Samples | 11 | 13 | 6 | 6 |
| Good's coverage (phylum) | 98.22% | 98.5% | 98.48% | 98.83% |
| Shannon index (phylum) | 6.78 | 6.78 | 6.18 | 6.57 |
| PERMANOVA/Adonis test | Chow diet fed (WT vs. Dusp6 KO) R2 = 0.14841, p = 0.002 | | HFD fed (WT vs. Dusp6 KO) R2 = 0.27924, p = 0.003 | |
| Phylum (%) | | | | |
| Actinobacteria | 0.03 ± 0.01 | 0.06 ± 0.02* | 0.24 ± 0.04 | 0.23 ± 0.05 |
| Bacteroidetes | 42.13 ± 6.26 | 63.75 ± 2.81* | 62.94 ± 3.82 | 44.98 ± 5.27* |
| Cyanobacteria | 0.08 ± 0.01 | 0.14 ± 0.05 | 0.00 ± 0.00 | 0.1 ± 0.03* |
| Deferribacteres | 3.62 ± 1.01 | 0.83 ± 0.24** | 1.05 ± 0.42 | 1.86 ± 1.32 |
| Firmicutes | 53.2 ± 5.64 | 33.97 ± 2.79* | 34.62 ± 3.58 | 47.70 ± 2.11** |
| Proteobacteria | 0.59 ± 0.08 | 0.92 ± 0.10* | 1.01 ± 0.29 | 5.08 ± 2.30 |
| TM7 | 0.02 ± 0.00 | 0.02 ± 0.01 | 0.00 ± 0.00 | 0.01 ± 0.00 |
| Tenericutes | 0.35 ± 0.09 | 0.30 ± 0.09 | 0.13 ± 0.05 | 0.03 ± 0.01 |
| Family (%) | | | | |
| Bacteroidaceae | 2.24 ± 0.91 | 1.18 ± 0.23 | 29.42 ± 3.52 | 10.98 ± 1.63** |
| S24-7 | 27.33 ± 5.95 | 52.13 ± 3.26** | 21.90 ± 1.84 | 18.70 ± 2.51 |
| Rikenellaceae | 9.81 ± 1.45 | 7.30 ± 0.95 | 4.85 ± 1.07 | 6.27 ± 0.95 |
| Porphyromonadaceae | 0.07 ± 0.01 | 0.11 ± 0.03 | 2.74 ± 0.60 | 2.59 ± 0.79 |
| Odoribacteraceae | 1.99 ± 0.36 | 2.17 ± 0.35 | 2.22 ± 0.43 | 5.24 ± 1.46 |
| Ruminococcaceae | 10.30 ± 1.14 | 6.34 ± 0.90* | 11.65 ± 2.21 | 15.62 ± 1.62 |
| Erysipelotrichaceae | 0.24 ± 0.07 | 0.18 ± 0.04 | 8.21 ± 1.79 | 19.09 ± 1.70** |

TABLE 1-continued

Taxonomic composition at phylum and family level of fecal/gut
microbiota of WT and dusp6 KO mice before and after HFD treatment.

|  | Dusp6 KO-Chow | WT-Chow | Dusp6 KO-HFD | WT-HFD |
|---|---|---|---|---|
| Lachnospiraceae | 12.43 ± 1.85 | 6.53 ± 0.97** | 3.23 ± 0.62 | 3.84 ± 0.39 |
| Lactobacillaceae | 2.72 ± 0.87 | 5.73 ± 1.59 | 0.95 ± 0.29 | 0.846 ± 0.34 |
| Clostridiaceae | 1.22 ± 0.35 | 0.82 ± 0.30 | 0.055 ± 0.02 | 0.04 ± 0.02 |

Data are presented as the mean ± SEM.
Asterisk ($P < 0.05$) and double asterisks ($P < 0.005$) indicate statistical difference according to Mann-Whitney analysis performed on the comparison of Chow diet fed WT vs. Dusp6 KO mice or HFD fed WT vs. Dusp6 KO mice data set.

These results suggest that both before and after HFD treatment, there were both qualitative and quantitative differences in the gut microbiome between dusp6-deficient and WT mice[11,12].

Before HFD treatment, dusp6-deficient mice had a higher abundance of Firmicutes (P=0.015) and Deferribacteres (P=0.003) phyla and lower abundance of Bacteroidetes (P=0.013), Actinobacteria (P=0.043) and Proteobacteria (P=0.021) phyla (Table 1 and FIG. 2c,d) than WT mice. We found that HFD increased the Firmicutes/Bacteroidetes ratio (Table 1 and FIG. 2c) in WT mice, as reported previously[7,8,13], whereas D6KO mice showed a reduction in the Firmicutes/Bacteroidetes ratio. After further analyzing the Firmicutes/Bacteroidetes composition at the family level, we found that before HFD treatment, dusp6-deficient mice harboured reduced levels of S24-7 (P=0.0031) and increased levels of Ruminococcaceae (P=0.0205) and Lachnospiraceae (P=0.0091). After HFD treatment, dusp6-deficient mice had an increase in Bacteroidaceae (P=0.0011 compared with D6-T0, P=0.0022 compared with WT-T16) and had a lower abundance of Erysipelotrichaceae compared to WT mice (P=0.0043) (Table 1 and FIG. 2e,f). Remarkably, D6KO mice demonstrated a resistance against HFD-mediated alteration of Firmicutes and Bacteroidetes (FIG. 2g). We further applied linear discriminant analysis (LDA) effect size (LEfSe) analysis to the microbiome data and found 17 differentially abundant clades (α=0.05) in CD-treated WT and dusp6-deficient mice (FIG. 2h) and 15 differentially abundant clades in HFD-treated mice (FIG. 2i). In CD-fed dusp6-deficient mice, a reduction in Sutterella and Adlercreutzia genera and increase in Mucispirillum, Lachnobacterium and Roseburia genera were observed (FIG. 2h). Roseburia spp. levels have been shown to be positively correlated with host metabolic parameters improvement under DIO14. In HFD-fed dusp6-deficient mice, the loss of the Sutterella genus within the Alcaligenaceae family of Burkholderiales was maintained (FIG. 2i). The HFD-induced increase in the Allobaculum genus within the Erysipelotrichaceae family of the Erysipelotrichales order in WT mice was not observed in dusp6-deficient mice (FIG. 2i). Under HFD challenge, dusp6 deficiency increased the abundance of the Bacteroides genus within the Bacteroidaceae family of the Bacteroidales order (FIG. 2i).

Our results are consistent with previous studies that showed that HFD increased the abundance of Erysipelotrichaceae and reduced the relative abundance of Bacteroidetes in mice[15], and the enriched abundance of Erysipelotrichaceae was further observed in obese humans[16]. Collectively, our results suggest that dusp6 deficiency not only altered the composition of the gut microbiome, but also changed the intestinal microbiome response to HFD.

2.3 D6KO Microbiota Impacts Host Microbiome HFD Response

To investigate how transplanted microbiota respond to HFD, we profiled the faecal microbiome before and after HFD challenge in FMT recipient mice. The beta-diversity with a PERMANOVA/Adonis test for the faecal/gut microbiome in WT-microbiota and D6KO-microbiota recipient mice showed a significant difference at time point 0 (Table 2).

TABLE 2

Taxonomic composition at phylum and family level of fecal/gut
microbiota of WT and D6KO microbiota recipient mice before and after HFD treatment.

|  | Dusp6 KO-Chow | WT-Chow | Dusp6 KO-HFD | WT-HFD |
|---|---|---|---|---|
| Samples | 16 | 16 | 8 | 8 |
| Good's coverage (phylum) | 99.15% | 99.2% | 99.06% | 99.13% |
| Shannon index (phylum) | 6.07 | 6.17 | 6.56 | 6.71 |
| PERMANOVA/Adonis test | Chow diet fed FMT (WT vs. D6KO) $R^2 = 0.11135$, p = 0.005 | | HFD fed FMT (WT vs. D6KO) $R^2 = 0.11582$, p = 0.065 | |
| Phylum (%) | | | | |
| Actinobacteria | 0.49 ± 0.06 | 0.47 ± 0.05 | 0.31 ± 0.06 | 0.38 ± 0.07 |
| Bacteroidetes | 45.12 ± 3.25 | 45.19 ± 2.63 | 31.65 ± 2.48 | 29.88 ± 2.90 |
| Cyanobacteria | N.D. | N.D. | 0.05 ± 0.02 | 0.03 ± 0.01 |
| Deferribacteres | 0.86 ± 0.19 | 0.92 ± 0.23 | 0.46 ± 0.14 | 0.82 ± 0.42 |
| Firmicutes | 50.37 ± 3.27 | 51.55 ± 2.53 | 66.86 ± 2.50 | 68.42 ± 2.74 |
| Proteobacteria | 3.13 ± 0.54 | 1.84 ± 0.35 | 0.40 ± 0.10 | 0.39 ± 0.08 |

TABLE 2-continued

Taxonomic composition at phylum and family level of fecal/gut microbiota of WT and D6KO microbiota recipient mice before and after HFD treatment.

| | Dusp6 KO-Chow | WT-Chow | Dusp6 KO-HFD | WT-HFD |
|---|---|---|---|---|
| TM7 | 0.01 ± 0.00 | 0.02 ± 0.00** | 0.01 ± 0.00 | 0.02 ± 0.00 |
| Tenericutes | 0.02 ± 0.00 | 0.02 ± 0.00 | 0.21 ± 0.06 | 0.07 ± 0.01 |
| Family (%) | | | | |
| Bacteroidaceae | 22.74 ± 2.62 | 22.59 ± 2.42 | 5.52 ± 0.69 | 5.71 ± 1.62 |
| S24-7 | 15.88 ± 0.97 | 17.67 ± 1.32 | 16.19 ± 0.74 | 15.92 ± 0.89 |
| Rikenellaceae | 1.44 ± 0.19 | 1.43 ± 0.18 | 3.47 ± 0.67 | 3.57 ± 0.59 |
| Porphyromonadaceae | 4.48 ± 0.61 | 2.97 ± 0.35 | 0.78 ± 0.15 | 0.80 ± 0.17 |
| Odoribacteraceae | 0.17 ± 0.05 | 0.29 ± 0.07 | 5.32 ± 1.55 | 3.48 ± 0.51 |
| Ruminococcaceae | 6.69 ± 0.77 | 7.90 ± 0.90 | 13.39 ± 1.67 | 13.14 ± 2.00 |
| Erysipelotrichaceae | 21.03 ± 2.36 | 26.16 ± 2.50 | 30.46 ± 5.52 | 27.64 ± 4.37 |
| Lachnospiraceae | 3.58 ± 0.36 | 3.39 ± 0.36 | 3.28 ± 0.25 | 4.74 ± 0.95 |
| Lactobacillaceae | 13.09 ± 1.89 | 8.32 ± 1.25 | 6.42 ± 1.32 | 9.22 ± 2.02 |
| Clostridiaceae | 0.07 ± 0.02 | 0.09 ± 0.01 | 0.05 ± 0.01 | 0.06 ± 0.00 |
| Dehalobacteriaceae | 0.21 ± 0.03 | 0.22 ± 0.03 | 0.21 ± 0.03 | 0.19 ± 0.03 |
| Enterococcaceae | 0.04 ± 0.01 | 0.10 ± 0.03 | 0.27 ± 0.11 | 0.46 ± 0.16 |
| Turicibacteraceae | 0.00 ± 0.00 | 0.06 ± 0.03** | 0.08 ± 0.03 | 0.19 ± 0.05 |
| Peptococcaceae | 0.02 ± 0.01 | 0.02 ± 0.01 | 0.13 ± 0.04 | 0.16 ± 0.04 |
| Streptococcaceae | 0.05 ± 0.01 | 0.11 ± 0.02 | 0.06 ± 0.01 | 0.17 ± 0.05** |
| Desulfovibrionaceae | 0.21 ± 0.03 | 0.24 ± 0.05 | 0.31 ± 0.07 | 0.23 ± 0.05 |
| Helicobacteraceae | 0.06 ± 0.01 | 0.07 ± 0.014 | 0.07 ± 0.03 | 0.14 ± 0.05 |
| Alcaligenaceae | 2.63 ± 0.44 | 1.54 ± 0.34 | 0.01 ± 0.00 | 0.00 ± 0.00 |
| Enterobacteriaceae | 0.22 ± 0.13 | 0 | 0.01 ± 0.00 | 0.00 ± 0.00* |

Figure 3:
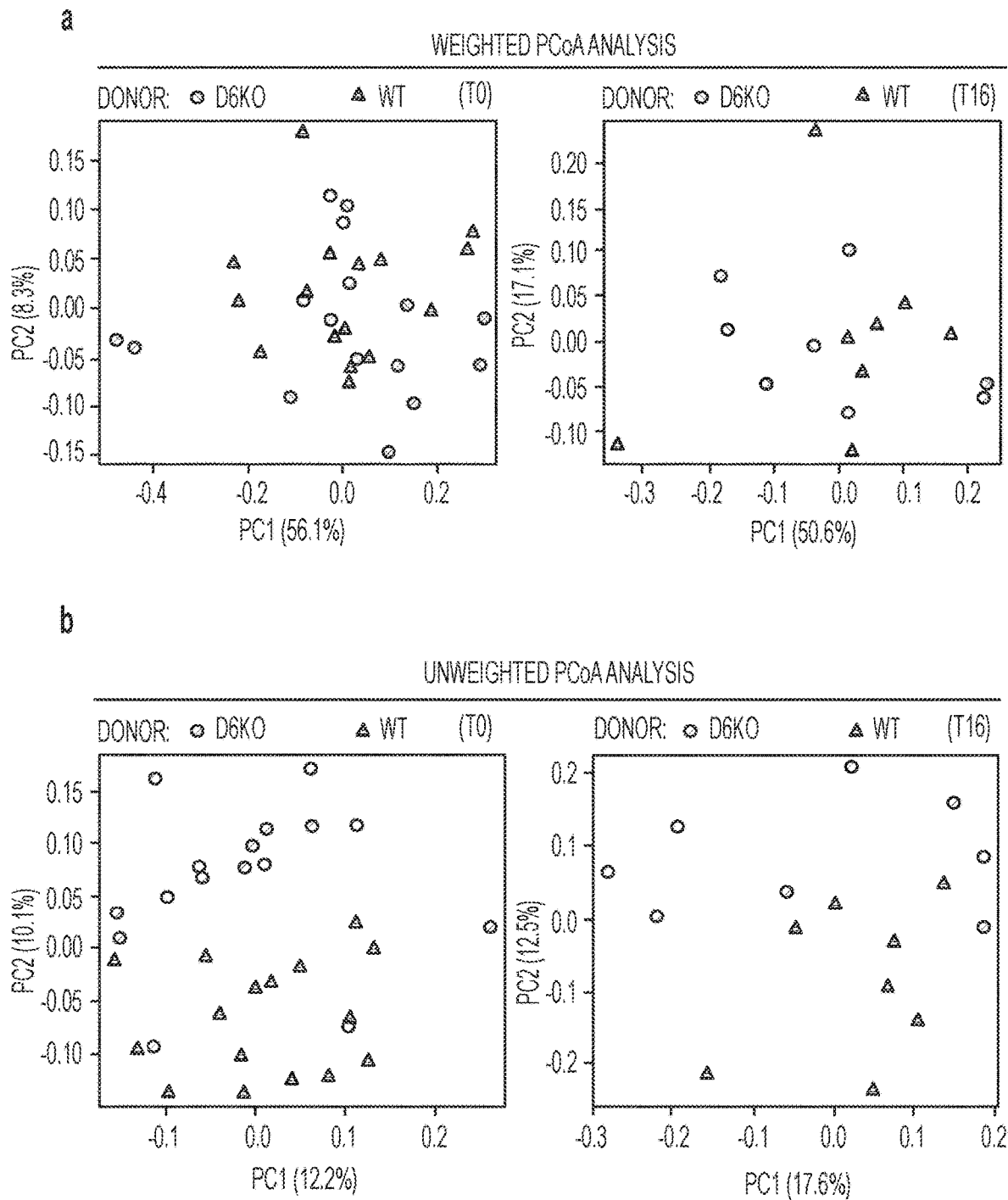
FIG. 3 shows that colonization of gut microbiota derived from dusp6-deficient mice contributes to obesity resistance in FMT recipient mice. a,b, Weighted UniFrac (a) and unweighted UniFrac (b) PCoA plots representing changes between chow diet (T0) or HFD (T16)-fed WT and D6KO FMT recipient mice. c,d, Composition of gut microbiota of FMT recipient mice before and after 16 weeks of HFD treatment at the phylum level. e,f, Abundance of Bacteroidetes and Firmicutes family members for each condition and time point. g, Changes in bacterial phyla after HFD treatment between WT and D6KO FMT mice. Values are means of each group. See also Table 2. h,i, LDA scores of the differentially abundant microbial clades (with LDA score>2 and significance of α<0.05, determined by Kruskal-Wallis test). j, LDA scores of the differentially abundant microbial clades (with LDA score>2 and significance of α<0.1, determined by Kruskal-Wallis test). Numbers of mice per group: T0: WT-CD, N=16; D6KO-CD, N=16; T16: WT-HFD, N=8; D6KO-HFD, N=8.

Data are presented as the mean ± SEM.
Double asterisks (P < 0.005) indicate statistical difference according to Mann-Whitney analysis performed on the comparison of Chow diet fed WT vs. D6KO FMT recipient mice or HFD fed WT vs. D6KO FMT recipient mice data set.
N.D.: Non-Detectable Visualization with unweighted, but not weighted, UniFrac-PCoA analysis showed that the faecal/gut microbiomes in WT-microbiota and D6KO microbiota recipient mice at T0 were clustered separately (FIG. 3a,b). This result indicated that recipient mice were differentially colonized by some unique groups of microbes. After HFD treatment, even under the same WT genetic background, the gut microbiomes of WT-microbiota and D6KO-microbiota recipient mice were separately clustered by both weighted and unweighted UniFrac-PCoA analysis (FIG. 3a,b), which suggested that the differential colonization contributes to the distinct gut microbiota response to HFD in recipient mice. We found that, unlike D6KO mice, before HFD treatment, D6KO-microbiota recipient mice demonstrated a similar taxonomic composition in most phyla, with only TM7 being less abundant (P=0.0014) when compared with WT microbiota recipient mice (Table 2 and FIG. 3c,d). In both WT-microbiota and D6KO-microbiota recipient mice, HFD strongly intervened to shape the gut microbiome at the phylum level, in particular increasing the Firmicutes/Bacteroidetes ratio (FIG. 3c,d,g).

We further analysed the composition of Bacteroidetes, Firmicutes and Proteobacteria at the family level (Table 2, FIG. 3e,f and FIG. 8e,f). In both WT-microbiota and D6KO-microbiota recipient mice, HFD reduced the proportion of Bacteroidaceae that was enriched in HFD-fed dusp6-deficient mice but did not affect the abundance of S24-7 (FIG. 3e). Although HFD treatment increased the proportion of Firmicutes in both WT and D6KO-derived microbiota recipient mice, several Firmicutes family members were less abundant in D6KO-microbiota recipients than WT-microbiota recipients, especially Streptococcaceae (P=0.0047) (FIG. 8e). Both before and after HFD treatment, a marked abundance of the Adlercreutzia genus within the Coriobacteriaceae family was observed in WT recipient mice (FIG. 3h-i). Because no enriched bacteria clade is found in D6KO-microbiota recipient mice with the LEfSe analysis default setting, we further adjusted the setting (Kruskal-Wallis test α=0.1) to search for possible clades associated with obesity resistance. The results showed increased abundance of Escherichia, Parabacteroides and Lactobacillus after six oral gavages of FMT in D6KO-microbiota recipient mice under a chow diet (FIG. 3j). After HFD, an increase of Proteobacteria was observed in D6KO-microbiota recipient mice (FIG. 8g). Because Akkermansia muciniphila was recently suggested to be associated with DIO resistance[17], we performed quantitative polymerase chain reaction (qPCR) analysis to analyse A. muciniphila, but it was not detected (with Ct values>35 or not detectable) in our WT and dusp6-deficient mice either before or after HFD in our animal facility.

To further confirm that the differential colonization of potential lean-associated microbes derived from dusp6-deficient mice contributes to DIO resistance, we cultured faecal microbiota from both WT and dusp6-deficient mice by using brain heart infusion (BHI) broth and performed culturable faecal microbiota transplantation (CFMT) on germ-free recipient WT mice. We found that, when compared with WT-CFMT mice, cultivable faecal microbiota from dusp6-deficient mice reduced the weight gain of transplanted mice after 16 weeks of HFD treatment (FIG. 8h,i). These results independently support that the initial colonization of D6KO microbiota confers DIO resistance in WT recipient mice.

2.4 Dusp6 Deficiency Regulates Basal Gut Transcriptome

By immuno-histochemistry (IHC) analysis, we found that DUSP6 protein was primarily expressed in intestinal epithelium, as well as some intra-epithelium immune cells (FIG. 4a). The depletion of DUSP6 protein and gene expression in D6KO mice was confirmed by IHC and quantitative reverse transcription (qRT) PCR analysis (FIG. 9a,b). To investigate how dusp6 deficiency affects the gut microbiome and confers DIO resistance, we performed intestinal transcriptome profiling with RNA-seq. The differentially expressed genes (DEGs) from HFD compared with CD in WT mice are generally regulated in a reverse manner in dusp6-deficient mice. In CD-fed mice, we found 889 significantly upregulated genes and 854 significantly downregulated genes (noted as basal DEGs) in dusp6-deficient mice compared with WT mice (FIG. 9c). These basal DEGs investigated with gene ontology (GO) enrichment analysis[18], with biological processes pulled out as being significantly enriched (designated as Up or Down biological processes). Up biological processes in dusp6-deficient mouse intestines are mostly involved in metabolism (for example, brown fat cell differentiation, fatty acid and triglyceride metabolism) and adhesion/cellular structure (for example, cell adhesion and extracellular matrix organization), while Down biological processes are mostly related to cell cycle and nucleic acid processing. Furthermore, these upregulated metabolism, cell-cell adhesion and extracellular structure related biological processes were exclusively found in dusp6-deficient mice. We also found distinct themes of HFD-regulated biological processes enriched in either the dusp6-deficient mice or WT mice. We visualized global potential links among the upregulated genes in dusp6-deficient mice, with Ppar signaling and tight junction (TJ) signaling pathways presented in magnified frames. Some representative genes of the Ppar signaling pathway and TJ pathway were further verified (FIG. 4b,c). The upregulation of TJ genes implies that dusp6 deficiency plays important roles in the regulation of gut barrier permeability. To examine this hypothesis, we created DUSP6 gene depletion in human colonic Caco-2 epithelial cell line (FIG. 9d) and assessed the transepithelial electrical resistance (TEER) of both WT and DUSP6-KO Caco-2 cells. Our results demonstrated that DUSP6 depletion conferred significant increases of TEER in DUSP6-KO Caco-2 cells when compared with WT Caco-2 cells (FIG. 9e). We further used fluorescein isothiocyanate (FITC)-Dextran to examine whether dusp6 deficiency affected gut permeability in vivo and found that dusp6-deficient mice showed reduced gut permeability under chow diet feeding (FIG. 9f). These results suggest that dusp6 deficiency exerts critical effects on regulating TJ genes expression and gut permeability. To further understand whether dusp6 deficiency also regulates Ppar and TJ pathways via the gut microbiota, we analysed the intestinal expression of the same genes in FMT recipient mice fed on CD. The results show that the expression of several genes, such as Ppar$\gamma$ and Ppm1j, responded to the D6KO-microbiota (FIG. 9g,h). These results indicate that a portion of the dusp6 deficiency mediated effects are secondary to gut microbiota changes and dusp6 plays important roles in maintaining the homeostasis between the gut mucosa and microbiota.

2.5 Dusp6 Deficiency Reverses HFD-Altered Gut Transcriptome

In HFD-fed D6KO mouse intestines, the Up biological processes are involved in cytoskeleton regulation, metabolismandGTPase signaling. Because Ras GTPase superfamily members could play profound roles in maintaining gut barrier integrity[19], dusp6 deficiency might also enhance intestinal barrier integrity under HFD stress. Many Down biological processes in HFD-fed dusp6-deficient mouse intestines were associated with immune system regulation, especially lymphocytes regulation and T cell differentiation and activation (FIG. 5b). We examined the difference in CD3+ T cells, CD19+ B cells and F4/80+ macrophages in WT and dusp6-deficient mice by qRT-PCR analysis (FIG. 5a-c). We found that HFD increased the amount of CD3+ T cells in HFD-fed WT mice but not in HFD-fed dusp6-deficient mice (FIG. 5a-c). We also investigated the expression level of T-cell CD4 in mouse intestine and found that dusp6 deficiency inhibited the HFD-mediated induction of CD4 gene expression (FIG. 5d). IHC analysis also showed that HFD increased infiltration of CD3+ and CD4+ T cells in WT mice but not in dusp6-deficient mice (FIG. 5e,f). These results suggest that dusp6 deficiency alters the HFD-induced behaviour of T lymphocytes in gut mucosal immunity.

We also applied DAVID KEGG pathway analysis on downregulated DEGs from the same comparison and there were 39 dusp6 deficiency downregulated genes involved in the cytokine-cytokine receptor interaction pathway. In this pathway, several genes belong to the tumour necrosis factor (TNF) superfamily, including lymphotoxin-$\alpha$ (Lt$\alpha$), lymphotoxin-$\beta$ (Lt$\beta$) and LIGHT (TNF superfamily member 14). Because polymorphisms of the TNF-lymphotoxin-$\alpha$ locus have also been implicated in an association with obesity and type II diabetes20,21, and mice deficient in lymphotoxin also showed altered gut microbiota and were resistant to DIO22, we examined the gene expression of Lt$\alpha$, Lt$\beta$ and Lt$\beta$ receptor (LT$\beta$R) in intestines. We found that dusp6 deficiency downregulated both Lt$\alpha$ and Lt$\beta$ expression in HFD-fed mice, but LT$\beta$R expression was not altered (FIG. 10).

To assess whether dusp6 deficiency exerts an intestinal HFD specific response to counteract HFD, we compared HFD-associated DEGs in WT and dusp6-deficient mice. We found that 423 of 761 genes downregulated by HFD in WT mice were upregulated in HFD-fed dusp6-deficient mice. Moreover, 140 of 201 HFD-upregulated genes in WT mice were downregulated in HFD-fed dusp6-deficient mice. These results suggest that dusp6 deficiency reversed the HFD-mediated effects at a transcription level in the intestine. DAVID pathway analysis on these dusp6-deficiency-reversed genes found that the adherens junction (AJ) pathway and TJ pathway were enriched. In both TJ and AJ pathways, the TJP-1 gene (encoding the ZO-1 protein) has a crucial role in the architecture of an intestinal barrier[23]. Although we did not detect any significant changes in TJP-1 gene expression after HFD treatment in either WT or dusp6-deficient mice (FIG. 11a), the junction structure of the ZO-1 protein was enhanced in HFD-fed dusp6-deficient mice (FIG. 6a). Because HFD could increase gut permeability and induce endotoxaemia in mice[24], we examined the serum endotoxin levels in WT and dusp6-deficient mice. Indeed, we found that HFD increased serum endotoxin levels in WT mice, and dusp6-deficient mice were resistant to this HFD-induced endotoxaemia (FIG. 11b). These results together suggest that dusp6 deficiency is important in coordinating the formation of intestinal TJs and protects the intestinal epithelial barrier from HFD induced interruption.

Several potentially important HFD-induced genes rescued by dusp6 deficiency are antimicrobial peptides (AMPs). DEFA5 is known to affect commensal composition, so the well-controlled expression of DEFA5 is critical for maintaining commensal homeostasis[25]. We found that dusp6 deficiency reversed HFD-mediated Defa5 induction (FIG. 6b) and also showed a trend of reversing HFD-mediated RegIII$\beta$ and RegIII$\gamma$ induction (FIG. 11c,d). These results imply that dusp6 deficiency regulates the gut microbiota response against HFD by maintaining physiological levels of expression for specific AMPs. Additionally, because HFD could reduce the proportion of segmented filamentous bacteria (SFB)[22] and the interruption of Ltbr or DEFA5 expression has been demonstrated to sustain the abundance of SFB[22,25], we examined the abundance of SFB in WT and dusp6-deficient faecal microbiota. We found that both before and after HFD treatment, dusp6-deficient mice harboured a higher amount of SFB than WT mice (FIG. 6c). In summary, our study suggests that both the colonization (D6KO-FMT/CFMT recipient mice partially phenocopy DIO resistance) and maintenance (dusp6-deficient mice have a unique gut microbiota response to HFD) of lean-associated microbiota play a role in obesity resistance (FIG. 6d).

3. Discussion

The homeostasis of the intestinal immunity is contributed by the gut epithelium, immune cells and microbiota[26]. We found that dusp6 deficiency alleviates HFD-induced T cell infiltration into the intestinal epithelium. Interestingly, dusp6 is constitutively expressed in CD4+ T cells, and this expression could be further induced by lipopolysaccharides via Toll-like receptor 4[27]. Follow-up studies in an Il10-deficient mouse colitis model revealed that Il10-/-/dusp6-/- double-knockout mice showed an enhanced severity of colitis, although dusp6-deficient mice did not show any colitis-associated phenotypes[28]. Because IL-10 is a critical factor that impacts many different immune cell functions[29] and IL-10 deficiency could alter gut microbiota associated with susceptibility to colitis[30,31], gut microbiota could potentially confound the observations in Il10-/-/dusp6-/- double-knockout mice. The dusp6 studies in an Il10-deficient mouse colitis model did suggest that gut microbiota might affect colitis in their mice, but no further microbiome profiling and causality experiments were conducted to dissect the roles of gut microbiota. Because Il10-deficient mouse colitis studies have also shown opposite roles of dusp6 in the development of different CD4+ T cell (Th1 and Th17) subsets, it is plausible that the functions of dusp6 are context-specific (for example, HFD versus colitis) and cell-type specific (for example, intestinal epithelial cells, Th1 and Th17 cells). Furthermore, our TJ and gut barrier permeability results suggest that dusp6 may also play critical roles in coordinating the interaction between gut epithelial cells and immune cells. Our study provides an integrated view of how dusp6 deficiency regulates homeostasis between the gut epithelium, mucosal immunity and microbiota.

One KEGG pathway pulled out from our intestinal transcriptome profiling is the Ppar pathway, known as an adipose tissue nutrient sensor in regulating fatty acid and lipid metabolic homeostasis[32]. Although the activation of Pparγ is conventionally linked to lipid accumulation by adipocytes and the aetiology of obesity[33], Pparγ could induce brown adipocyte differentiation via interaction with PGC-1 and UCP-1[34]. Because dusp6 has been shown to promote hepatic gluconeogenesis through PGC-1α/FOXO1 signalling[35], dusp6-deficiency-induced Pparγ expression might have a context-specific role in anti-obesity. A recent report has shown in vitro evidence that the overexpression of DUSP6 downregulates Pparγ and inhibits brown adipocyte differentiation[36]. These results are in agreement with the upregulation of Pparγ-related pathways identified from our gut transcriptome in dusp6-deficient mice. Recently, the gut microbiota was suggested to enhance blood-brain barrier integrity and increase the expression of TJ proteins[37]. We discovered that some TJ pathway genes are regulated by DUSP6 and that gut barrier integrity is enhanced in dusp6-deficient mice. A phospho-proteomic profiling study has shown increased phosphorylation of ZO-1 and ZO-2 in livers from dusp6-deficient mice on HFD6. Although the phosphorylation level change of ZO-1 and ZO-2 in the intestine of dusp6-deficient mice needs further investigation, these results suggest that dusp6 could be involved in the core regulation of the intestinal barrier at various levels of gene expression and/or protein phosphorylation. By remodelling the gut barrier integrity, dusp6 deficiency could confer resistance to HFD-induced microbiome alteration.

Our studies suggest that host dusp6 gene deficiency and HFD are involved in a tug of war for shaping the gut microbiota, and interactions among nutrients, microbes and host are more complex than previously understood. One important signature of the faecal/gut microbiota of HFD-fed D6KO mice we discovered is the reduced Firmicutes/Bacteroidetes ratio. The intervention of dusp6 deficiency to maintain a stable Firmicutes/Bacteroidetes ratio resistant to HFD challenge suggests that dusp6 is a suitable target for treating obesity or searching for lean-associated microbes. Altogether, our multiomics study is the first reported in D6KO mice in DIO. Given that the function of dusp6 in the context of obesity is complex and multifaceted, we believe that this study has laid a solid foundation for further investigation of the precise mechanisms involved in dusp6-deficiency-conferred obesity protection and development of microbiota therapeutics for obesity/metabolic diseases.

```
                       Sequence Information dual specificity protein phosphatase 6 [Mus musculus]
(NP_080544.1) (SEQ ID NO: 1)
         10          20          30          40          50
MIDTLRPVPF  ASEMAICKTV  SNLNEQLELG  NERLLLMDCR  PQELYESSHI 60          70          80          90         100
ESAINVAIPG  IMLRRLQKGN  LPVRALFTRC  EDRDRFTRRC  GTDTVVLYDE 110         120         130         140         150
NSSDWNENTG  GESVLGLLLK  KLKDEGCRAF  YLEGGFSKFQ  AEFALHCETN 160         170         180         190         200
LDGSCSSSSP  PLPVLGLGGL  RISSDSSSDI  ESDLDRDPNS  ATDSDGSPLS 210         220         230         240         250
NSQPSFPVEI  LPFLYLGCAK  DSTNLDVLEE  FGIKYILNVT  PNLPNLFENA 260         270         280         290         300
GEFKYKQIPI  SDHWSQNLSQ  FFPEAISFID  EARGKNCGVL  VHCLAGISRS 310         320         330         340         350
VTVTVAYLMQ  KLNLSMNDAY  DIVKMKKSNI  SPNFNFMGQL  LDFERTLGLS
```

```
                360        370        380
SPCDNRVPTP QLYFTTPSNQ NVYQVDSLQS T

Kinase-interaction motif > sp|Q9DBB1|64-74 (SEQ ID NO: 3)
RRLQKGNLPVR

Tyrosine-protein phosphatase Domain > sp|Q9DBB1|206-381 (SEQ ID NO: 4)
FPVEILPFLYLGCAKDSTNLDVLEEFGIKYILNVTPNLPNLFENAGEFKYKQIPISDHWS
QNLSQFFPEAISFIDEARGKNCGVLVHCLAGISRSVTVTVAYLMQKLNLSMNDAYDIVKM
KKSNISPNFNFMGQLLDFERTLGLSSPCDNRVPTPQLYFTTPSNQNVYQVDSLQST >NM_026268.3 Mus musculus dual specificity phosphatase 6 (Dusp6), mRNA
(SEQ ID NO: 2)
ATCCATTGAGGAGCTGCCTCGCACAGGGGGTGTGCTCTCGCGGAGTCCTAGGGACTGTGAGCAAACCCAG
TCTTGAATAATCCGGCGAGAAACACCGGGTTGGATCCGAGGTGCAGCCTCAGAGGGAAGGATTAAGAGCC
GCTAGACTTTTTTCTTTTCCCTTTTTCTCCTCTCAGTGGACAGGAGTCCGAATTAATTGGATTTCATTC
ACTGGGTAGGAACAAAACTGGGCACCTTCATTCAGAGAGAGAGATTCATTGACTCGGAGAGTGATCTGGT
GCAGAGGGACCACCGACTTGACTTCTGTGTCGCTTTCCCTAACCGCTAGCCTCGGCTTGGGAAAGGCGAG
GCGGAATCAAACCCCGCTCCGAGAGCGGGAGCTTCGCGCAGCGTGCTCGGCCTATGCCTGCCTCGAGGGG
CGTCTGCTAGGCACCCCGCCTTCTCCTGCAGCTCGACCCCCATGATAGATACGCTCAGACCCGTGCCCTT
CGCGTCGGAAATGGCGATCTGCAAGCAGGTGTCGTGGCTCAACGAGCAGCTGGAGCTGGGCAACGAACGG
CTTCTGCTGATGGACTGCCGACCACAGGAGCTGTACGAGTCGTCACACATCGAATCTGCCATTAATGTGG
CCATCCCCGGCATCATGCTGCGGCGTCTGCAGAAGGGCAACCTGCCCGTGCGTGCGCTCTTCACGCGCTG
CGAGGACCGGGACCGCTTTACCAGGCGCTGCGGCACCGACACCGTGGTGCTGTACGACGAGAATAGCAGC
GACTGGAATGAGAACACTGGTGGAGAGTCGGTCCTCGGGCTGCTGCTCAAGAAACTCAAAGACGAGGGCT
GCCGGGCGTTCTACCTGGAAGGTGGCTTCAGTAAGTTCCAGGCCGAGTTCGCCCTGCACTGCGAGACCAA
TCTAGACGGCTCGTGCAGCAGCAGTTCCCCGCCTTTGCCAGTGCTGGGGCTCGGGGGCCTGCGGATCAGC
TCGGACTCTTCCTCGGACATTGAGTCTGACCTTGACCGAGACCCCAATAGTGCAACGGACTCTGATGGCA
GCCCGCTGTCCAACAGCCAGCCTTCCTTCCCGGTGGAGATTTTGCCCTTCCTTTACCTGGGCTGTGCCAA
GGACTCGACCAACTTGGACGTGTTGGAAGAGTTTGGCATCAAGTACATCTTGAATGTCACCCCCAATTTG
CCCAATCTGTTTGAGAATGCGGGCGAGTTCAAATACAAGCAAATTCCTATCTCGGATCACTGGAGCCAAA
ACCTGTCCCAGTTTTTCCCTGAGGCCATTTCTTTCATAGATGAAGCCCGAGGCAAAAACTGTGGTGTCCT
GGTGCATTGCTTGGCAGGTATCAGCCGCTCTGTCACCGTGACAGTGGCGTACCTCATGCAGAAGCTCAAC
CTGTCCATGAACGATGCTTACGACATTGTTAAGATGAAGAAGTCCAACATCTCCCCCAACTTCAACTTCA
TGGGCCAGCTGCTTGACTTCGAAAGGACCCTGGGACTGAGCAGCCCTTGTGACAACCGTGTCCCCACTCC
GCAGCTGTACTTCACCACGCCCTCCAACCAGAACGTCTACCAGGTGGACTCCCTGCAGTCTACGTGAAAG
GCACCCACCTCTCCTAGCCGGGAGTTGTCCCCATTCCTTCAGTTCCTCTTGAGCAGCATCGACCAGGCTG
CTTTCTTTCTGTGTGTGGCCCCGGGTGTCAAAAGTGTCACCAGCTGTCTGTGTTAGACAAGGTTGCCAAG
TGCAAAATTGGTTATTACGGAGGGAGAGATTTGCTCCATTCATTGTTTTTTGGAAGGACAGGACATGCT
GTCTCTAGATCCAGCAATAGGTTTGCTTCTGTACCCCAGCCTACCCAAGCAGGGACTGGACATCCATCCA
GATAGAGGGTAGCATAGGAATAGGGACAGGAGCATCTGTTCTTTAAGGCCTTGTATGGCTGTTTCCTGTT
GCATCTGGAACTAACTATATATATTGTCTTCAGTGAAGACTGATTCAACTTTGGGTATAGTGGAGCCAAA
GAGATTTTTAGCTCTGTATTTGCGGTATCGGTTTAGAAGACAAAAAAAATTAAAACCTGATACTTTTATC
TGATTATTGTAAATATTTGATCTTCAATCACTTGACAGTGTTTGTTTGGCTTGTATTTGTTTTTATCTT
TGGGCTTAAAAGAGATCCAAAGAGAGAAAGAGCAGTATGCCACTTCTTAGAACAAAAGTATAAGGAAAAA
AATGTTCTTTTTAATCCAAAGGGTATATTTGCAGCATGCTTGACCTTGATGTACCAATTCTGACGGCATT
TTCGTGGATATTATTATCACTAAGACTTTGTTATGATGAGGTCTTCAGTCTCTTTCATATATCTTCCTTG
TAACTTTTTTTTCCTCTTAATGTAGTTTTGACTCTGCCTTACCTTTTGTAAATATTTGGCTTACAGTGTC
TCAAGGGGTATTTTGGAAAGACACCAAAATTGTGGGTTCACTTTTTTTTTTTTTTAAATAACTTCAGC
TGTGCTAAACAGCATATTACCTCTGTACAAAATTCTTCAGGGAGTGTCACCTCAAATGCAATACTTTGGG
TTGGTTTCTTTCCTTTTAAAAAAAAATACGAAACTGGAAGTGTGTGTATGTGTGCGAGTATGAGCGCCCA
TTTGGTGGATGCAACAGGTTGAGAGGAAGGGAGAATTAACTTGCTCCATGATGTTCGTGGTGTAAAGTTT
TGAGCTGGAATTTATTATAAGAATGTAAAACCTTAAATTATTAATAAATAACTATTTTGGCTATTGAAAA
AAAAAAAAAAAAA
```

REFERENCES

1. Lang, R., Hammer, M. & Mages, J. DUSP meet immunology dual specificity MAPK phosphatases in control of the inflammatory response. *J. Immunol.* 177, 7497-7504 (2006).
2. Jeffrey, K. L., Camps, M., Rommel, C. & Mackay, C. R. Targeting dual-specificity phosphatases manipulating MAP kinase signalling and immune responses. *Nat. Rev. Drug. Discov.* 6, 391-403 (2007).
3. Li, C., Scott, D. A., Hatch, E., Tian, X. & Mansour, S. L. Dusp6 (Mkp3) is a negative feedback regulator of FGF-stimulated ERK signaling during mouse development. *Development* 134, 167-176 (2007).
4. Maillet, M. et al. DUSP6 (MKP3) null mice show enhanced ERK1/2 phosphorylation at baseline and increased myocyte proliferation in the heart affecting disease susceptibility. *J. Biol. Chem.* 283, 31246-31255 (2008).
5. Feng, B., He, Q. & Xu, H. FOXO1-dependent up-regulation of MAP kinase phosphatase 3 (MKP-3) mediates glucocorticoid-induced hepatic lipid accumulation in mice. *Mol. Cell. Endocrinol.* 393, 46-55 (2014).
6. Feng, B. et al. Mitogen-activated protein kinase phosphatase 3 (MKP-3)-deficient mice are resistant to diet-induced obesity. *Diabetes* 63, 2924-2934 (2014).
7. Tilg, H. & Kaser, A. Gut microbiome, obesity, and metabolic dysfunction. *J. Clin. Invest.* 121, 2126-2132 (2011).
8. Everard, A. et al. Microbiome of prebiotic-treated mice reveals novel targets involved in host response during obesity. *ISMS J.* 8, 2116-2130 (2014).

9. Walters, W. A., Xu, Z. & Knight, R. Meta-analyses of human gut microbes associated with obesity and IBD. *FEBS Lett.* 588, 4223-4233 (2014).
10. Parks, B. W. et al. Genetic control of obesity and gut microbiota composition in response to high-fat, high-sucrose diet in mice. *Cell Metab.* 17, 141-152 (2013).
11. Lozupone, C. A., Hamady, M., Kelley, S. T. & Knight, R. Quantitative and qualitative beta diversity measures lead to different insights into factors that structure microbial communities. *Appl. Environ. Microbiol.* 73, 1576-1585 (2007).
12. Lozupone, C., Lladser, M. E., Knights, D., Stombaugh, J. & Knight, R. UniFrac: an effective distance metric for microbial community comparison. *ISME J.* 5, 169-172 (2011).
13. Ley, R. E., Turnbaugh, P. J., Klein, S. & Gordon, J. I. Microbial ecology human gut microbes associated with obesity. *Nature* 444, 1022-1023 (2006).
14. Neyrinck, A. M. et al. Prebiotic effects of wheat arabinoxylan related to the increase in bifidobacteria, *Roseburia* and *Bacteroides/Prevotella* in diet-induced obese mice. *PLoS ONE* 6, e20944 (2011).
15. Conterno, L., Fava, F., Viola, R. & Tuohy, K. M. Obesity and the gut microbiota: does up-regulating colonic fermentation protect against obesity and metabolic disease? *Genes Nutr.* 6, 241-260 (2011).
16. Zhang, H. et al. Human gut microbiota in obesity and after gastric bypass. *Proc. Natl Acad. Sci. USA* 106, 2365-2370 (2009).
17. Everard, A. et al. Cross-talk between *Akkermansia muciniphila* and intestinal epithelium controls diet-induced obesity. *Proc. Natl Acad. Sci. USA* 110, 9066-9071 (2013).
18. Blake, J. A. Ten quick tips for using the gene ontology. *PLoS Comput. Biol.* 9, e1003343 (2013).
19. Citalan-Madrid, A. F., Garcia-Ponce, A., Vargas-Robles, H., Betanzos, A. & Schnoor, M. Small GTPases of the Ras superfamily regulate intestinal epithelial homeostasis and barrier function via common and unique mechanisms. *Tissue Barriers* 1, e26938 (2013).
20. Norman, R. A., Bogardus, C. & Ravussin, E. Linkage between obesity and a marker near the tumor necrosis factor-alpha locus in Pima Indians. *J. Clin. Invest.* 96, 158-162 (1995).
21. Mahajan, A. et al. Obesity-dependent association of TNF-LTA locus with type 2 diabetes in North Indians. *J. Mol. Med.* 88, 515-522 (2010).
22. Upadhyay, V. et al. Lymphotoxin regulates commensal responses to enable diet-induced obesity. *Nat. Immunol.* 13, 947-953 (2012).
23. Tornavaca, O. et al. ZO-1 controls endothelial adherens junctions, cell-cell tension, angiogenesis, and barrier formation. *J. Cell Biol.* 208, 821-838 (2015).
24. Cani, P. D. et al. Changes in gut microbiota control metabolic endotoxemiainduced inflammation in high-fat diet-induced obesity and diabetes in mice. *Diabetes* 57, 1470-1481 (2008).
25. Salzman, N. H. et al. Enteric defensins are essential regulators of intestinal microbial ecology. *Nat. Immunol.* 11, 76-83 (2010).
26. Peterson, L. W. & Artis, D. Intestinal epithelial cells regulators of barrier function and immune homeostasis. *Nat. Rev. Immunol.* 14, 141-153 (2014).
27. Gonzalez-Navajas, J. M. et al. TLR4 signaling in effector CD4+ T cells regulates TCR activation and experimental colitis in mice. *J. Clin. Invest.* 120, 570-581 (2010).
28. Bertin, S. et al. Dual-specificity phosphatase 6 regulates CD4+ T-cell functions and restrains spontaneous colitis in IL-10-deficient mice. *Mucosal Immunol.* 8, 505-515 (2015).
29. Saraiva, M. & O'Garra, A. The regulation of IL-10 production by immune cells. *Nat. Rev. Immunol.* 10, 170-181 (2010).
30. Maharshak, N. et al. Altered enteric microbiota ecology in interleukin 10-deficient mice during development and progression of intestinal inflammation. *Gut Microbes* 4, 316-324 (2013).
31. Yang, I. et al. Intestinal microbiota composition of interleukin-10 deficient C57BL/6J mice and susceptibility to *Helicobacter hepaticus*-induced colitis. *PLoS ONE* 8, e70783 (2013).
32. Berger, J. & Moller, D. E. The mechanisms of action of PPARs. *Annu. Rev. Med.* 53, 409-435 (2002).
33. Stienstra, R., Duval, C., Muller, M. & Kersten, S. PPARs, obesity, and inflammation. *PPAR Res.* 2007, 95974 (2007).
34. Puigserver, P. et al. A cold-inducible coactivator of nuclear receptors linked to adaptive thermogenesis. *Cell* 92, 829-839 (1998).
35. Wu, Z. et al. MAPK phosphatase-3 promotes hepatic gluconeogenesis through dephosphorylation of forkhead box O1 in mice. *J. Clin. Invest.* 120, 3901-3911 (2010).
36. Kim, W. K. et al. MAP kinase phosphatase 3 inhibits brown adipocyte differentiation via regulation of Erk phosphorylation. *Mol. Cell Endocrinol.* 416, 70-76 (2015).
37. Braniste, V. et al. The gut microbiota influences blood-brain barrier permeability in mice. *Sci. Transl. Med.* 6, 263ra158 (2014).
38. Caporaso, J. G. et al. QIIME allows analysis of high-throughput community sequencing data. *Nat. Methods* 7, 335-336 (2010).
39. Edgar, R. C. Search and clustering orders of magnitude faster than BLAST. *Bioinformatics* 26, 2460-2461 (2010).
40. Wang, F. et al., *Analytical biochemistry* 399, 211-217, doi: 10.1016/j.ab.2009.12.029 (2010)
41. Galmozzi, A et al., *Cell reports* 9, 1584-1593, doi: 10.1016/j.celrep.2014.10.066 (2014)

What is claimed is:

1. A composition, which comprises:
   a combination consisting of: (i) substantially purified Actinobacteria, (ii) substantially purified Bacteroidetes, (iii) substantially purified Cyanobacteria, (iv) substantially purified Deferribacteres, (v) substantially purified Firmicutes, (vi) substantially purified Proteobacteria, (vii) substantially purified TM7, and (viii) substantially purified Tenericutes; and
   another combination consisting of: (a) substantially purified Bacteroidaceae. (b) substantially purified S24-7, (b) substantially purified Rikenellaceae, (d) substantially purified Porphyromonadaceae, (e) substantially purified Odoribacteraceae, (f) substantially purified Ruminococcaceae, (g) substantially purified Erysipelotrichaceae, (h) Lachnospiraceae, (i) Lactobacillaceae, and (j) Clostridiaceae.

2. The composition of claim 1, which comprises (iv) substantially purified Deferribacteres or (v) substantially purified Firmicutes, or a combination thereof.

3. The composition of claim 1, which comprises (f) substantially purified Ruminococcaceae or (h) Lachnospiraceae, or a combination thereof.

4. The composition of claim 1, wherein (ii) substantially purified Bacteroidetes and (v) substantially purified Firmicutes are present in the composition in a ratio of about 1: 1.2.

5. The composition of claim 1, wherein (i) substantially purified Actinobacteria, (iv) substantially purified Deferribacteres and (vi) substantially purified Proteobacteria are present in the composition in a ratio of about 1: 120: 20.

6. The composition of claim 1, wherein (i) substantially purified Actinobacteria, (ii) substantially purified Bacteroidetes, (iv) substantially purified Deferribacteres, (v) substantially purified Firmicutes, and (vi) substantially purified Proteobacteria are present in the composition in a ratio of about 1: 1400: 120: 1770: 20.

7. The composition of claim 1, which is prepared by a method comprising
   (a) providing a dual-specificity phosphatase 6 (dusp6) deficient non-human animal; and
   (b) collecting gut microbiota from the dusp6 deficient animal.

8. The composition of claim 1, which is formulated as a food product, dietary supplement or medicament.

9. The composition of claim 1, wherein the composition is for use in altering a relative abundance of microbiota in a subject.

10. The composition of claim 1, wherein the composition is for use in reducing body weight and/or body fat, preventing an increase in body weight and/or body fat, and/or treating obesity or its associated disorders or conditions in a subject.

11. A method for altering a relative abundance of microbiota in a subject in need thereof, comprising administering to the subject an effective amount of a composition of claim 1.

12. The method of claim 11, wherein the amount of the composition is effective in decreasing a relative abundance of TM7 in the subject.

13. The method of claim 11, wherein the amount of the composition is effective in decreasing a relative abundance of Streptococcaceae in the subject.

14. The method of claim 11, wherein the amount of the composition is effective in increasing a relative abundance of Escherichia, Parabacteroides and/or Lactobacillus in the subject.

15. The method of claim 11, wherein the amount of the composition is effective in increasing a relative abundance of Proteobacteria in the subject.

16. A method for reducing body weight and/or body fat or preventing an increase in body weight and/or body fat in a subject in need thereof, comprising administering to the subject an effective amount of a composition of claim 1.

17. A method for treating obesity or its associated disorders or conditions in a subject in need thereof, comprising administering to the subject an effective amount of a composition of claim 1.

18. The method of claim 17, wherein the obesity is diet induced obesity.

19. The method of claim 17, wherein the obesity associated disorders or conditions are selected from the group consisting of type 2 diabetes, hyperglycemia, glucose intolerance, dyslipidemia, insulin resistance, hyperinsulinemia, fatty liver, cardiovascular disease, stroke, and cancer.

20. The method of claim 17, wherein the amount of the composition is ineffective in reducing food intake or ineffective in reducing lean body mass.

* * * * *